US008876894B2

(12) United States Patent
Tuval et al.

(10) Patent No.: US 8,876,894 B2
(45) Date of Patent: Nov. 4, 2014

(54) LEAFLET-SENSITIVE VALVE FIXATION MEMBER

(75) Inventors: Yosi Tuval, Netanya (IL); Ido Kilemnik, Herzliya (IL); Raphael Benary, Tel Aviv (IL)

(73) Assignee: Medtronic Ventor Technologies Ltd., Netanya, IL (US)

( * ) Notice: Subject to any disclaimer, the term of this patent is extended or adjusted under 35 U.S.C. 154(b) by 2356 days.

(21) Appl. No.: 11/726,863

(22) Filed: Mar. 23, 2007

(65) Prior Publication Data

US 2008/0071361 A1     Mar. 20, 2008

Related U.S. Application Data

(60) Provisional application No. 60/845,728, filed on Sep. 19, 2006.

(51) Int. Cl.
*A61F 2/24*     (2006.01)
*A61F 2/95*     (2013.01)

(52) U.S. Cl.
CPC ....... *A61F 2/2418* (2013.01); *A61F 2250/0039* (2013.01); *A61F 2002/9522* (2013.01); *A61F 2/2436* (2013.01)
USPC ........................................ 623/2.18; 623/2.14

(58) Field of Classification Search
USPC ............ 623/1.24–1.26, 2.14–2.19, 2.38–2.41
See application file for complete search history.

(56) References Cited

U.S. PATENT DOCUMENTS

| | | |
|---|---|---|
| 3,334,629 A | 8/1967 | Cohn |
| 3,409,013 A | 11/1968 | Berry |
| 3,540,431 A | 11/1970 | Mobin-Uddin |
| 3,587,115 A | 6/1971 | Shiley |
| 3,628,535 A | 12/1971 | Ostrowsky et al. |
| 3,642,004 A | 2/1972 | Osthagen et al. |
| 3,657,744 A * | 4/1972 | Ersek ............................ 128/898 |
| 3,671,979 A | 6/1972 | Moulopoulos |
| 3,714,671 A | 2/1973 | Edwards et al. |
| 3,755,823 A | 9/1973 | Hancock |

(Continued)

FOREIGN PATENT DOCUMENTS

| | | |
|---|---|---|
| CN | 2007-100074433 | 8/2007 |
| EP | 0103546 | 3/1984 |

(Continued)

OTHER PUBLICATIONS

U.S. Appl. No. 60/530,781, filed Dec. 2003.

(Continued)

*Primary Examiner* — Paul Prebilic

(57) ABSTRACT

A prosthesis is provided for implantation at a native semilunar valve of a native valve complex. The prosthesis includes a distal fixation member, configured to be positioned in a downstream artery, and to apply a first axial force directed toward a ventricle. The prosthesis further includes a proximal fixation member coupled to the distal fixation member, the proximal fixation member configured to be positioned at least partially on a ventricular side of the native valve complex, and to apply a second axial force directed toward the downstream artery, such that application of the first and second forces couples the prosthesis to the native valve complex by axially sandwiching the native valve complex from a downstream side and the ventricular side thereof. The prosthesis is configured, upon implantation thereof, to embrace, without squeezing, leaflets of the native semilunar valve. Other embodiments are also described.

19 Claims, 24 Drawing Sheets

(56) References Cited

U.S. PATENT DOCUMENTS

| | | |
|---|---|---|
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,078,268 A | 3/1978 | Possis |
| 4,106,129 A | 8/1978 | Carpentier et al. |
| 4,222,126 A | 9/1980 | Boretos et al. |
| 4,233,690 A | 11/1980 | Akins |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,470,157 A | 9/1984 | Love |
| 4,491,986 A | 1/1985 | Gabbay |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,681,908 A | 7/1987 | Broderick et al. |
| 4,710,192 A | 12/1987 | Liotta et al. |
| 4,733,665 A | 3/1988 | Palmaz |
| 4,777,951 A | 10/1988 | Cribier et al. |
| 4,787,899 A | 11/1988 | Lazarus |
| 4,787,901 A | 11/1988 | Baykut |
| 4,796,629 A | 1/1989 | Grayzel |
| 4,819,751 A | 4/1989 | Shimada et al. |
| 4,834,755 A | 5/1989 | Silvestrini et al. |
| 4,846,830 A | 7/1989 | Knoch et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A | 8/1991 | Lane |
| 5,047,041 A | 9/1991 | Samuels |
| 5,059,177 A | 10/1991 | Towne et al. |
| 5,061,273 A | 10/1991 | Yock |
| 5,085,635 A | 2/1992 | Cragg |
| 5,089,015 A | 2/1992 | Ross |
| 5,108,425 A | 4/1992 | Hwang |
| 5,152,771 A | 10/1992 | Sabbaghian et al. |
| 5,161,547 A | 11/1992 | Tower |
| 5,163,953 A | 11/1992 | Vince |
| 5,167,628 A * | 12/1992 | Boyles .................... 604/103.07 |
| 5,178,632 A | 1/1993 | Hanson |
| 5,217,483 A | 6/1993 | Tower |
| 5,232,445 A | 8/1993 | Bonzel |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum |
| 5,344,442 A | 9/1994 | Deac |
| 5,350,398 A | 9/1994 | Pavcnik et al. |
| 5,354,330 A | 10/1994 | Hanson et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,480,424 A | 1/1996 | Cox |
| 5,489,294 A | 2/1996 | McVenes et al. |
| 5,489,297 A | 2/1996 | Duran |
| 5,496,346 A | 3/1996 | Horzewski et al. |
| 5,500,014 A | 3/1996 | Quijano et al. |
| 5,507,767 A | 4/1996 | Maeda et al. |
| 5,545,209 A | 8/1996 | Roberts et al. |
| 5,545,211 A | 8/1996 | An et al. |
| 5,545,214 A | 8/1996 | Stevens |
| 5,554,185 A | 9/1996 | Block et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A | 2/1998 | Vallana et al. |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |
| 5,906,619 A | 5/1999 | Olson et al. |
| 5,907,893 A | 6/1999 | Zadno-Azizi et al. |
| 5,908,451 A | 6/1999 | Yeo |
| 5,908,452 A | 6/1999 | Bokros et al. |
| 5,913,842 A | 6/1999 | Boyd et al. |
| 5,925,063 A | 7/1999 | Khosravi |
| 5,957,949 A | 9/1999 | Leonhardt |
| 5,964,405 A | 10/1999 | Benary et al. |
| 5,968,068 A | 10/1999 | Dehdashtian et al. |
| 5,984,957 A | 11/1999 | Laptewicz, Jr. et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,076,742 A | 6/2000 | Benary |
| 6,091,042 A | 7/2000 | Benary |
| 6,110,201 A | 8/2000 | Quijano et al. |
| 6,146,366 A | 11/2000 | Schachar |

(56) References Cited

U.S. PATENT DOCUMENTS

| | | |
|---|---|---|
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon et al. |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,287,339 B1 | 9/2001 | Vazquez et al. |
| 6,296,662 B1 | 10/2001 | Caffey |
| 6,299,637 B1 | 10/2001 | Shaolian et al. |
| 6,302,906 B1 | 10/2001 | Goicoechea et al. |
| 6,309,382 B1 | 10/2001 | Garrison et al. |
| 6,309,417 B1 * | 10/2001 | Spence et al. ............. 623/2.11 |
| 6,312,465 B1 | 11/2001 | Griffin |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,799 B1 | 9/2002 | Schreck |
| 6,458,153 B1 | 10/2002 | Bailey |
| 6,461,382 B1 | 10/2002 | Cao |
| 6,468,303 B1 | 10/2002 | Amplatz et al. |
| 6,475,239 B1 | 11/2002 | Campbell et al. |
| 6,482,228 B1 | 11/2002 | Norred |
| 6,488,704 B1 | 12/2002 | Connelly et al. |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,558,418 B2 | 5/2003 | Carpentier et al. |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,582,462 B1 | 6/2003 | Andersen et al. |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,767,362 B2 | 7/2004 | Schreck |
| 6,769,434 B2 | 8/2004 | Liddicoat et al. |
| 6,786,925 B1 | 9/2004 | Schoon |
| 6,790,229 B1 | 9/2004 | Berreklouw ............... 623/2.1 |
| 6,792,979 B2 | 9/2004 | Konya et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,018,406 B2 | 3/2006 | Seguin et al. |
| 7,018,408 B2 | 3/2006 | Bailey |
| 7,041,128 B2 | 5/2006 | McGuckin, Jr. et al. |
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shiu et al. |
| 7,115,141 B2 | 10/2006 | Menz et al. |
| 7,137,184 B2 | 11/2006 | Schreck |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. . 623/2.18 |
| 7,252,682 B2 | 8/2007 | Seguin ..................... 623/2.17 |
| 7,261,732 B2 | 8/2007 | Justino ..................... 623/1.24 |
| 7,267,686 B2 | 9/2007 | Dimatteo et al. |
| 7,300,457 B2 | 11/2007 | Palmaz |
| 7,300,463 B2 | 11/2007 | Liddicoat |
| 7,311,730 B2 * | 12/2007 | Gabbay ..................... 623/2.38 |
| 7,316,706 B2 | 1/2008 | Bloom et al. |
| 7,329,278 B2 | 2/2008 | Seguin et al. |
| 7,335,218 B2 | 2/2008 | Wilson et al. |
| 7,338,520 B2 | 3/2008 | Bailey et al. |
| 7,374,571 B2 | 5/2008 | Pease et al. |
| 7,381,218 B2 | 6/2008 | Schreck |
| 7,384,411 B2 | 6/2008 | Condado |
| 7,399,315 B2 | 7/2008 | Iobbi |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn |

(56) References Cited

U.S. PATENT DOCUMENTS

| | | |
|---|---|---|
| 7,556,646 B2 | 7/2009 | Yang et al. |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1* | 9/2001 | Bailey et al. ............... 623/1.24 |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0026233 A1 | 2/2002 | Shaknovich |
| 2002/0029014 A1 | 3/2002 | Jayaraman |
| 2002/0032480 A1 | 3/2002 | Spence et al. |
| 2002/0032481 A1 | 3/2002 | Gabbay ....................... 623/2.11 |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0186558 A1 | 12/2002 | Plank et al. |
| 2002/0193871 A1 | 12/2002 | Beyersdorf et al. |
| 2003/0014104 A1 | 1/2003 | Cribier |
| 2003/0023300 A1 | 1/2003 | Bailey |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay ....................... 623/2.11 |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130727 A1 | 7/2003 | Drasler et al. |
| 2003/0130729 A1 | 7/2003 | Paniagua et al. |
| 2003/0139804 A1 | 7/2003 | Hankh et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0171805 A1 | 9/2003 | Berg |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0212410 A1 | 11/2003 | Stenzel et al. |
| 2003/0212454 A1 | 11/2003 | Scott et al. |
| 2003/0225445 A1 | 12/2003 | Derus et al. |
| 2003/0236568 A1 | 12/2003 | Hojeibane et al. ........... 623/1.24 |
| 2004/0034411 A1 | 2/2004 | Quijano et al. |
| 2004/0039436 A1 | 2/2004 | Spenser et al. |
| 2004/0044402 A1 | 3/2004 | Jung et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0059429 A1 | 3/2004 | Amin et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Sequin et al. |
| 2004/0093070 A1 | 5/2004 | Hojeibane et al. ........... 623/1.15 |
| 2004/0097788 A1 | 5/2004 | Mourlas et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Lobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0236411 A1 | 11/2004 | Sarac et al. |
| 2004/0254636 A1 | 12/2004 | Flagle et al. |
| 2004/0260389 A1 | 12/2004 | Case et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075720 A1* | 4/2005 | Nguyen et al. ............... 623/1.26 |
| 2005/0075724 A1 | 4/2005 | Svanidze |
| 2005/0075725 A1 | 4/2005 | Rowe |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1 | 5/2005 | Paniagua |
| 2005/0119688 A1 | 6/2005 | Berheim |
| 2005/0131438 A1 | 6/2005 | Cohn |
| 2005/0137686 A1 | 6/2005 | Salahieh et al. |
| 2005/0137688 A1 | 6/2005 | Salahieh et al. |
| 2005/0137689 A1* | 6/2005 | Salahieh et al. ............. 623/2.11 |
| 2005/0137690 A1* | 6/2005 | Salahieh et al. ............. 623/2.11 |
| 2005/0137691 A1 | 6/2005 | Salahieh et al. |
| 2005/0137692 A1 | 6/2005 | Haug |
| 2005/0137695 A1 | 6/2005 | Salahieh et al. |
| 2005/0137698 A1 | 6/2005 | Salahieh et al. |
| 2005/0137701 A1 | 6/2005 | Salahieh |

(56) References Cited

U.S. PATENT DOCUMENTS

| | | |
|---|---|---|
| 2005/0143809 A1 | 6/2005 | Salahieh et al. |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0182483 A1 | 8/2005 | Osborne et al. |
| 2005/0187616 A1 | 8/2005 | Realyvasquez |
| 2005/0197695 A1 | 9/2005 | Stacchino et al. |
| 2005/0203549 A1 | 9/2005 | Realyvasquez |
| 2005/0203605 A1 | 9/2005 | Dolan |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0025855 A1 | 2/2006 | Lashinski et al. |
| 2006/0025857 A1 * | 2/2006 | Bergheim et al. ............ 623/2.18 |
| 2006/0047338 A1 | 3/2006 | Jenson et al. |
| 2006/0052867 A1 | 3/2006 | Revuelta et al. |
| 2006/0058775 A1 | 3/2006 | Stevens et al. |
| 2006/0058872 A1 | 3/2006 | Salahieh et al. |
| 2006/0074485 A1 | 4/2006 | Realyvasquez |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0149360 A1 * | 7/2006 | Schwammenthal et al. . 623/1.24 |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0206192 A1 | 9/2006 | Tower et al. |
| 2006/0206202 A1 | 9/2006 | Bonhoeffer et al. |
| 2006/0247763 A1 | 11/2006 | Slater |
| 2006/0253191 A1 | 11/2006 | Salahieh et al. |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 * | 12/2006 | Wilson et al. ................ 623/1.13 |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010876 A1 | 1/2007 | Salahieh et al. |
| 2007/0010878 A1 | 1/2007 | Rafiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Jantz |
| 2007/0078509 A1 | 4/2007 | Lotfy et al. |
| 2007/0078510 A1 | 4/2007 | Ryan |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla et al. |
| 2007/0100449 A1 | 5/2007 | O'Neil et al. |
| 2007/0112415 A1 | 5/2007 | Bartlett |
| 2007/0112422 A1 | 5/2007 | Dehdashtian |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0213813 A1 | 9/2007 | Von Segesser et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0071369 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 * | 1/2009 | Goetz et al. .................. 623/2.18 |
| 2009/0012600 A1 | 1/2009 | Styrc et al. |
| 2009/0048656 A1 | 2/2009 | Wen |
| 2009/0054976 A1 | 2/2009 | Tuval et al. |
| 2009/0069886 A1 | 3/2009 | Suri et al. |
| 2009/0069887 A1 | 3/2009 | Righini et al. |
| 2009/0069889 A1 | 3/2009 | Suri et al. |
| 2009/0138079 A1 | 5/2009 | Tuval et al. |
| 2009/0164004 A1 | 6/2009 | Cohn |
| 2009/0171447 A1 | 7/2009 | Von Segesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0234443 A1 | 9/2009 | Ottma et al. |
| 2009/0240264 A1 | 9/2009 | Tuval et al. |
| 2009/0240320 A1 | 9/2009 | Tuval |

(56) References Cited

U.S. PATENT DOCUMENTS

| | | | |
|---|---|---|---|
| 2010/0094411 A1 | 4/2010 | Tuval et al. | |
| 2010/0100167 A1 | 4/2010 | Bortlein et al. | |
| 2010/0131054 A1 | 5/2010 | Tuval et al. | |
| 2010/0137979 A1 | 6/2010 | Tuval et al. | |
| 2011/0029066 A1* | 2/2011 | Gilad et al. | 623/1.24 |

FOREIGN PATENT DOCUMENTS

| | | |
|---|---|---|
| EP | 0597967 | 12/1994 |
| EP | 0850607 | 7/1998 |
| EP | 1057459 A1 | 6/2000 |
| EP | 1057460 A1 | 6/2000 |
| EP | 1088529 | 4/2001 |
| EP | 1255510 | 11/2002 |
| EP | 0937439 B1 | 9/2003 |
| EP | 1340473 | 9/2003 |
| EP | 0819013 | 6/2004 |
| EP | 1 469 797 | 11/2005 |
| GB | 2056023 | 3/1981 |
| GB | 2 433 700 | 12/2007 |
| WO | 91/17720 | 11/1991 |
| WO | 93/01768 | 2/1993 |
| WO | 95/29640 | 11/1995 |
| WO | 98/14137 | 4/1998 |
| WO | 98/29057 | 7/1998 |
| WO | 99/33414 | 7/1999 |
| WO | 00/41652 | 7/2000 |
| WO | 00/44313 | 8/2000 |
| WO | 00/47136 | 8/2000 |
| WO | 00/47139 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/76510 | 10/2001 |
| WO | 02/22054 | 3/2002 |
| WO | 02/36048 | 5/2002 |
| WO | 02/41789 | 5/2002 |
| WO | 02/43620 | 6/2002 |
| WO | 02/47575 | 6/2002 |
| WO | 02/49540 | 6/2002 |
| WO | 03/003943 | 1/2003 |
| WO | 03/003949 | 1/2003 |
| WO | 03/011195 | 2/2003 |
| WO | 03/030776 | 4/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | 2005/004753 | 1/2005 |
| WO | WO 2005/002466 | 1/2005 |
| WO | 2005/027790 | 3/2005 |
| WO | 2005/046528 | 5/2005 |
| WO | 2006/026371 | 3/2006 |
| WO | 2006-076890 | 7/2006 |
| WO | 2007-013999 | 2/2007 |
| WO | 2008-047354 | 4/2008 |
| WO | 2008/100599 | 8/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/111241 | 9/2009 |

OTHER PUBLICATIONS

U.S. Appl. No. 60/465,141, filed Apr. 2003.
Heinrich RS et al., Ann Biomed Eng. Nov.-Dec. 1996;24(6):685-94. Experimental analysis of fluid mechanical energy losses in aortic valve stenosis: importance of pressure recovery.
Marcus RH et al., Circulation. Sep. 1, 1998;98(9):866-72. Assessment of small-diameter aortic mechanical prostheses: physiological relevance of the Doppler gradient, utility of flow augmentation, and limitations of orifice area estimation.
U.S. Appl. No. 60/845,728, filed Sep 2006.
U.S. Appl. No. 61/192,199, filed Sep. 15, 2008.
Andersen, H.R. et al, "Transluminal implantation of artificial heart valves. Description of a new expandable aortic valve and initial results with implantation by catheter technique in closed chest pigs." Euro. Heart J. (1992) 13:704-708.
Babaliaros, et al., "State of the Art Percutaneous Intervention for the Treatment of Valvular Heart Disease: A Review of the Current Technologies and Ongoing Research in the Field of Percutaneous Heart Valve Replacement and Repair," Cardiology 2007; 107:87-96.
Bailey, "Percutaneous Expandable Prosthetic Valves," In: Topol EJ, ed. Textbook of Interventional Cardiology. vol. II. Second edition. WB Saunders, Philadelphia, 1994:1268-1276.
Block, et al., "Percutaneous Approaches to Valvular Heart Disease," Current Cardiology Reports, vol. 7 (2005) pp. 108-113.
Bonhoeffer, et al, "Percutaneous Insertion of the Pulmonary Valve," Journal of the American College of Cardiology (United States), May 15, 2002, pp. 1664-1669.
Bonhoeffer, et al, "Percutaneous Replacement of Pulmonary Valve in a Right-Ventricle to Pulmonary-Artery Prosthetic Conduit with Valve Dysfunction," Lancet (England), Oct. 21, 2000, pp. 1403-1405.
Bonhoeffer, et al, "Transcatheter Implantation of a Bovine Valve in Pulmonary Position: A Lamb Study," Circulation (United States), Aug. 15, 2000, pp. 813-816.
Boudjemline, et al, "Images in Cardiovascular Medicine. Percutaneous Aortic Valve Replacement in Animals," Circulation (United States), Mar. 16, 2004, 109, p. e161.
Boudjemline, et al, "Is Percutaneous Implantation of a Bovine Venous Valve in the Inferior Vena Cava a Reliable Technique to Treat Chronic Venous Insufficiency Syndrome?" Medical Science Monitor—International Medical Journal of Experimental and Clinical Research (Poland), Mar. 2004, pp. BR61-BR66.
Boudjemline, et al, "Percutaneous Aortic Valve Replacement: Will We Get There?" Heart (British Cardiac Society) (England), Dec. 2001, pp. 705-706.
Boudjemline, et al, "Percutaneous Implantation of a Biological Valve in the Aorta to Treat Aortic Valve Insufficiency—A Sheep Study," Medical Science Monitor—International Medical Journal of Experimental and Clinical Research (Poland), Apr. 2002, pp. BR113-BR116.
Boudjemline, et al, "Percutaneous Implantation of a Biological Valve in Aortic Position: Preliminary Results in a Sheep Study," European Heart Journal, Sep. 22, 2001, p. 630.
Boudjemline, et al, "Percutaneous Implantation of a Valve in the Descending Aorta in Lambs," European Heart Journal (England), Jul. 2002, pp. 1045-1049.
Boudjemline, et al, "Percutaneous Pulmonary Valve Replacement in a Large Right Ventricular Outflow Tract: An Experimental Study," Journal of the American College of Cardiology (United States), Mar. 17, 2004, pp. 1082-1087.
Boudjemline, et al, "Percutaneous Valve Insertion: A New Approach," Journal of Thoracic and Cardiovascular Surgery (United States), Mar. 2003, pp. 741-742.
Boudjemline, et al, "Stent Implantation Combined with a Valve Replacement to Treat Degenerated Right Ventricle to Pulmonary Artery Prosthetic Conduits," European Heart Journal, Sep. 22, 2001, p. 355.
Boudjemline, et al, "Steps Toward Percutaneous Aortic Valve Replacement," Circulation (United States), Feb. 12, 2002, pp. 775-778.
Boudjemline, et al, "The Percutaneous Implantable Heart Valve," Progress in Pediatric Cardiology (Ireland), 2001, pp. 89-93.
Boudjemline, et al, "Transcatheter Reconstruction of the Right Heart," Cardiology in the Young (England), Jun. 2003, pp. 308-311.
Coats, et al, "The Potential Impact of Percutaneous Pulmonary Valve Stent Implantation on Right Ventricular Outflow Tract Re-Intervention," European Journal of Cardio-Thoracic Surgery (England), Apr. 2005, pp. 536-543.

(56) References Cited

OTHER PUBLICATIONS

Cribier, A. et al, "Percutaneous Transcatheter Implantation of an Aortic Valve Prosthesis for Calcific Aortic Stenosis: First Human Case Description," Circulation (2002) 3006-3008.

Davidson et al., "Percutaneous therapies for valvular heart disease," Cardiovascular Pathology 15 (2006) 123-129.

Hanzel, et al., "Complications of percutaneous aortic valve replacement: experience with the Criber-Edwards™ percutaneous heart valve," EuroIntervention Supplements (2006), 1 (Supplement A) A3-A8.

Huber, et al., "Do Valved Stents Compromise Coronary Flow?" Eur. J. Cardiothorac. Surg. 2004;25:754-759.

Khambadkone, "Nonsurgical Pulmonary Valve Replacement: Why, When, and How?" Catheterization and Cardiovascular Interventions—Official Journal of the Society for Cardiac Angiography & Interventions (United States), Jul. 2004, pp. 401-408.

Khambadkone, et al, "Percutaneous Implantation of Pulmonary Valves," Expert Review of Cardiovascular Therapy (England), Nov. 2003, pp. 541-548.

Khambadkone, et al, "Percutaneous Pulmonary Valve Implantation: Early and Medium Term Results," Circulation 108 (17 Supplement), Oct. 28, 2003, p. IV-375.

Khambadkone, et al, "Percutaneous Pulmonary Valve Implantation: Impact of Morphology on Case Selection," Circulation 108 (17 Supplement), Oct. 28, 2003, p. IV-642-IV-643.

Lutter, et al, "Percutaneous Aortic Valve Replacement: An Experimental Study. I. Studies on Implantation," The Journal of Thoracic and Cardiovascular Surgery, Apr. 2002, pp. 768-776.

Lutter, et al, "Percutaneous Valve Replacement: Current State and Future Prospects," Annals of Thoracic Surgery (Netherlands), Dec. 2004, pp. 2199-2206.

Medtech Insight, "New Frontiers in Heart Valve Disease," vol. 7, No. 8 (2005).

Palacios, "Percutaneous Valve Replacement and Repair, Fiction or Reality?" Journal of American College of Cardiology, vol. 44, No. 8 (2004) pp. 1662-1663.

Pelton et al., "Medical Uses of Nitinol," Materials Science Forum vols. 327-328, pp. 63-70 (2000).

Ruiz, "Transcathether Aortic Valve Implantation and Mitral Valve Repair: State of the Art," Pediatric Cardiology, vol. 26, No. 3 (2005).

Saliba, et al, "Treatment of Obstructions of Prosthetic Conduits by Percutaneous Implantation of Stents," Archives des Maldies du Coeur et des Vaisseaux (France), 1999, pp. 591-596.

Webb, et al., "Percutaneous Aortic Valve Implantation Retrograde from the Femoral Artery," Circulation (2006), 113;842-850.

\* cited by examiner

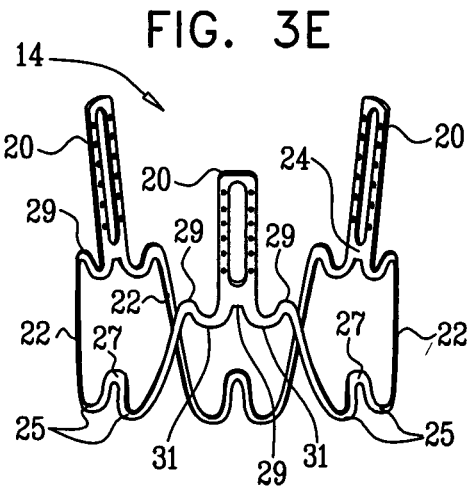
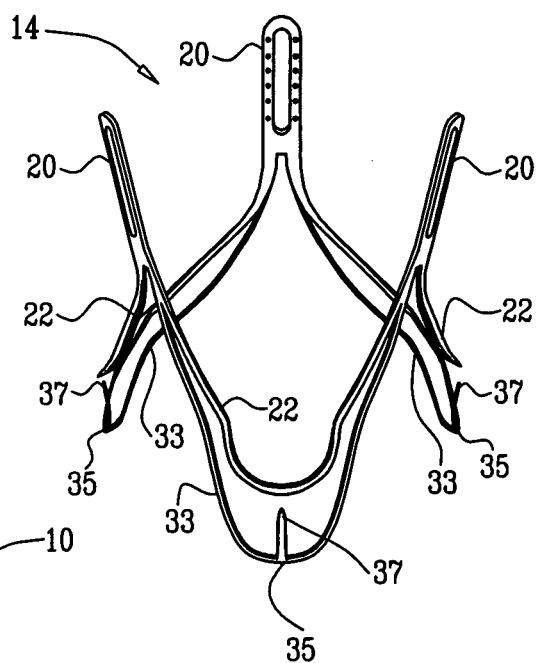
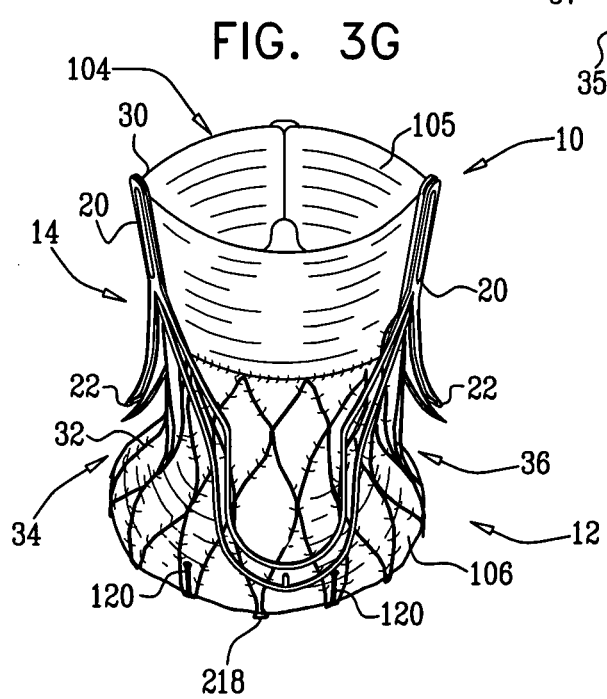

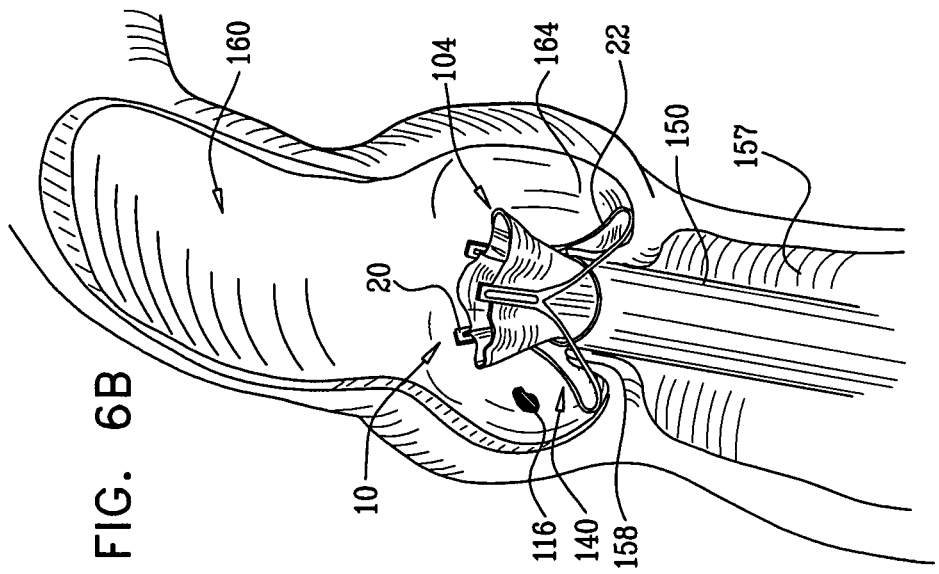
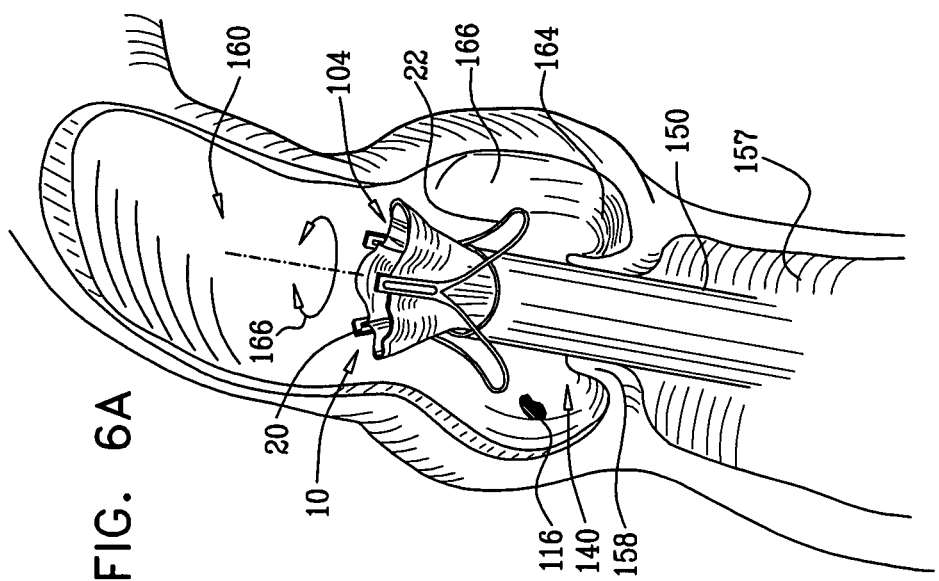

FIG. 7D
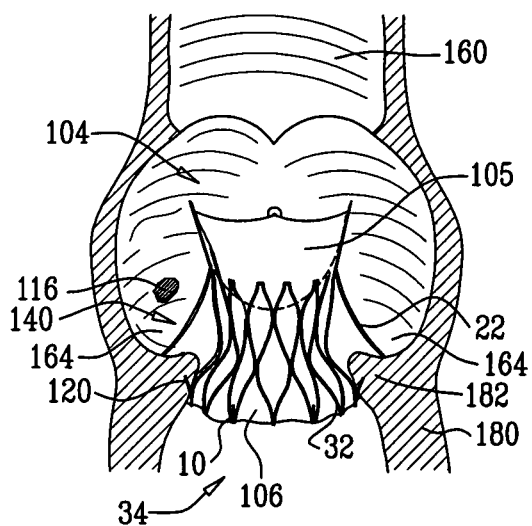
FIG. 7E
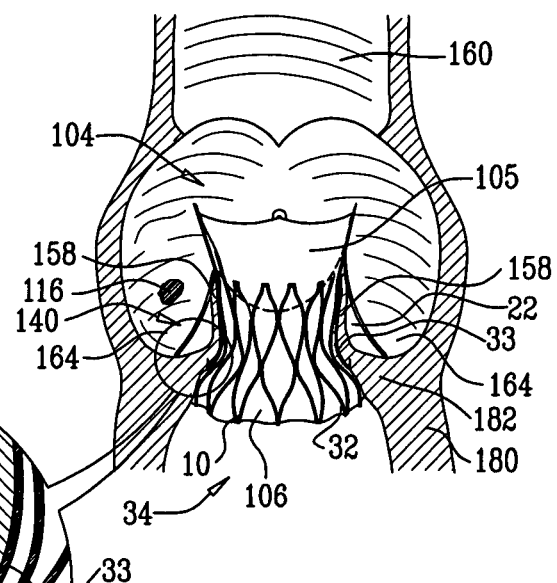
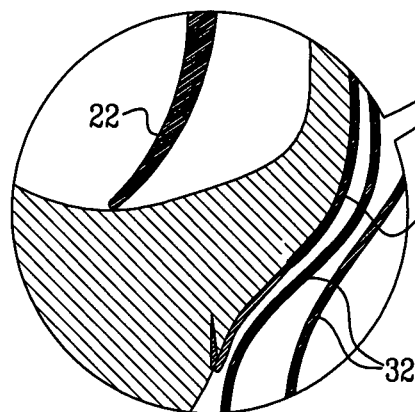
FIG. 8A
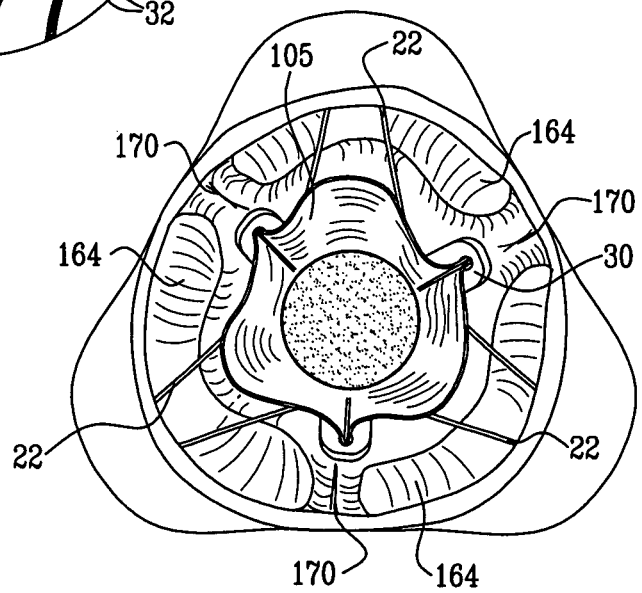

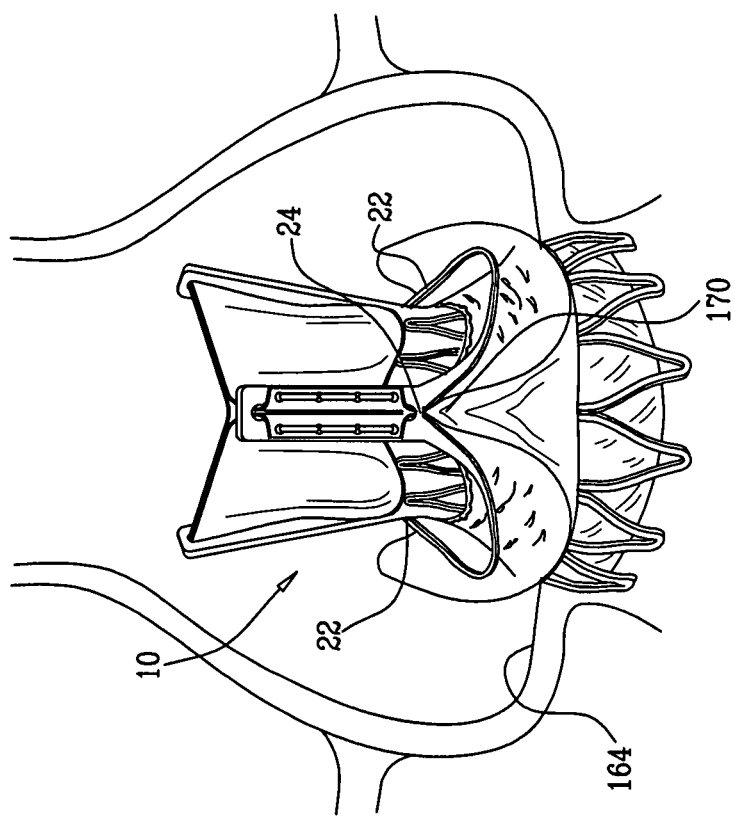
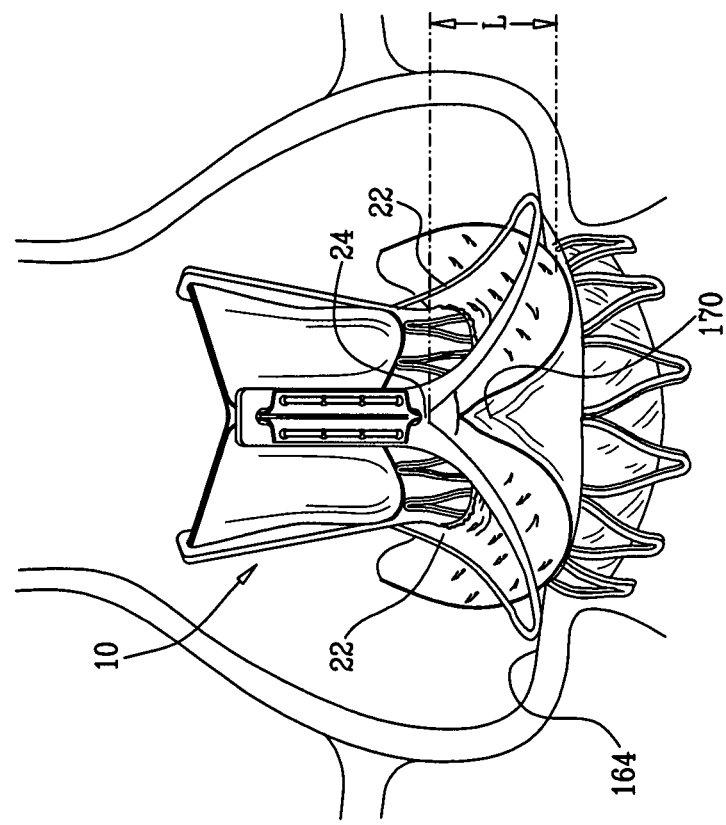

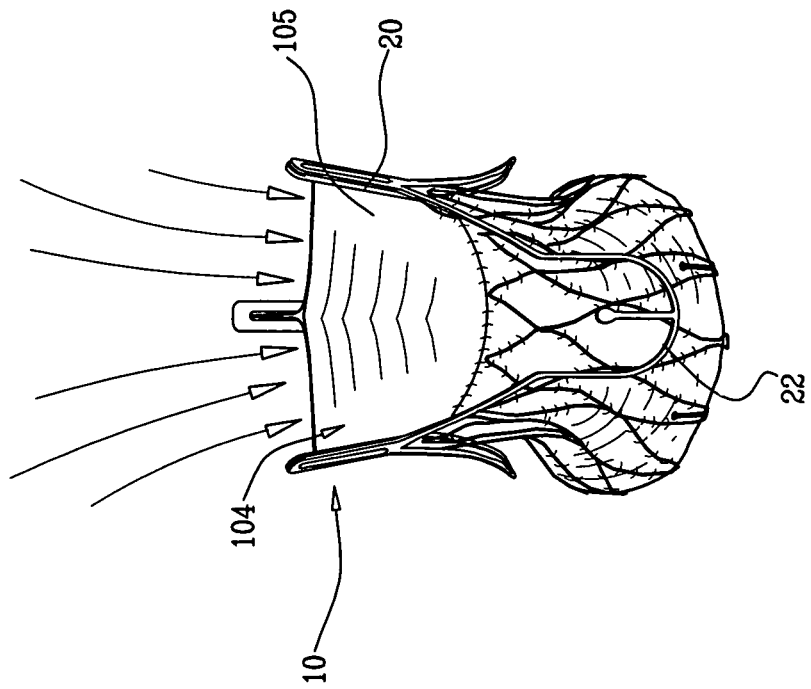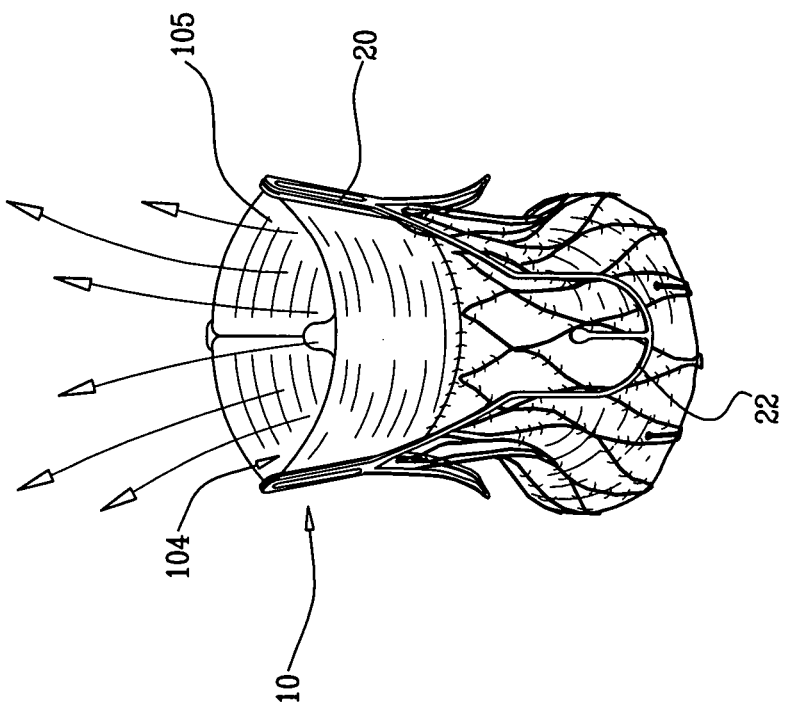

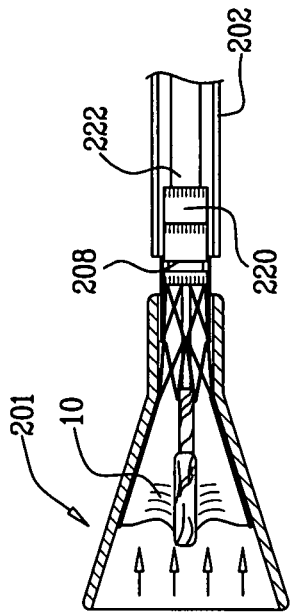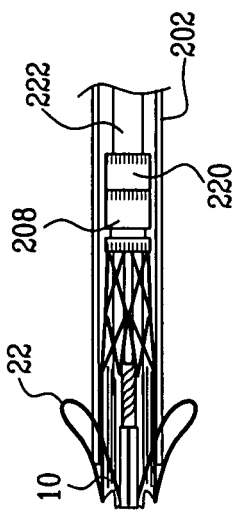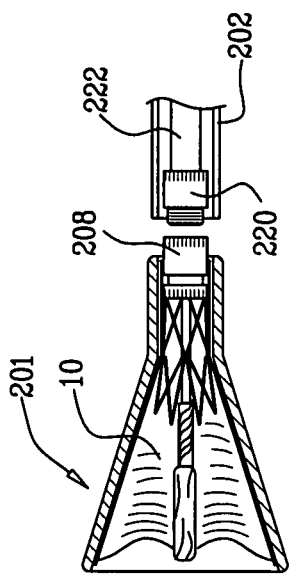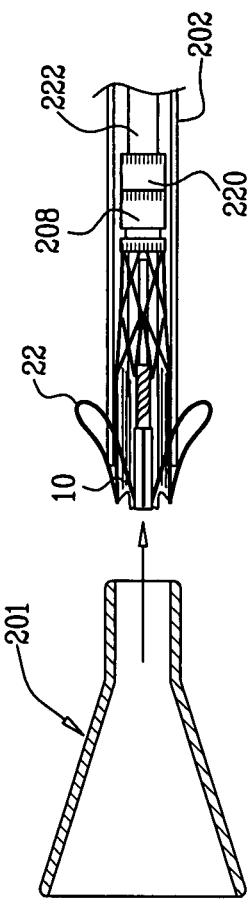

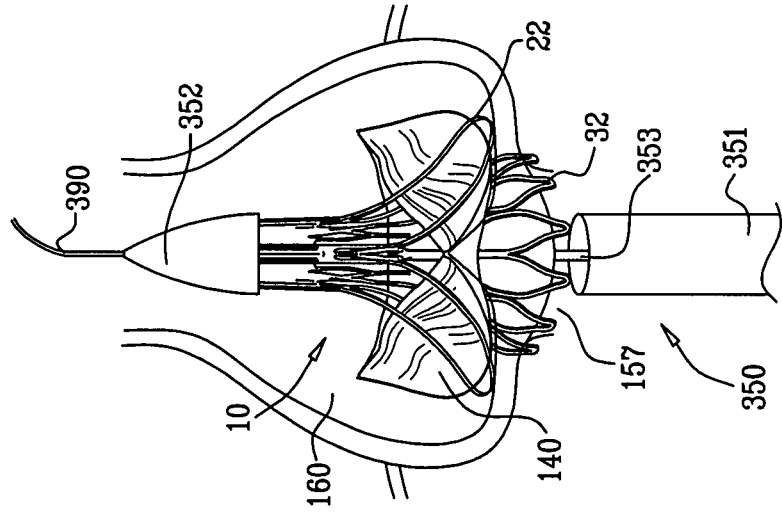
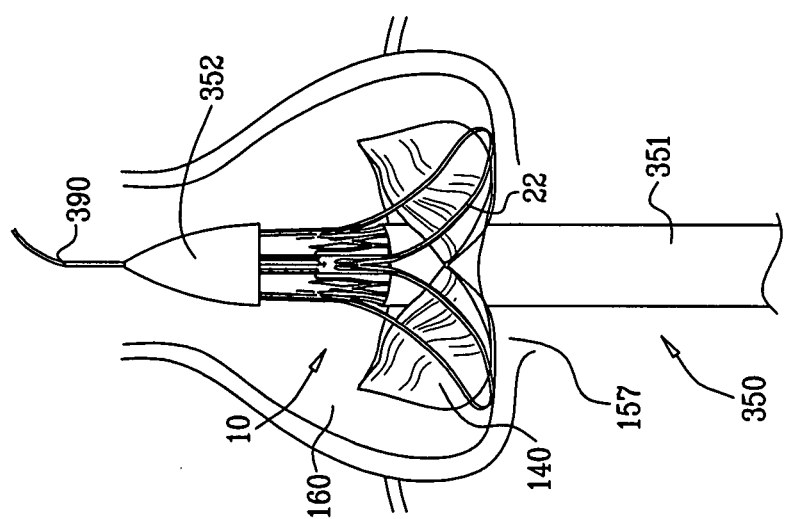

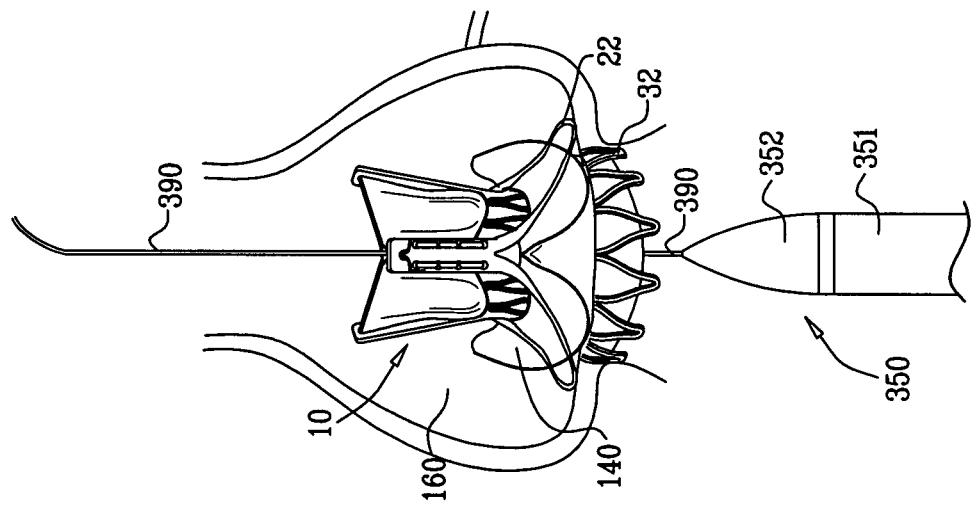
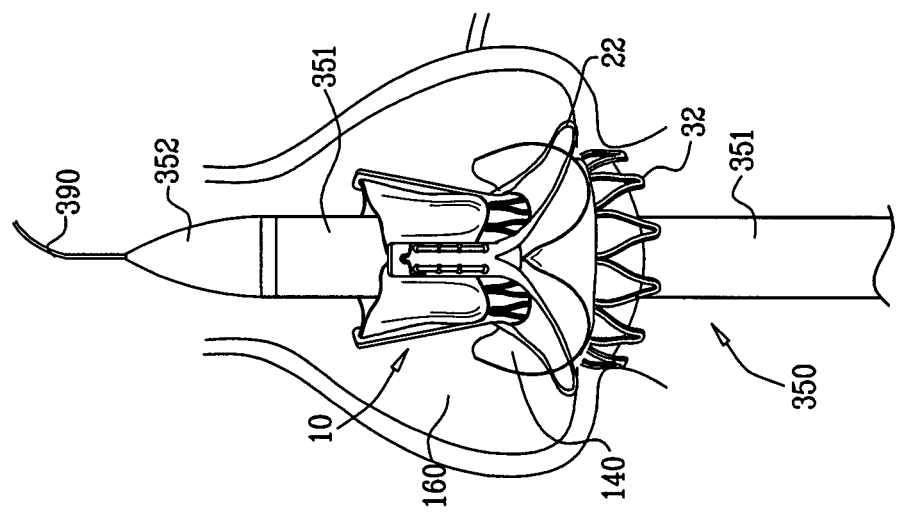
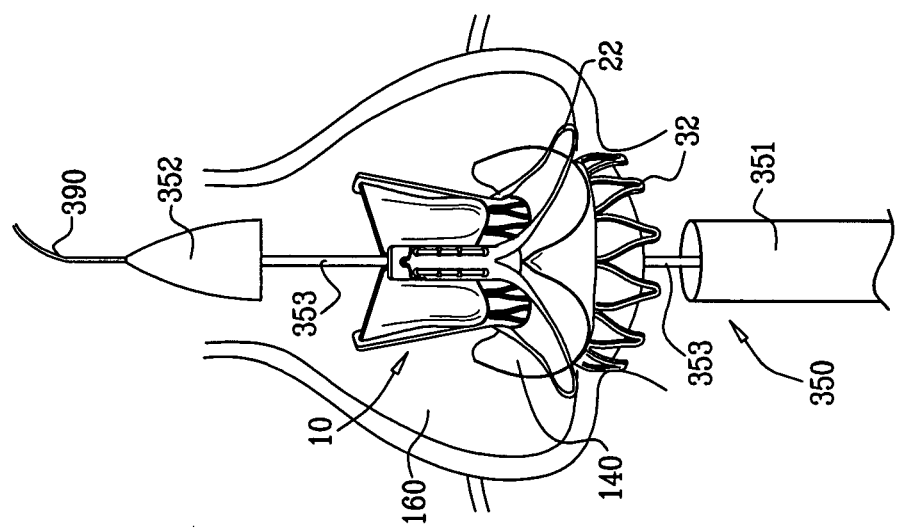

LEAFLET-SENSITIVE VALVE FIXATION MEMBER

CROSS-REFERENCES TO RELATED APPLICATIONS

The present application claims the benefit of U.S. Provisional Application No. 60/845,728, filed Sep. 19, 2006, entitled, "Fixation member for valve," which is assigned to the assignee of the present application and is incorporated herein by reference.

U.S. application Ser. Nos. 11/726,863, 11/728,253, 11/726,893, 11/726,889, and 11/726,875, all of which were filed on Mar. 23, 2007, also claim priority to U.S. Provisional Application No. 60/845,728. U.S. application Ser. Nos. 11/726,863, 11/728,253, 11/726,893, 11/726,889, and 11/726,875, are all assigned to the assignee of the present application, and are incorporated herein by reference in their entirety.

FIELD OF THE INVENTION

The present invention relates generally to prosthetic devices for the treatment of body lumens, and specifically to a valve prosthesis for such body lumens.

BACKGROUND OF THE INVENTION

PCT Publication WO 05/002466 to Schwammenthal et al., which is assigned to the assignee of the present application and is incorporated herein by reference, describes prosthetic devices for treating aortic stenosis.

PCT Publication WO 06/070372 to Schwammenthal et al., which is assigned to the assignee of the present application and is incorporated herein by reference, describes a prosthetic device having a single flow field therethrough, adapted for implantation in a subject, and shaped so as to define a fluid inlet and a diverging section, distal to the fluid inlet.

US Patent Application Publication 2006/0149360 to Schwammenthal et al., which is assigned to the assignee of the present application and is incorporated herein by reference, describes a prosthetic device including a valve-orifice attachment member attachable to a valve in a blood vessel and including a fluid inlet, and a diverging member that extends from the fluid inlet, the diverging member including a proximal end near the fluid inlet and a distal end distanced from the proximal end. A distal portion of the diverging member has a larger cross-sectional area for fluid flow therethrough than a proximal portion thereof.

U.S. Pat. No. 6,730,118 to Spencer et al., which is incorporated herein by reference, describes a valve prosthesis device suitable for implantation in body ducts. The device comprises a support stent, which comprises a deployable construction adapted to be initially crimped in a narrow configuration suitable for catheterization through the body duct to a target location, and adapted to be deployed by exerting substantially radial forces from within by means of a deployment device to a deployed state in the target location; and a valve assembly comprising a flexible conduit having an inlet end and an outlet, made of pliant material attached to the support beams providing collapsible slack portions of the conduit at the outlet. The support stent is provided with a plurality of longitudinally rigid support beams of fixed length. When flow is allowed to pass through the valve prosthesis device from the inlet to the outlet, the valve assembly is kept in an open position, whereas a reverse flow is prevented as the collapsible slack portions of the valve assembly collapse inwardly providing blockage to the reverse flow.

U.S. Pat. No. 7,018,406 to Seguin et al., which is incorporated herein by reference, describes a prosthetic valve assembly for use in replacing a deficient native valve, comprising a replacement valve supported on an expandable valve support. If desired, one or more anchors may be used. The valve support, which entirely supports the valve annulus, valve leaflets, and valve commissure points, is configured to be collapsible for transluminal delivery and expandable to contact the anatomical annulus of the native valve when the assembly is properly positioned. The anchor engages the lumen wall when expanded and prevents substantial migration of the valve assembly when positioned in place. The prosthetic valve assembly is compressible about a catheter, and restrained from expanding by an outer sheath. The catheter may be inserted inside a lumen within the body, such as the femoral artery, and delivered to a desired location, such as the heart. When the outer sheath is retracted, the prosthetic valve assembly expands to an expanded position such that the valve and valve support expand within the deficient native valve, and the anchor engages the lumen wall.

U.S. Pat. No. 7,018,408 to Bailey et al., which is incorporated herein by reference, describes prosthetic cardiac and venous valves and a single catheter device, and minimally invasive techniques for percutaneous and transluminal valvuloplasty and prosthetic valve implantation. The device consists generally of a stent body member, a graft, and valve flaps. The graft is preferably a biocompatible, fatigue-resistant membrane which is capable of endothelialization, and is attached to the stent body member on at least portions of either or both the lumenal and ablumenal surfaces of the stent body member by suturing to or encapsulating stent struts. The valve leaflets are preferably formed by sections of the graft material attached to the stent body member. The stent body member is shaped to include the following stent sections: proximal and distal anchors, a intermediate annular stent section, and at least one valve arm or blood flow regulator struts.

U.S. Pat. No. 6,458,153 and US Patent Application Publication 2003/0023300 to Bailey et al., which are incorporated herein by reference, describe prosthetic cardiac and venous valves and a single catheter device, and minimally invasive techniques for percutaneous and transluminal valvuloplasty and prosthetic valve implantation.

US Patent Application Publication 2004/0186563 to Lobbi, which is incorporated herein by reference, describes a prosthetic heart valve having an internal support frame with a continuous, undulating leaflet frame defined therein. The leaflet frame has three cusp regions positioned at an inflow end intermediate three commissure regions positioned at an outflow end thereof. The leaflet frame may be cloth covered and flexible leaflets attached thereto form occluding surfaces of the valve. The support frame further includes three cusp positioners rigidly fixed with respect to the leaflet frame and located at the outflow end of the support frame intermediate each pair of adjacent commissure regions. The valve is desirably compressible so as to be delivered in a minimally invasive manner through a catheter to the site of implantation. Upon expulsion from catheter, the valve expands into contact with the surrounding native valve annulus and is anchored in place without the use of sutures. In the aortic valve position, the cusp positioners angle outward into contact with the sinus cavities, and compress the native leaflets if they are not excised, or the aortic wall if they are. The support frame may be formed from a flat sheet of nitinol that is bent into a three-dimensional configuration and heat set. A holder having spring-like arms connected to inflow projections of the valve may be used to deliver, reposition and re-collapse the valve, if necessary.

US Patent Application Publication 2003/0130729 to Paniagua et al., which is incorporated herein by reference, describes a percutaneously implantable replacement heart valve device and a method of making same. The replacement heart valve device comprises a stent member made of stainless steel or self-expanding nitinol, and a biological tissue artificial valve means disposed within the inner space of the stent member. An implantation and delivery system has a central part which consists of a flexible hollow tube catheter that allows a metallic wire guide to be advanced inside it. The endovascular stented-valve is a glutaraldehyde fixed bovine pericardium which has two or three cusps that open distally to permit unidirectional blood flow.

US Patent Application Publication 2004/0236411 to Sarac et al., which is incorporated herein by reference, describes a prosthetic valve for replacing a cardiac valve, including an expandable support member and at least two valve leaflets made of a first layer of biological material selected from peritoneal tissue, pleural tissue, or pericardial tissue. A second layer of biological material is attached to the support member. The second layer is also made from peritoneal tissue, pleural tissue, or pericardial tissue. The second layer includes a radially inwardly facing surface that defines a conduit for directing blood flow. The valve leaflets extend across the conduit to permit unidirectional flow of blood through the conduit.

US Patent Application Publication 2005/0075720 to Nguyen et al., which is incorporated herein by reference, describes a method and system for minimally invasive replacement of a valve. The system includes a collapsible valve and anchoring structure, devices and methods for expanding the valve anchoring structure, adhesive means to seal the valve to the surrounding tissue, a catheter-based valve sizing and delivery system, native valve removal means, and a temporary valve and filter assembly to facilitate removal of debris material. The valve assembly comprises a valve and anchoring structure for the valve, dimensioned to fit substantially within the valve sinus.

US Patent Application Publication 2006/0058872 to Salahieh et al., which is incorporated herein by reference, describes an apparatus for endovascularly replacing a patient's heart valve. In some embodiments, the apparatus includes an expandable anchor supporting a replacement valve, the anchor and replacement valve being adapted for percutaneous delivery and deployment to replace the patient's heart valve, the anchor having a braid having atraumatic grasping elements adapted to grasp tissue in a vicinity of the patient's heart valve.

US Patent Application Publication 2005/0137688 to Salahieh et al., which is incorporated herein by reference, describes a method for percutaneously replacing a heart valve of a patient. In some embodiments the method includes the steps of percutaneously delivering a replacement valve and an expandable anchor to a vicinity of the heart valve in an unexpanded configuration; expanding the anchor to a deployed configuration in which the anchor contacts tissue at a first anchor site; repositioning the anchor to a second anchor site; and deploying the anchor at the second anchor site.

US Patent Application Publication 2005/0137690 to Salahieh et al., which is incorporated herein by reference, describes apparatus for endovascularly replacing a patient's heart valve, including: a delivery catheter having a diameter of 21 french or less; an expandable anchor disposed within the delivery catheter; and a replacement valve disposed within the delivery catheter. The invention also includes a method for endovascularly replacing a heart valve of a patient. In some embodiments the method includes the steps of: inserting a catheter having a diameter no more than 21 french into the patient; endovascularly delivering a replacement valve and an expandable anchor to a vicinity of the heart valve through the catheter; and deploying the anchor and the replacement valve.

US Patent Application Publication 2005/0137691 to Salahieh et al., which is incorporated herein by reference, describes apparatus for endovascularly replacing a patient's heart valve, including: a custom-designed anchor; and a replacement valve, wherein the custom-designed anchor is adapted to engage native leaflets of the heart valve, and wherein the anchor and the valve are adapted for in vivo expansion and coupling to one another to form composite apparatus that endovascularly replaces the heart valve. The invention also includes a method for endovascularly replacing a patient's heart valve. In some embodiments the method includes the steps of: providing apparatus comprising an anchor piece and a replacement valve piece; endovascularly delivering the anchor piece to a vicinity of the heart valve in a collapsed delivery configuration; expanding the anchor piece to a deployed configuration; engaging at least one valve leaflet of the heart valve with the anchor piece; endovascularly delivering the replacement valve piece to the vicinity of the heart valve in a collapsed delivery configuration; expanding the replacement valve piece to a deployed configuration; and coupling the valve piece to the anchor piece in vivo to form composite two-piece apparatus that endovascularly replaces the patient's heart valve.

US Patent Application Publication 2005/0137695 to Salahieh et al., which is incorporated herein by reference, describes apparatus for endovascularly replacing a patient's heart valve, including a replacement valve adapted to be delivered endovascularly to a vicinity of the heart valve; an expandable anchor adapted to be delivered endovascularly to the vicinity of the heart valve; and a lock mechanism configured to maintain a minimum amount of anchor expansion.

US Patent Application Publication 2005/0143809 to Salahieh et al., which is incorporated herein by reference, describes techniques for endovascularly replacing a heart valve of a patient. One aspect described is a method including the steps of endovascularly delivering a replacement valve and an expandable anchor to a vicinity of the heart valve in an unexpanded configuration; and applying an external non-hydraulically expanding or non-pneumatically expanding actuation force on the anchor to change the shape of the anchor, such as by applying proximally and/or distally directed force on the anchor using a releasable deployment tool to expand and contract the anchor or parts of the anchor. Another aspect described includes an apparatus including a replacement valve; an anchor; and a deployment tool comprising a plurality of anchor actuation elements adapted to apply a non-hydraulically expanding or non-pneumatically expanding actuation force on the anchor to reshape the anchor.

US Patent Application Publication 2005/0182483 to Osborne et al., which is incorporated herein by reference, describes a venous valve prosthesis having a substantially non-expandable, valve portion comprising a valve-closing mechanism, such as a pair of opposing leaflets; and an anchoring portion, such as one or more self-expanding frames or stents that are expandable to anchor the prosthesis at the implantation site. In one embodiment, the rigid valve portion includes a deposition of material such as pyrolytic carbon to reduce the thrombogenicity of the blood-contacting surfaces. The anchoring portions preferably include a covering, such as a tubular construct of synthetic or collagen-derived material (such as a bioremodelable ECM material), which attaches about the support structure such that blood flow is directed through the valve mechanism as it transitions from the larger diameter anchoring portion to the intermediate, smaller-diameter portion of the prosthesis. In another embodiment, the valve support housing and valve-closing elements are delivered in a collapsed, folded, and/or dissembled state sized for delivery, then manipulated in situ to the second expanded configured following deployment.

US Patent Application Publication 2005/0197695 to Stacchino et al., which is incorporated herein by reference, describes a cardiac-valve prosthesis adapted for percutaneous implantation. The prosthesis includes an armature adapted for deployment in a radially expanded implantation position, the armature including a support portion and an anchor portion, which are substantially axially coextensive with respect to one another. A set of leaflets is coupled to the support portion. The leaflets can be deployed with the armature in the implantation position. The leaflets define, in the implantation position, a flow duct that is selectably obstructable. The anchor portion can be deployed to enable anchorage of the cardiac-valve prosthesis at an implantation site.

US Patent Application Publication 2005/0240200 to Bergheim, which is incorporated herein by reference, describes methods and systems for introducing a delivery device in the heart at or near the apex of the heart, wherein the methods include advancing the prosthesis to a target site, and disengaging the prosthesis from the delivery device at the target site for implantation. Specifically, the valve replacement systems are described for delivering a replacement heart valve to a target site in or near a heart. The valve replacement system comprises a trocar or other suitable device to penetrate the heart at or near the apex of the heart, a delivery member that is movably disposed within the trocar, and a replacement cardiac valve disposed on the delivery member. The delivery member may further comprise mechanical or inflatable expanding members to facilitate implantation of the prosthetic valve at the target site.

US Patent Application Publication 2006/0025857 to Bergheim et al., which is incorporated herein by reference, describes valve prostheses adapted to be initially crimped in a narrow configuration suitable for catheterization through body ducts to a target location, and adapted to be deployed by exerting substantially radial forces from within by means of a deployment device to a deployed state in the target location.

US Patent Application Publication 2006/0025855 to Lashinski et al., which is incorporated herein by reference, describes a cardiovascular prosthetic valve comprising an inflatable body that has at least a first inflatable chamber and a second inflatable chamber that is not in fluid communication with the first inflatable chamber. The inflatable body is configured to form, at least in part, a generally annular ring. A valve is coupled to the inflatable body. The valve is configured to permit flow in a first axial direction and to inhibit flow in a second axial direction opposite to the first axial direction. A first inflation port is in communication with the first inflatable chamber. A second inflation port in communication with the second inflatable chamber.

US Patent Application Publication 2006/0047338 to Jenson et al., which is incorporated herein by reference, describes a cardiac valve having a support frame having a first end member and a second end member opposing the first end member in a substantially fixed distance relationship, and a cover extending over the support frame to allow for unidirectional flow of a liquid through the valve.

US Patent Application Publication 2006/0052867 to Revuelta et al., which is incorporated herein by reference, describes a method for functionally replacing a previously implanted prosthetic heart valve. The method includes positioning a replacement prosthetic heart valve within an internal region defined by the previously implanted prosthetic heart valve. The replacement prosthetic heart valve is then physically docked to the previously implanted prosthetic heart valve. With this technique, the previously implanted prosthetic heart valve serves as a platform for securement of the replacement prosthetic heart valve to the patient's native tissue.

US Patent Application Publication 2006/0074485 to Realyvasquez, which is incorporated herein by reference, describes methods and apparatus for valve repair or replacement. In one embodiment, the apparatus is a valve delivery device comprising a first apparatus and a second apparatus. The first apparatus includes a heart valve support having a proximal portion and a distal portion and a heart valve excisor slidably mounted on said first apparatus. The second apparatus includes a fastener assembly having a plurality of penetrating members mounted to extend outward when the assembly assumes an expanded configuration; and a heart valve prosthesis being releasably coupled to said second apparatus. The first apparatus and second apparatus are sized and configured for delivery to the heart through an opening formed in a femoral blood vessel. The heart valve prosthesis support is movable along a longitudinal axis of the device to engage tissue disposed between the anvil and the valve prosthesis.

US Patent Application Publication 2006/0259136 to Nguyen et al., which is incorporated herein by reference, describes a heart valve prosthesis having a self-expanding multi-level frame that supports a valve body comprising a skirt and plurality of coapting leaflets. The frame transitions between a contracted delivery configuration that enables percutaneous transluminal delivery, and an expanded deployed configuration having an asymmetric hourglass shape. The valve body skirt and leaflets are constructed so that the center of coaptation may be selected to reduce horizontal forces applied to the commissures of the valve, and to efficiently distribute and transmit forces along the leaflets and to the frame. Alternatively, the valve body may be used as a surgically implantable replacement valve prosthesis.

U.S. Pat. No. 7,137,184 to Schreck, which is incorporated herein by reference, describes methods for forming a support frame for flexible leaflet heart valves from a starting blank include converting a two-dimensional starting blank into the three-dimensional support frame. The material may be superelastic, such as NITINOL, and the method may include bending the 2-D blank into the 3-D form and shape setting it. A merely elastic material such as ELGILOY may be used and plastically deformed in stages, possibly accompanied by annealing, to obtain the 3-D shape.

U.S. Pat. No. 6,558,418 to Carpentier et al., which is incorporated herein by reference, describes a highly flexible tissue-type heart valve is disclosed having a structural stent in a generally cylindrical configuration with cusps and commissures that are permitted to move radially. The stent commissures are constructed so that the cusps are pivotably or flexibly coupled together at the commissures to permit relative movement therebetween. The stent may be cloth-covered and may be a single element or may be made in three separate elements for a three cusp valve, each element having a cusp portion and two commissure portions; adjacent commissure portions for each pair of adjacent stent element combining to form the stent commissures. If the stent has separate elements their commissure portions may be pivotably or flexible coupled, or may be designed to completely separate into independent leaflets at bioresorbable couples. The cloth covering may have an outwardly projecting flap that mates with valve leaflets (e.g., pericardial leaflets) along the cusps and commissures. A connecting band may be provided that follows the cusps and commissures and extends outwardly. The valve is connected to the natural tissue along the undulating connecting band using conventional techniques, such as sutures.

U.S. Pat. No. 6,296,662 to Caffey, which is incorporated herein by reference, describes heart valve prosthesis including a heart valve formed of a flexible material. An elongated stent member is provided in the valve and includes terminal ends. A plurality of flexible post members are formed in the stent member. Each post member includes a pair of opposite sides. A crimp collar interconnects the terminal ends of the stent member. The crimp collar is positioned between adjacent post members. A first radius is formed in the stent member between the crimp collar and an adjacent side of each adjacent post member. A plurality of second radii are formed in the stent member between an opposite side of a first one of the adjacent post members and an opposite side of a second one of the adjacent post members. The second radii are greater than each first radius.

The following patents and patent application publication, all of which are incorporated herein by reference, may be of interest:

U.S. Pat. No. 6,312,465 to Griffin et al.
U.S. Pat. No. 5,908,451 to Yeo
U.S. Pat. No. 5,344,442 to Deac
U.S. Pat. No. 5,354,330 to Hanson
US Patent Application Publication 2004/0260389 to Case et al.

SUMMARY OF THE INVENTION

In some embodiments of the present invention, an aortic valve prosthesis for treating a native stenosed valve comprises two portions that are configured to axially sandwich a native valve complex from the aortic (i.e., downstream) and left-ventricular (i.e., upstream) sides thereof, and a collapsible valve that is configured to be open during systole and closed during diastole. The two portions typically include a collapsible inner support structure that serves as a proximal (i.e., upstream) fixation member, and a collapsible outer support structure that serves as a distal (i.e., downstream) fixation member. The distal fixation member is configured to be positioned in an ascending aorta of the subject, and to apply, to an aortic side of the native valve complex, a first axial force directed toward a left ventricle of the subject. The proximal fixation member is configured to be positioned at least partially on the left-ventricular side of the aortic valve, typically extending at least partially into the left ventricular outflow tract (LVOT), and to apply, to a left-ventricular side of the aortic annulus (typically, at the top of the left ventricle), a second axial force directed in a downstream direction (i.e., toward the ascending aorta). Application of the first and second forces couples the prosthesis to the native valve.

In some embodiments of the present invention, the valve prosthesis is configured to treat a native pulmonary valve.

For some applications, the distal fixation member is shaped so as to define engagement arms that are configured to be positioned distal to the native annulus, at least partially within the aortic sinuses, and, for some applications, to apply the first axial force. Typically, for these applications, the distal fixation member is configured to apply the first axial force to the floors of the aortic sinuses.

The valve prosthesis is configured to be placed in the native stenosed valve using a minimally-invasive approach, such as an endovascular or transapical approach. The valve prosthesis is configured to be self-expanding and easy to position, and typically does not require suturing to be held in place. The native valve leaflets typically do not need to be opened to the maximal extent possible, but rather only to the extent which allows insertion of the narrowest part of the valve prosthesis, the diameter of which is typically about 15-20 mm. Placement of the valve prosthesis is thus accompanied by reduced risk of embolism of calcific or thrombotic material dislodged from the valve and coronary occlusion compared to many conventional valve prosthesis implantation procedures.

Unlike some valve prostheses known in the art, the valve prosthesis of some embodiments of the present invention does not rely for fixation on high forces applied outwardly radially against the native valve. Typically, a ratio of (a) the first or second axial force applied by the valve prosthesis to (b) the radial force applied outwardly by the valve prosthesis against the native valve is greater than 1.5:1, e.g., greater than 3:1 or greater than 6:1. For some applications, the valve prosthesis applies a radial force of less than 0.5 pounds (0.23 kilogram-force) outwardly against the native valve, such as less than 0.3 pounds (0.14 kgf), or less than 0.1 pounds (0.045 kgf). For some applications, the valve prosthesis is configured to apply the first axial force with a force of at least 40 g during diastole, and the second axial force with a force of at least 1 g (e.g., at least 5 g) during systole. For some applications, the valve prosthesis is configured to apply the first axial force with a force of no more than 1700 g during diastole.

In other embodiments, the valve prosthesis applies a force outwardly radially against the native valve that is sufficient to aid with fixation of the prosthesis, or sufficient to fixate the prosthesis.

In some embodiments of the present invention, the valve prosthesis applies such outwardly radial forces only to the extent necessary to allow insertion of the prosthesis through the native valve, but not sufficiently to fully open the native leaflets to the maximum extent possible. This level of radial force application, typically in conjunction with the distal fixation member placed upon the aortic side of the native valve leaflets, prevents pushing of the native valve leaflets against the coronary ostia. Additionally, the configuration of the valve prosthesis generally reduces or eliminates leakage around the prosthetic valve, by avoiding damage to the native leaflets. Such damage is avoided because the valve prosthesis typically does not fully open, fold over, or crimp the native leaflets. Instead, the valve prosthesis gently envelops the leaflets between the distal fixation member (e.g., the engagement arms thereof) and the proximal fixation member. Such damage to the native leaflets is also avoided because the valve prosthesis typically does not apply substantial axial force to the native valve commissures. Furthermore, for applications in which the valve prosthesis comprises a bulging proximal skirt, as described hereinbelow, the skirt generally helps reduce leakage around the prosthetic valve.

Typically, the valve prosthesis does not apply an axial force to the tips of the native valve leaflets that would result in shortening of the length of the leaflets, or forced bending, crimping, or folding over of the leaflets. Given the complex composition of the leaflets (fibrous tissue, soft atheroma, and calcifications), such compression might result in the application of shear forces to the leaflets, which might dislodge material and cause an embolism.

Although the valve prosthesis is generally described herein with respect to treating a native aortic valve, in some embodiments the valve prosthesis is used to treat a native pulmonary valve (i.e., the other semilunar valve in the heart), or another native valve of the body, with appropriate modifications to the valve prosthesis.

As used herein, including in the claims, the "native valve complex" includes the native semilunar valve leaflets, the annulus of the valve, the subvalvular tissue on the ventricular side, and the lower half of the semilunar sinuses.

There is therefore provided, in accordance with an embodiment of the present invention, apparatus including a prosthesis for implantation at a native semilunar valve of a native valve complex of a subject, the native valve complex having three semilunar sinuses and three native commissures, the prosthesis including a valve prosthesis support, which includes a support structure including exactly three engagement arms that meet one another at three respective junctures, wherein the engagement arms are shaped so as define three peak complexes at the three respective junctures, and three trough complexes, each of which is between two of the peak complexes, and wherein upon implantation of the prosthesis, each of the engagement arms is at least partially disposed within a respective one of the semilunar sinuses, such that each of the peak complexes is disposed distal to and in rotational alignment with a respective one of the native commissures, and each of the trough complexes is disposed at least partially within the respective one of the semilunar sinuses.

In an embodiment, the native semilunar valve includes a native aortic valve of the subject, the semilunar sinuses include respective aortic sinuses, and upon implantation of the prosthesis, each of the engagement arms is disposed at least partially within the respective one of the aortic sinuses.

In an embodiment, the native semilunar valve includes a native pulmonary valve of the subject, the semilunar sinuses include respective pulmonary sinuses, and upon implantation of the prosthesis, each of the engagement arms is disposed at least partially within the respective one of the pulmonary sinuses.

In an embodiment, the engagement arms are shaped such that each of the peak complexes includes exactly one peak at its respective one of the junctures. In an embodiment, the engagement arms are shaped such that each of the trough complexes includes exactly one trough.

For some applications, the engagement arms are shaped so as to define exactly one trough between each two of the peak complexes. Alternatively, the engagement arms are shaped so as to define a plurality of troughs between each two of the peak complexes.

In an embodiment, the engagement arms are configured to touch respective transitions between the respective semilunar sinuses and respective native leaflet roots of the native valve complex, upon implantation of the prosthesis.

In an embodiment, the prosthesis is configured such that, during implantation of the prosthesis, the peak complexes self-align with the respective native commissures.

For some applications, upon implantation of the prosthesis, each of the peak complexes is disposed in the rotational alignment with the respective one of the native commissures with a rotational offset. Alternatively, upon implantation of the prosthesis, each of the peak complexes is disposed in the rotational alignment with the respective one of the native commissures without a rotational offset.

In an embodiment, the valve prosthesis support, upon implantation of the prosthesis, does not press upon the native commissures of the native semilunar valve. Alternatively, the peak complexes, upon implantation of the prosthesis, touch the respective native commissures of the native semilunar valve at the respective junctures of the engagement arms.

For some applications, the prosthesis is configured to apply a radial force of less than 0.5 pounds outwardly against the native semilunar valve.

In an embodiment, the prosthesis is configured such that any radial force applied by the prosthesis outwardly against the native semilunar valve is insufficient by itself to chronically maintain the prosthesis in position with respect to the native valve complex under conditions of normal cardiac motion.

In an embodiment, the prosthesis is configured, upon implantation thereof, to embrace, such as gently embrace, without squeezing, leaflets of the native semilunar valve.

For some applications, the prosthesis is configured, upon implantation thereof, such that the engagement arms apply a force to distal sides of the leaflets of the native semilunar valve while the engagement arms are generally parallel to the distal sides of the leaflets.

In an embodiment, the valve prosthesis support is configured such that, upon implantation of the prosthesis, the valve prosthesis support does not fold over leaflets of the native semilunar valve. In an embodiment, the valve prosthesis support is configured such that, upon implantation of the prosthesis, the valve prosthesis support does not push leaflets of the native semilunar valve towards respective semilunar sinus floors of the native valve complex. In an embodiment, the prosthesis is configured to less than fully open leaflets of the native valve complex when the prosthesis is implanted at the native valve complex. In an embodiment, the valve prosthesis support is configured to elevate leaflets of the native semilunar valve from within the semilunar sinuses upon implantation of the prosthesis.

In an embodiment, the prosthesis is configured such that, upon implantation at the native valve complex, the engagement arms are aligned by rotation with respective ones of the semilunar sinuses.

In an embodiment, each of the engagement arms includes at least one extension element that extends from the engagement arm, which at least one extension element is configured to engage a sinus floor of the respective one of the semilunar sinuses upon implantation of the prosthesis.

In an embodiment, each of the engagement arms is configured to engage a respective one of the semilunar sinuses upon implantation of the prosthesis. For some applications, each of the engagement arms is configured to firmly engage the respective one of the semilunar sinuses upon implantation of the prosthesis.

In an embodiment, the valve prosthesis support is configured not to apply a force to leaflets of the native semilunar valve sufficient to hold the prosthesis in place.

For some applications, each of the engagement arms is shaped so as to define at least one extension element that extends from the engagement arm, and each of the engagement arms and its respective at least one extension element are configured such that the engagement arm engages, via the at least one extension element, a sinus floor of the respective one of the semilunar sinuses upon implantation of the prosthesis.

For some applications, each of the engagement arms is shaped to define a length, parallel to a longitudinal axis of the prosthesis, between (a) at least one of the junctures and (b) a contact point of one of the engagement arms that meets at the juncture with a sinus floor of the respective one of the semilunar sinuses upon implantation of the prosthesis, which length is greater than 6 mm.

In an embodiment, the prosthesis includes a prosthetic valve including one or more prosthetic leaflets, at least a portion of each of the prosthetic leaflets is configured to assume a closed position during diastole and an open position during systole, and the at least a portion is not directly coupled to any of the engagement arms. For some applications, the prosthetic valve is coupled to the support structure such that at least 50% of an axial length of the prosthetic leaflets is distal to native valve leaflets of the native semilunar valve, upon implantation of the prosthesis. For some applications, the prosthetic valve includes a collapsible pliant material, configured to assume the open and closed positions. For some applications, the valve prosthesis support and the prosthetic valve are configured to define a single flow field through the valve prosthesis support and the prosthetic valve. Alternatively, the valve prosthesis support and the prosthetic valve are configured to define a plurality of flow fields through the valve prosthesis support and the prosthetic valve.

In an embodiment, the support structure includes exactly three commissural posts, to which the junctures of the engagement arms are respectively attached. For some applications, upon implantation of the prosthesis, the commissural posts are rotationally aligned with respective ones of the native commissures.

In an embodiment, the engagement arms are shaped so as to flare out laterally to an angle with respect to a central axis of the prosthesis. In an embodiment, the engagement arms conform to a shape of a semilunar root of the native valve complex when the engagement arms are flared out. In an embodiment, the engagement arms are shaped so as to curve outwards laterally. In an embodiment, a shape of at least one of the engagement arms is generally characterized by a function $z''(r) \geq 0$, where z is a height of any given point on the at least one engagement arm measured along a longitudinal axis of the prosthesis, and r is a distance from the longitudinal axis to the given point. For some applications, the shape is generally characterized by the function $z''(r) > 0$.

In an embodiment, the support structure is configured to serve as a distal fixation member, the valve prosthesis support includes a proximal fixation member, and the proximal fixation member and the engagement arms of the distal fixation member are configured to axially sandwich the native valve complex from ventricular and downstream sides thereof, respectively, upon implantation of the prosthesis.

In an embodiment, the engagement arms are configured to be disposed, during an implantation procedure, at least partially within the respective ones of the semilunar sinuses before the proximal fixation member is positioned at least partially on the ventricular side of the native valve complex, such that the arms prevent leaflets of the native valve complex from opening more than a predetermined desired amount, the opening being because of force applied by the proximal fixation member to the leaflets.

In an embodiment, the proximal fixation member is configured to be positioned at least partially in a ventricle of the subject upon implantation of the prosthesis.

In an embodiment, the proximal fixation member is shaped so as to define at least one barb configured to apply a barb force to the ventricular side of the native valve complex. For some applications, the at least one barb is configured to pierce the ventricular side of the native valve complex. Alternatively, the at least one barb is configured to protrude into tissue of the ventricular side of the native valve complex, without piercing the tissue. In an embodiment, the distal fixation member is shaped so as to define at least one mating barb, and the at least one barb of the proximal fixation member is configured to engage the at least one mating barb, so as to help hold the prosthesis in place.

In an embodiment, the proximal and distal fixation members are collapsible. For some applications, the distal fixation member is configured to be positioned, during an implantation procedure, in a downstream artery while collapsed, and to be expanded before the proximal fixation member is positioned at least partially on the ventricular side of the native valve complex, the downstream artery selected from the group consisting of: an ascending aorta, and a pulmonary trunk. For some applications, the apparatus includes at least one tube selected from the group consisting of: an overtube and a trocar, and the proximal and distal fixation members are configured to be stored in the selected tube while collapsed, and to expand upon being deployed from the selected tube.

In an embodiment, the proximal fixation member includes an inner support structure, and the distal fixation member includes an outer support structure that is placed partially over the inner support structure. For some applications, the inner and outer support structures are configured to be coupled to one another during an implantation procedure.

In an embodiment, the outer support structure is shaped so as to define a plurality of distal diverging strut supports, from which the engagement arms extend radially outward. In an embodiment, the prosthesis is configured such that, upon implantation at the native valve complex, the strut supports are aligned with the respective native commissures. In an embodiment, the inner support structure is shaped so as to define a plurality of distal diverging inner struts.

In an embodiment, the inner support structure is shaped so as to define a bulging proximal skirt, a proximal portion of which is configured to apply an axial force directed toward a downstream artery selected from the group consisting of: an ascending aorta, and a pulmonary trunk. For some applications, the prosthesis includes a graft covering that covers at least a portion of the skirt.

In an embodiment, the inner support structure is shaped so as to define a plurality of distal diverging inner struts, and the skirt extends from the inner struts.

In an embodiment, the outer support structure is shaped so as to define a plurality of distal diverging strut supports, from which the engagement arms extend radially outward, and each of the strut supports is positioned over a respective one of the inner struts.

In an embodiment, the engagement arms are positioned over a portion of the skirt.

In an embodiment, the prosthesis includes a valve including a collapsible pliant material, configured to assume a closed position during diastole and an open position during systole, and the pliant material includes a plurality of segments, at least two of which are coupled together by one of the strut supports and its respective one of the inner struts.

There is further provided, in accordance with an embodiment of the present invention, apparatus including a prosthesis for implantation at a native aortic valve of a native valve complex of a subject, the native valve complex having exactly two aortic sinuses and two native commissures, the prosthesis including a valve prosthesis support, which includes a support structure including exactly two engagement arms that meet one another at two respective junctures, wherein the engagement arms are shaped so as define two peak complexes at the two respective junctures, and two trough complexes, each of which is between the peak complexes, and wherein upon implantation of the prosthesis, each of the engagement arms is at least partially disposed within a respective one of the aortic sinuses, such that each of the peak complexes is disposed distal to and in rotational alignment with a respective one of the native commissures, and each of the trough complexes is disposed at least partially within the respective one of the aortic sinuses.

In an embodiment, the engagement arms are shaped such that each of the peak complexes includes exactly one peak at its respective one of the junctures. In an embodiment, the engagement arms are shaped such that each of the trough complexes includes exactly one trough.

In an embodiment, each of the engagement arms is configured to engage a respective one of the aortic sinuses upon implantation of the prosthesis.

There is still further provided, in accordance with an embodiment of the present invention, apparatus including a prosthesis for implantation at a native semilunar valve of a native valve complex of a subject, the prosthesis including:

a prosthetic valve including one or more prosthetic leaflets configured to assume a closed position during diastole and an open position during systole; and a valve prosthesis support, coupled to the prosthetic valve, and configured to engage one or more semilunar sinuses of the native semilunar valve site, such that at least 50% of an axial length of the prosthetic leaflets is distal to native valve leaflets of the native semilunar valve.

In an embodiment, the native semilunar valve includes a native aortic valve, the semilunar sinuses include respective aortic sinuses, and the valve prosthetic support is configured to engage the one or more aortic sinuses. In an embodiment, the native semilunar valve includes a native pulmonary valve, the semilunar sinuses include respective pulmonary sinuses, and the valve prosthetic support is configured to engage the one or more pulmonary sinuses.

There is yet further provided, in accordance with an embodiment of the present invention, a method for implanting a prosthesis at a native semilunar valve of a native valve complex of a subject, the native valve complex having three semilunar sinuses and three native commissures, the method including:

providing the prosthesis including a valve prosthesis support, which valve prosthesis support includes a support structure including exactly three engagement arms that meet one another at three respective junctures, and the engagement arms are shaped so as define three peak complexes at the three respective junctures, and three trough complexes, each of which is between two of the peak complexes; and implanting the prosthesis such that each of the engagement arms is at least partially disposed within a respective one of the semilunar sinuses, each of the peak complexes is disposed distal to and in rotational alignment with a respective one of the native commissures, and each of the trough complexes is disposed at least partially within the respective one of the semilunar sinuses.

In an embodiment, the native semilunar valve includes a native aortic valve of the subject, the semilunar sinuses include respective aortic sinuses, and implanting includes implanting the prosthesis such that each of the engagement arms is disposed at least partially within the respective one of the aortic sinuses.

In an embodiment, the native semilunar valve includes a native pulmonary valve of the subject, the semilunar sinuses include respective pulmonary sinuses, and implanting includes implanting the prosthesis such that each of the engagement arms is disposed at least partially within the respective one of the pulmonary sinuses.

In an embodiment, the prosthesis is configured such that, during implantation of the prosthesis, the peak complexes self-align with the respective native commissures.

In an embodiment, implanting includes implanting the prosthesis such that the prosthesis embraces, such as gently embraces, without squeezing, leaflets of the native semilunar valve. In an embodiment, implanting includes implanting the prosthesis such that the valve prosthesis support does not fold over leaflets of the native semilunar valve.

In an embodiment, implanting includes implanting the prosthesis such that the engagement arms touch respective floors of the respective semilunar sinuses.

In an embodiment, implanting includes causing the prosthesis to self-align with respect to the native semilunar valve site by gently rotating the prosthesis.

In an embodiment, the support structure is configured to serve as a distal fixation member, the valve prosthesis support includes a proximal fixation member, and implanting includes implanting the prosthesis such that the proximal fixation member and the engagement arms of the distal fixation member axially sandwich the native valve complex from ventricular and downstream sides thereof, respectively.

In an embodiment, implanting includes:

positioning the distal fixation member in a downstream artery while the distal fixation member is collapsed;

expanding the distal fixation member; and thereafter, positioning the proximal fixation member at least partially on the ventricular side of the native valve complex, the downstream artery selected from the group consisting of: an ascending aorta, and a pulmonary trunk.

In an embodiment, implanting includes:

storing the proximal and distal fixation members in at least one tube selected from the group consisting of: an overtube and a trocar, while the proximal and distal fixation members are collapsed; and deploying the proximal and distal fixation members from the selected tube such that the proximal and distal fixation members expand.

In an embodiment, the proximal fixation member includes an inner support structure, the distal fixation member includes an outer support structure that is placed partially over the inner support structure, and implanting includes configuring the inner and outer support structures to one another during the implanting.

There is additionally provided, in accordance with an embodiment of the present invention, a method for implanting a prosthesis at a native aortic valve of a native valve complex of a subject, the native valve complex having exactly two aortic sinuses and two native commissures, the method including:

providing the prosthesis including a valve prosthesis support, which valve prosthesis support includes a support structure including exactly two engagement arms that meet one another at two respective junctures, and the engagement arms are shaped so as define two peak complexes at the two respective junctures, and two trough complexes, each of which is between the peak complexes; and implanting the prosthesis such that each of the engagement arms is at least partially disposed within a respective one of the aortic sinuses, each of the peak complexes is disposed distal to and in rotational alignment with a respective one of the native commissures, and each of the trough complexes is disposed at least partially within the respective one of the aortic sinuses.

There is still additionally provided, in accordance with an embodiment of the present invention, a method for implanting a prosthesis at a native semilunar valve of a native valve complex of a subject, the method including:

providing the prosthesis including a prosthetic valve including one or more prosthetic leaflets configured to assume a closed position during diastole and an open position during systole, and a valve prosthesis support, coupled to the prosthetic valve; and implanting the prosthesis such that the valve prosthesis support engages one or more semilunar sinuses of the native semilunar valve site, such that at least 50% of an axial length of the prosthetic leaflets is distal to native valve leaflets of the native semilunar valve.

In an embodiment, the native semilunar valve includes a native aortic valve, and implanting the prosthesis includes implanting the prosthesis such that the valve prosthesis support engages the one or more semilunar sinuses of the native aortic valve.

In an embodiment, the native semilunar valve includes a native pulmonary valve, and implanting the prosthesis includes implanting the prosthesis such that the valve prosthesis support engages the one or more semilunar sinuses of the native pulmonary valve.

In an embodiment, implanting the prosthesis includes implanting the prosthesis such that the prosthesis leaflets do not engage the semilunar sinuses.

In an embodiment, implanting the prosthesis includes causing the prosthesis to self-align with respect to the native semilunar valve site by gently rotating the prosthesis.

There is yet additionally provided, in accordance with an embodiment of the present invention, a method, including:

placing a semilunar valve prosthesis at a native semilunar valve site, which prosthesis includes a prosthetic valve including one or more prosthetic leaflets configured to assume a closed position during diastole and an open position during systole; and engaging a portion of the semilunar valve prosthesis, other than the prosthetic leaflets, with one or more semilunar sinuses of the native semilunar valve site, such that at least 50% of an axial length of the prosthetic leaflets is distal to native valve leaflets of a native semilunar valve of the native semilunar valve site.

In an embodiment, the native semilunar valve site includes a native aortic valve site, the semilunar sinuses include respective aortic sinuses, the semilunar valve prosthesis includes an aortic valve prosthesis, placing includes placing the aortic valve prosthesis at the native aortic valve site, and engaging includes engaging the portion of the aortic valve prosthesis with the one or more aortic sinuses.

In an embodiment, the native semilunar valve site includes a native pulmonary valve site, the semilunar sinuses include respective pulmonary sinuses, the semilunar valve prosthesis includes a pulmonary valve prosthesis, placing includes placing the pulmonary valve prosthesis at the native pulmonary valve site, and engaging includes engaging the portion of the pulmonary valve prosthesis with the one or more pulmonary sinuses.

In an embodiment, engaging includes causing the semilunar valve prosthesis to self-align with respect to the native semilunar valve site by gently rotating the semilunar valve prosthesis.

There is also provided, in accordance with an embodiment of the present invention, apparatus including a prosthesis for implantation at a native semilunar valve of a native valve complex of a subject, the native valve complex having semilunar sinuses, the prosthesis including a valve prosthesis support, which includes a support structure including at least two engagement arms, wherein, upon implantation of the prosthesis, each of the engagement arms is at least partially disposed within a respective one of the semilunar sinuses, and wherein a shape of at least one of the engagement arms is generally characterized by a function $z''(r) >= 0$, where z is a height of any given point on the at least one engagement arm measured along a longitudinal axis of the prosthesis, and r is a distance from the longitudinal axis to the given point.

For some applications, the shape is generally characterized by the function $z''(r) > 0$.

In an embodiment, the native semilunar valve includes a native aortic valve of the subject, the semilunar sinuses include respective aortic sinuses, and, upon implantation of the prosthesis, each of the engagement arms is disposed at least partially within the respective one of the aortic sinuses.

In an embodiment, the native semilunar valve includes a native pulmonary valve of the subject, the semilunar sinuses include respective pulmonary sinuses, and, upon implantation of the prosthesis, each of the engagement arms is at least partially disposed within the respective one of the pulmonary sinuses.

For some applications, each of the engagement arms includes at least one extension element that extends from the engagement arm, which at least one extension element is configured to engage a sinus floor of the respective one of the semilunar sinuses upon implantation of the prosthesis.

In an embodiment, the support structure includes exactly three engagement arms.

In an embodiment, the prosthesis is configured, upon implantation thereof, to embrace, such as gently embrace, without squeezing, leaflets of the native semilunar valve. In an embodiment, the valve prosthesis support is configured such that, upon implantation of the prosthesis, the valve prosthesis support does not fold over leaflets of the native semilunar valve.

In an embodiment, the support structure is configured to serve as a distal fixation member, the valve prosthesis support includes a proximal fixation member, and the proximal fixation member and the engagement arms of the distal fixation member are configured to axially sandwich the native valve complex from ventricular and downstream sides thereof, respectively, upon implantation of the prosthesis.

In an embodiment, each of the engagement arms is configured to engage a respective one of the semilunar sinuses upon implantation of the prosthesis.

For some applications, each of the engagement arms is shaped so as to define at least one extension element that extends from the engagement arm, and each of the engagement arms and its respective at least one extension element are configured such that the engagement arm engages, via the at least one extension element, a sinus floor of the respective one of the semilunar sinuses upon implantation of the prosthesis.

For some applications, each of the engagement arms is shaped to define a length, parallel to a longitudinal axis of the prosthesis, between (a) at least one of the junctures and (b) a contact point of one of the engagement arms that meets at the juncture with a sinus floor of the respective one of the semilunar sinuses upon implantation of the prosthesis, which length is greater than 6 mm.

In an embodiment, the prosthesis includes a prosthetic valve including one or more prosthetic leaflets, at least a portion of each of the prosthetic leaflets is configured to assume a closed position during diastole and an open position during systole, and the at least a portion is not directly coupled to any of the engagement arms. For some applications, the prosthetic valve is coupled to the support structure such that at least 50% of an axial length of the prosthetic leaflets is distal to native valve leaflets of the native semilunar valve, upon implantation of the prosthesis.

In an embodiment, the engagement arms are configured to touch respective floors of the respective semilunar sinuses, upon implantation of the prosthesis.

In an embodiment, the engagement arms are configured to firmly engage the respective semilunar sinuses, upon implantation of the prosthesis.

There is further provided, in accordance with an embodiment of the present invention, apparatus including a prosthesis for implantation at a native semilunar valve of a native valve complex of a subject, the native valve complex having semilunar sinuses, the prosthesis including a valve prosthesis support, which includes a support structure including at least two engagement arms, wherein, upon implantation of the prosthesis, each of the engagement arms is at least partially disposed within a respective one of the semilunar sinuses, and wherein a shape of at least one of the engagement arms is generally upwardly concave.

There is still further provided, in accordance with an embodiment of the present invention, a method for implanting a prosthesis at a native semilunar valve of a native valve complex of a subject, the native valve complex having semilunar sinuses, the method including:

providing the prosthesis including a valve prosthesis support, which valve prosthesis support includes a support structure including at least two engagement arms, and a shape of at least one of the engagement arms is generally characterized by a function $z''(r) >= 0$, where z is a height of any given point on the at least one engagement arm measured along a longitudinal axis of the prosthesis, and r is a distance from the longitudinal axis to the given point; and implanting the prosthesis such that each of the engagement arms is at least partially disposed within a respective one of the semilunar sinuses.

In an embodiment, implanting includes implanting the prosthesis such that each of the engagement arms is configured to engage a respective one of the semilunar sinuses.

There is yet further provided, in accordance with an embodiment of the present invention, a method for implanting a prosthesis at a native semilunar valve of a native valve complex of a subject, the native valve complex having semilunar sinuses, the method including:

providing the prosthesis including a valve prosthesis support, which valve prosthesis support includes a support structure including at least two engagement arms, and a shape of at least one of the engagement arms is generally upwardly concave; and implanting the prosthesis such that each of the engagement arms is at least partially disposed within a respective one of the semilunar sinuses.

There is additionally provided, in accordance with an embodiment of the present invention, a method including:

providing a semilunar valve prosthesis; and implanting the prosthesis without using any imaging techniques.

In an embodiment, providing the semilunar valve prosthesis includes providing an aortic valve prosthesis. In an embodiment, providing the semilunar valve prosthesis includes providing a pulmonary valve prosthesis.

In an embodiment, implanting includes: placing the prosthesis at a semilunar valve site; and causing the prosthesis to self-align with respect to the site by gently rotating the prosthesis.

In an embodiment, implanting the prosthesis includes determining a correct rotational disposition of the prosthesis with respect to a semilunar valve site based on tactile feedback.

There is still additionally provided, in accordance with an embodiment of the present invention, a method including:

providing a semilunar valve prosthesis;

placing the prosthesis in a body of a subject; and determining a correct rotational disposition of the prosthesis with respect to a semilunar valve site based on tactile feedback.

In an embodiment, providing the semilunar valve prosthesis includes providing an aortic valve prosthesis. In an embodiment, providing the semilunar valve prosthesis includes providing a pulmonary valve prosthesis.

In an embodiment, placing the prosthesis includes placing the prosthesis without using any imaging techniques.

There is yet additionally provided, in accordance with an embodiment of the present invention, a method including:

placing a semilunar valve prosthesis at a native semilunar valve site; and causing the prosthesis to self-align with respect to the site by gently rotating the valve prosthesis.

In an embodiment, the semilunar valve prosthesis includes an aortic valve prosthesis, the native semilunar valve site includes a native aortic valve site, and placing includes placing the aortic valve prosthesis at the native aortic valve site. In an embodiment, the semilunar valve prosthesis includes a pulmonary valve prosthesis, the native semilunar valve site includes a native pulmonary valve site, and placing includes placing the pulmonary valve prosthesis at the native pulmonary valve site.

In an embodiment, causing the prosthesis to self-align includes moving the prosthesis in an axial direction defined with respect to an axis of a downstream artery, while gently rotating the prosthesis, the downstream artery selected from the group consisting of: an ascending aorta, and a pulmonary trunk.

In an embodiment, gently rotating the prosthesis includes moving the prosthesis in a proximal direction such that contact of the prosthesis with tissue of the native semilunar valve site causes the rotating.

In an embodiment, placing the prosthesis and causing the prosthesis to self-align include placing the prosthesis and causing the prosthesis to self-align without using any imaging techniques.

In an embodiment, causing the prosthesis to self-align includes verifying that the prosthesis is properly aligned with respect to the semilunar valve site by attempting to rotate the prosthesis with respect to the semilunar valve site.

In an embodiment, the prosthesis is shaped so as to define one or more proximal engagement arms that are configured to be positioned at least partially within respective semilunar sinuses of the native semilunar valve site, and causing the prosthesis to self-align includes causing the engagement arms to self-align with respect to the respective semilunar sinuses.

In an embodiment, gently rotating the prosthesis includes moving the prosthesis in a proximal direction such that contact of one or more of the engagement arms with tissue of the native semilunar valve site causes the rotating.

In an embodiment, causing the prosthesis to self-align includes verifying that the engagement arms are properly placed with respect to the semilunar valve site by attempting to rotate the engagement arms with respect to the semilunar valve site.

There is also provided, in accordance with an embodiment of the present invention, a method, including:

placing a semilunar valve prosthesis at a native semilunar valve site, the prosthesis shaped so as to define one or more proximal engagement arms;

attempting to position the engagement arms at least partially within respective semilunar sinuses of the native semilunar valve site; and verifying that the engagement arms are properly placed with respect to the semilunar valve site by attempting to rotate the engagement arms with respect to the semilunar valve site.

In an embodiment, the semilunar valve prosthesis includes an aortic valve prosthesis, the native semilunar valve site includes a native aortic valve site, and placing includes placing the aortic valve prosthesis at the native aortic valve site.

In an embodiment, the semilunar valve prosthesis includes a pulmonary valve prosthesis, the native semilunar valve site includes a native pulmonary valve site, and placing includes placing the pulmonary valve prosthesis at the native pulmonary valve site.

There is further provided, in accordance with an embodiment of the present invention, apparatus including a prosthesis for implantation at a native semilunar valve of a native valve complex of a subject, the prosthesis including a support structure, which is configured such that a correct rotational disposition of the prosthesis with respect to the native semilunar valve can be determined based on tactile feedback.

There is still further provided, in accordance with an embodiment of the present invention, apparatus including a prosthesis for implantation at a native semilunar valve of a native valve complex of a subject, the native valve complex having semilunar sinuses and native commissures, the prosthesis including:

a distal fixation member, configured to be positioned in a downstream artery of the subject selected from the group consisting of: an ascending aorta, and a pulmonary trunk, and shaped so as to define exactly three proximal engagement arms that are configured to be positioned at least partially within respective ones of the semilunar sinuses, and, in combination, to apply, to tissue that defines the semilunar sinuses, a first axial force directed toward a ventricle of the subject; and a proximal fixation member coupled to the distal fixation member, the proximal fixation member configured to be positioned at least partially on a ventricular side of the native semilunar valve, and to apply, to the ventricular side of the native valve complex, a second axial force directed toward the downstream artery, such that application of the first and second forces couples the prosthesis to the native valve complex.

In an embodiment, the native semilunar valve includes a native aortic valve, and the downstream artery includes the ascending aorta, the semilunar sinuses include respective aortic sinuses, and the distal fixation member is configured to be positioned in the ascending aorta, and the proximal engagement arms are configured to be positioned at least partially within the respective aortic sinuses.

In an embodiment, the native semilunar valve includes a native pulmonary valve, and the downstream artery includes the pulmonary trunk, and the semilunar sinuses include respective pulmonary sinuses, and the distal fixation member is configured to be positioned in the pulmonary trunk, and the proximal engagement arms are configured to be positioned at least partially within the respective pulmonary sinuses.

In an embodiment, the distal and proximal fixation members are configured to couple the prosthesis to the native valve complex by axially sandwiching the native valve complex from a downstream side and the ventricular side thereof, upon implantation of the prosthesis.

In an embodiment, the distal fixation member does not press upon the native commissures upon implantation of the prosthesis.

In an embodiment, the prosthesis is configured to apply a radial force of less than 0.5 pounds outwardly against the native semilunar valve. In an embodiment, the prosthesis is configured to apply the first axial force with a force of at least 40 g during diastole. In an embodiment, the prosthesis is configured to apply the second axial force with a force of at least 1 g during systole.

In an embodiment, the prosthesis is configured such that any radial force applied by the prosthesis outwardly against the native semilunar valve is insufficient by itself to chronically maintain the prosthesis in position with respect to the native valve complex under conditions of normal cardiac motion.

In an embodiment, the prosthesis is configured, upon implantation thereof, to embrace, such as gently embrace, without squeezing, leaflets of the native semilunar valve.

In an embodiment, the distal fixation member is configured to be positioned in the downstream artery during an implantation procedure before the proximal fixation member is positioned at least partially on the ventricular side of the native valve complex.

In an embodiment, the distal fixation member is configured such that it does not fold over leaflets of the native semilunar valve upon implantation of the prosthesis. In an embodiment, the distal fixation member is configured such that it does not push leaflets of the native semilunar valve towards semilunar sinus floors of the native valve complex upon implantation of the prosthesis.

In an embodiment, each of the proximal engagement arms is shaped so as define at least one trough that is configured to be positioned at least partially within a respective one of the semilunar sinuses.

In an embodiment, the three engagement arms meet one another at three respective junctures, the engagement arms are shaped so as define three peak complexes at the three respective junctures, and three trough complexes, each of which is between two of the peak complexes, and upon implantation of the prosthesis, at least a portion of each of the peak complexes is disposed distal to and in rotational alignment with a respective one of the native commissures, and each of the trough complexes is disposed at least partially within the respective one of the semilunar sinuses.

In an embodiment, the engagement arms are configured to be positioned, during an implantation procedure, at least partially within the respective ones of the semilunar sinuses before the proximal fixation member is positioned at least partially on the ventricular side of the native valve complex, such that the engagement arms prevent leaflets of the native valve complex from opening more than a predetermined desired amount, the opening being because of force applied by the proximal fixation member to the leaflets.

In an embodiment, the proximal fixation member is configured to be positioned at least partially in a ventricle of the subject upon implantation of the prosthesis.

In an embodiment, the prosthesis is configured to apply the first axial force such that a ratio of (a) the first axial force to (b) a radial force applied outwardly by the prosthesis against the native semilunar valve is greater than 1.5:1.

In an embodiment, the prosthesis is configured to less than fully open leaflets of the native valve complex when the prosthesis is implanted at the native semilunar valve complex.

In an embodiment, the distal fixation member is configured to elevate leaflets of the native semilunar valve from within the semilunar sinuses upon implantation of the prosthesis.

In an embodiment, the distal fixation member is configured to apply the first axial force to respective roots of one or more leaflets of the native valve complex. In an embodiment, the distal fixation member is configured to apply the first axial force to respective transitions between respective semilunar sinus floors and one or more leaflets of the native valve complex.

In an embodiment, the prosthesis is configured to apply the first axial force such that the ratio is greater than 3:1, such as greater than 6:1.

In an embodiment, the prosthesis is configured to apply the second axial force such that a ratio of (a) the second axial force to (b) a radial force applied outwardly by the prosthesis against the native semilunar valve is greater than 1.5:1, such as greater than 3:1, e.g., greater than 6:1.

In an embodiment, the prosthesis includes a prosthetic valve configured to assume a closed position during diastole and an open position during systole. In an embodiment, the prosthetic valve includes a collapsible pliant material, configured to assume the open and closed positions.

In an embodiment, the distal and proximal fixation members and the prosthetic valve are configured to define a single flow field through the distal and proximal fixation members and the prosthetic valve. Alternatively, the distal and proximal fixation members and the prosthetic valve are configured to define a plurality of flow fields through the distal and proximal fixation members and the prosthetic valve.

In an embodiment, the prosthetic valve includes one or more prosthetic leaflets, and the prosthetic valve is coupled to the prosthesis such that at least 50% of an axial length of the prosthetic leaflets is distal to native valve leaflets of the native semilunar valve upon implantation of the prosthesis.

In an embodiment, the distal fixation member is configured to apply the first axial force to one or more semilunar sinus floors of the native valve complex.

In an embodiment, the distal fixation member is configured not to apply force to leaflets of the native semilunar valve.

In an embodiment, the proximal fixation member is shaped so as to define at least one barb configured to apply a barb force to the ventricular side of the native valve complex. For some applications, the at least one barb is configured to pierce the ventricular side of the native valve complex. Alternatively, the at least one barb is configured to protrude into tissue of the ventricular side of the native value complex, without piercing the tissue. For some applications, the distal fixation member is shaped so as to define at least one mating barb, and the at least one barb of the proximal fixation member is configured to engage the at least one mating barb, so as to help hold the prosthesis in place.

In an embodiment, the proximal and distal fixation members are collapsible. For some applications, the distal fixation member is configured to be positioned, during an implantation procedure, in the downstream artery while collapsed, and to be expanded before the proximal fixation member is positioned at least partially on the ventricular side of the native valve complex. For some applications, the apparatus includes at least one tube selected from the group consisting of: an overtube and a trocar, and the proximal and distal fixation members are configured to be stored in the selected tube while collapsed, and to expand upon being deployed from the selected tube.

In an embodiment, the proximal fixation member includes an inner support structure, and the distal fixation member includes an outer support structure that is placed partially over the inner support structure.

In an embodiment, the outer support structure is shaped so as to define exactly three distal diverging strut supports, from which respective ones of the proximal engagement arms extend radially outward.

In an embodiment, the prosthesis is configured such that, upon implantation at the native valve complex, the engagement arms are aligned by rotation with respective ones of the semilunar sinuses.

In an embodiment, the prosthesis is configured such that, upon implantation at the native valve complex, the strut supports are aligned with respective ones of the native commissures.

In an embodiment, the prosthesis is configured such that the engagement arms self-align themselves by rotation during implantation of the prosthesis at the native valve complex.

In an embodiment, the inner support structure is shaped so as to define a plurality of distal diverging inner struts.

In an embodiment, the inner support structure is shaped so as to define a bulging proximal skirt, a proximal portion of which is configured to apply the second axial force. In an embodiment, the prosthesis includes a graft covering that covers at least a portion of the skirt.

In an embodiment, the inner support structure is shaped so as to define a plurality of distal diverging inner struts, and the skirt extends from the inner struts.

In an embodiment, the outer support structure is shaped so as to define exactly three distal diverging strut supports, from which respective ones of the proximal engagement arms extend radially outward, and each of the strut supports is positioned over a respective one of the inner struts.

In an embodiment, the engagement arms are positioned over a portion of the skirt.

In an embodiment, the prosthesis includes a valve including a collapsible pliant material, configured to assume a closed position during diastole and an open position during systole, and the pliant material includes a plurality of segments, at least two of which are coupled together by one of the strut supports and its respective one of the inner struts.

There is yet further provided, in accordance with an embodiment of the present invention, apparatus including a prosthesis for implantation at a native semilunar valve of a native valve complex of a subject, the prosthesis including:

a distal fixation member, configured to be positioned in a downstream artery of the subject selected from the group consisting of: an ascending aorta, and a pulmonary trunk, and to apply, to tissue that defines one or more semilunar sinuses of the native valve complex, a first axial force directed toward a ventricle of the subject; and a proximal fixation member coupled to the distal fixation member, the proximal fixation member configured to be positioned at least partially on a ventricular side of the native semilunar valve, and to apply, to the ventricular side of the native valve complex, a second axial force directed toward the downstream artery, such that application of the first and second forces couples the prosthesis to the native valve complex.

In an embodiment, the native semilunar valve includes a native aortic valve, the downstream artery includes the ascending aorta, the semilunar sinuses include respective aortic sinuses, and the distal fixation member is configured to be positioned in the ascending aorta, and to apply the first axial force to the tissue that defines the one or more aortic sinuses.

In an embodiment, the native semilunar valve includes a native pulmonary valve, the downstream artery includes the pulmonary trunk, the semilunar sinuses include respective pulmonary sinuses, and the distal fixation member is configured to be positioned in the pulmonary trunk, and to apply the first axial force to the tissue that defines the one or more pulmonary sinuses.

In an embodiment, the distal and proximal fixation members are configured to couple the prosthesis to the native valve complex by axially sandwiching the native valve complex from a downstream side and the ventricular side thereof, upon implantation of the prosthesis.

In an embodiment, the distal fixation member does not press upon native valve commissures of the native semilunar valve upon implantation of the prosthesis.

In an embodiment, the prosthesis is configured to apply a radial force of less than 0.5 pounds outwardly against the native semilunar valve. In an embodiment, the prosthesis is configured to apply the first axial force with a force of at least 40 g during diastole. In an embodiment, the prosthesis is configured to apply the second axial force with a force of at least 1 g during systole.

In an embodiment, the prosthesis is configured such that any radial force applied by the prosthesis outwardly against the native semilunar valve is insufficient by itself to chronically maintain the prosthesis in position with respect to the native valve complex under conditions of normal cardiac motion.

In an embodiment, the prosthesis is configured, upon implantation thereof, to embrace, such as gently embrace, without squeezing, leaflets of the native semilunar valve.

In an embodiment, the distal fixation member is configured to be positioned in the downstream artery during an implantation procedure before the proximal fixation member is positioned at least partially on the ventricular side of the native valve complex.

In an embodiment, the distal fixation member is configured such that it does not fold over leaflets of the native semilunar valve upon implantation of the prosthesis. In an embodiment, the distal fixation member is configured such that it does not push leaflets of the native semilunar valve towards semilunar sinus floors of the native valve complex upon implantation of the prosthesis. In an embodiment, the prosthesis is configured to less than fully open leaflets of the native valve complex when the prosthesis is implanted at the native valve complex.

In an embodiment, the distal fixation member is configured to apply the first axial force to respective roots of one or more leaflets of the native valve complex. In an embodiment, the distal fixation member is configured to apply the first axial force to respective transitions between respective semilunar sinus floors and one or more leaflets of the native valve complex.

In an embodiment, the proximal fixation member is configured to be positioned at least partially in a ventricle of the subject upon implantation of the prosthesis.

In an embodiment, the prosthesis is configured to apply the first axial force such that a ratio of (a) the first axial force to (b) a radial force applied outwardly by the prosthesis against the native semilunar valve is greater than 1.5:1, such as greater than 3:1, e.g., greater than 6:1.

In an embodiment, the prosthesis is configured to apply the second axial force such that a ratio of (a) the second axial force to (b) a radial force applied outwardly by the prosthesis against the native semilunar valve is greater than 1.5:1, such as greater than 3:1, e.g., greater than 6:1.

In an embodiment, the prosthesis includes a prosthetic valve configured to assume a closed position during diastole and an open position during systole. In an embodiment, the prosthetic valve includes a collapsible pliant material, configured to assume the open and closed positions.

In an embodiment, the distal and proximal fixation members and the prosthetic valve are configured to define a single flow field through the distal and proximal fixation members and the prosthetic valve. Alternatively, the distal and proximal fixation members and the prosthetic valve are configured to define a plurality of flow fields through the distal and proximal fixation members and the prosthetic valve.

In an embodiment, the prosthetic valve includes one or more prosthetic leaflets, and the prosthetic valve is coupled to the prosthesis such that at least 50% of an axial length of the prosthetic leaflets is distal to native valve leaflets of the native semilunar valve upon implantation of the prosthesis.

In an embodiment, the distal fixation member is configured to apply the first axial force to one or more semilunar sinus floors of the native valve complex.

In an embodiment, the distal fixation member is configured not to apply force to leaflets of the native semilunar valve.

In an embodiment, the distal fixation member is shaped so as to define one or more proximal engagement arms that are configured to be positioned at least partially within respective ones of the semilunar sinuses, and, in combination, to apply the first axial force.

In an embodiment, the distal fixation member is shaped so as to define exactly three proximal engagement arms.

In an embodiment, each of the proximal engagement arms is shaped so as define at least one trough that is configured to be positioned at least partially within a respective one of the semilunar sinuses.

In an embodiment, the three engagement arms meet one another at three respective junctures, the engagement arms are shaped so as define three peak complexes at the three respective junctures, and three trough complexes, each of which is between two of the peak complexes, and upon implantation of the prosthesis, at least a portion of each of the peaks is disposed distal to and in rotational alignment with a respective native commissure of the native semilunar valve, and each of the trough complexes is disposed at least partially within the respective one of the semilunar sinuses.

In an embodiment, the distal fixation member is shaped so as to define exactly two proximal engagement arms.

In an embodiment, the engagement arms are configured to be positioned, during an implantation procedure, at least partially within the respective ones of the semilunar sinuses before the proximal fixation member is positioned at least partially on the ventricular side of the native valve complex, such that the engagement arms prevent leaflets of the native valve complex from opening more than a predetermined desired amount, the opening being because of force applied by the proximal fixation member to the leaflets.

In an embodiment, the proximal fixation member is shaped so as to define at least one barb configured to apply a barb force to the ventricular side of the native valve complex. For some applications, the at least one barb is configured to pierce the ventricular side of the native valve complex. Alternatively, the at least one barb is configured to protrude into tissue of the ventricular side of the native value complex, without piercing the tissue. For some applications, the distal fixation member is shaped so as to define at least one mating barb, and the at least one barb of the proximal fixation member is configured to engage the at least one mating barb, so as to help hold the prosthesis in place.

In an embodiment, the proximal and distal fixation members are collapsible. For some applications, the distal fixation member is configured to be positioned, during an implantation procedure, in the downstream artery while collapsed, and to be expanded before the proximal fixation member is positioned at least partially on the ventricular side of the native valve complex. For some applications, the apparatus includes at least one tube selected from the group consisting of: an overtube and a trocar, and the proximal and distal fixation members are configured to be stored in the selected tube while collapsed, and to expand upon being deployed from the selected tube.

In an embodiment, the proximal fixation member includes an inner support structure, and the distal fixation member includes an outer support structure that is placed partially over the inner support structure.

In an embodiment, the outer support structure is shaped so as to define a plurality of distal diverging strut supports, from which a plurality of proximal engagement arms extend radially outward.

In an embodiment, the prosthesis is configured such that, upon implantation at the native valve complex, the engagement arms are aligned by rotation with respective ones of the semilunar sinuses.

In an embodiment, the prosthesis is configured such that, upon implantation at the native valve complex, the strut supports are aligned with respective commissures of the native valve complex.

In an embodiment, the prosthesis is configured such that the engagement arms self-align themselves by rotation during implantation of the prosthesis at the native valve complex.

In an embodiment, the inner support structure is shaped so as to define a plurality of distal diverging inner struts.

In an embodiment, the inner support structure is shaped so as to define a bulging proximal skirt, a proximal portion of which is configured to apply the second axial force. For some applications, the prosthesis includes a graft covering that covers at least a portion of the skirt.

In an embodiment, the inner support structure is shaped so as to define a plurality of distal diverging inner struts, and the skirt extends from the inner struts.

In an embodiment, the outer support structure is shaped so as to define a plurality of distal diverging strut supports, from which a plurality of proximal engagement arms extend radially outward, and each of the strut supports is positioned over a respective one of the inner struts.

In an embodiment, the engagement arms are positioned over a portion of the skirt.

In an embodiment, the prosthesis includes a valve including a collapsible pliant material, configured to assume a closed position during diastole and an open position during systole, and the pliant material includes a plurality of segments, at least two of which are coupled together by one of the strut supports and its respective one of the inner struts.

There is additionally provided, in accordance with an embodiment of the present invention, apparatus including a prosthesis for implantation at a native semilunar valve of a native valve complex of a subject, the prosthesis including:

a distal fixation member, configured to be positioned in a downstream artery of the subject selected from the group consisting of: an ascending aorta, and a pulmonary trunk, and to apply, to native commissures of the native semilunar valve, a first axial force directed toward a ventricle of the subject, without applying any force to native leaflets of the native semilunar valve, and the distal fixation member is configured to rotationally align with the native semilunar valve; and a proximal fixation member coupled to the distal fixation member, the proximal fixation member configured to be positioned at least partially on a ventricular side of the native valve complex, and to apply a second axial force directed toward the downstream artery, such that application of the first and second forces couples the prosthesis to the native valve complex by axially sandwiching the native valve complex from a downstream side and the ventricular side thereof, upon implantation of the prosthesis.

In an embodiment, the native semilunar valve includes a native aortic valve, the downstream artery includes the ascending aorta, and the distal fixation member is configured to be positioned in the ascending aorta, and to apply the first axial force to the native commissures of the native aortic valve.

In an embodiment, the native semilunar valve includes a native pulmonary valve, the downstream artery includes the pulmonary trunk, and the distal fixation member is configured to be positioned in the pulmonary trunk, and to apply the first axial force to the native commissures of the native pulmonary valve.

In an embodiment, the distal fixation member is configured to rotationally self-align with the native semilunar valve.

In an embodiment, the distal fixation member includes one or more engagement arms that are positioned at least partially within respective semilunar sinuses of the native valve complex, upon implantation of the prosthesis.

In an embodiment, the engagement arms are configured to apply respective forces to respective floors of the semilunar sinuses, upon implantation of the prosthesis.

In an embodiment, the engagement arms are configured not to apply any force to floors of the semilunar sinuses, upon implantation of the prosthesis.

There is still additionally provided, in accordance with an embodiment of the present invention, apparatus including a prosthesis for implantation at a native semilunar valve of a native valve complex of a subject, the prosthesis including:

a distal fixation member, configured to be positioned in a downstream artery of the subject selected from the group consisting of: an ascending aorta, and a pulmonary trunk, and to apply a first axial force directed toward a ventricle of the subject; and a proximal fixation member coupled to the distal fixation member, the proximal fixation member configured to be positioned at least partially on a ventricular side of the native valve complex, and to apply a second axial force directed toward the downstream artery, such that application of the first and second forces couples the prosthesis to the native valve complex by axially sandwiching the native valve complex from a downstream side and the ventricular side thereof, wherein the prosthesis is configured to apply a radial force of less than 0.5 pounds outwardly against the native semilunar valve.

In an embodiment, the native semilunar valve includes a native aortic valve, the downstream artery includes the ascending aorta, and the distal fixation member is configured to be positioned in the ascending aorta.

In an embodiment, the native semilunar valve includes a native pulmonary valve, the downstream artery includes the pulmonary trunk, and the distal fixation member is configured to be positioned in the pulmonary trunk.

In an embodiment, the distal fixation member does not press upon native valve commissures of the native semilunar valve upon implantation of the prosthesis.

In an embodiment, the prosthesis is configured to apply the first axial force such that a ratio of (a) the first axial force to (b) the radial force is greater than 1.5:1. In an embodiment, the prosthesis is configured to apply the second axial force such that a ratio of (a) the second axial force to (b) the radial force is greater than 1.5:1. In an embodiment, the prosthesis is configured to apply the first axial force with a force of at least 40 g during diastole. In an embodiment, the prosthesis is configured to apply the second axial force with a force of at least 1 g during systole.

In an embodiment, the prosthesis is configured such that any radial force applied by the prosthesis outwardly against the native semilunar valve is insufficient by itself to chronically maintain the prosthesis in position with respect to the native valve complex under conditions of normal cardiac motion.

In an embodiment, the prosthesis is configured, upon implantation thereof, to embrace, such as gently embrace, without squeezing, leaflets of the native semilunar valve. In an embodiment, the distal fixation member is configured such that it does not fold over leaflets of the native semilunar valve upon implantation of the prosthesis. In an embodiment, the prosthesis is configured to less than fully open leaflets of the native valve complex when the prosthesis is implanted at the native valve complex.

In an embodiment, the proximal fixation member is configured to be positioned at least partially in a ventricle of the subject upon implantation of the prosthesis.

In an embodiment, the prosthesis includes a valve configured to assume a closed position during diastole and an open position during systole. In an embodiment, the valve includes a collapsible pliant material, configured to assume the open and closed positions.

In an embodiment, the distal and proximal fixation members and the valve are configured to define a single flow field through the distal and proximal fixation members and the valve. Alternatively, the distal and proximal fixation members and the valve are configured to define a plurality of flow fields through the distal and proximal fixation members and the valve.

In an embodiment, the valve includes one or more prosthetic leaflets, and the valve is coupled to the prosthesis such that at least 50% of an axial length of the prosthetic leaflets is distal to native valve leaflets of the native semilunar valve upon implantation of the prosthesis.

In an embodiment, the proximal fixation member is shaped so as to define at least one barb configured to apply a barb force to the ventricular side of the native valve complex. For some applications, the at least one barb is configured to pierce the ventricular side of the native valve complex. Alternatively, the at least one barb is configured to protrude into tissue of the ventricular side of the native valve complex, without piercing the tissue. For some applications, the distal fixation member is shaped so as to define at least one mating barb, and the at least one barb of the proximal fixation member is configured to engage the at least one mating barb, so as to help hold the prosthesis in place.

In an embodiment, the proximal and distal fixation members are collapsible. For some applications, the distal fixation member is configured to be positioned, during an implantation procedure, in the downstream artery while collapsed, and to be expanded before the proximal fixation member is positioned at least partially on the ventricular side of the native valve complex. For some applications, the apparatus includes at least one tube selected from the group consisting of: an overtube and a trocar, and the proximal and distal fixation members are configured to be stored in the selected tube while collapsed, and to expand upon being deployed from the selected tube.

In an embodiment, the proximal fixation member includes an inner support structure, and the distal fixation member includes an outer support structure that is placed partially over the inner support structure.

In an embodiment, the outer support structure is shaped so as to define a plurality of distal diverging strut supports, from which a plurality of proximal engagement arms extend radially outward.

In an embodiment, the inner support structure is shaped so as to define a plurality of distal diverging inner struts.

In an embodiment, the inner support structure is shaped so as to define a bulging proximal skirt, a proximal portion of which is configured to apply the second axial force. For some applications, the prosthesis includes a graft covering that covers at least a portion of the skirt.

In an embodiment, the inner support structure is shaped so as to define a plurality of distal diverging inner struts, and the skirt extends from the inner struts.

In an embodiment, the outer support structure is shaped so as to define a plurality of distal diverging strut supports, from which a plurality of proximal engagement arms extend radially outward, and each of the strut supports is positioned over a respective one of the inner struts.

In an embodiment, the engagement arms are positioned over a portion of the skirt.

In an embodiment, the prosthesis includes a valve including a collapsible pliant material, configured to assume a closed position during diastole and an open position during systole, and the pliant material includes a plurality of segments, at least two of which are coupled together by one of the strut supports and its respective one of the inner struts.

There is yet additionally provided, in accordance with an embodiment of the present invention, a method for implanting a valve prosthesis at a native semilunar valve of a native valve complex of a subject, the method including:

providing a distal fixation member of the valve prosthesis coupled to a proximal fixation member of the valve prosthesis, which distal fixation member is shaped so as to define exactly three proximal engagement arms;

positioning the distal fixation member in a downstream artery of the subject selected from the group consisting of: an ascending aorta, and a pulmonary trunk, such that the three proximal engagement arms are positioned at least partially within respective semilunar sinuses of the native valve complex, and, in combination, apply, to tissue that defines the semilunar sinuses, a first axial force directed toward a ventricle of the subject; and positioning the proximal fixation member at least partially on a ventricular side of the native semilunar valve, such that the proximal fixation member applies, to the ventricular side of the native valve complex, a second axial force directed toward the downstream artery, such that application of the first and second forces couples the prosthesis to the native valve complex.

In an embodiment, the native semilunar valve includes a native aortic valve, the downstream artery includes the ascending aorta, and positioning the distal fixation member includes positioning the distal fixation member in the ascending aorta.

In an embodiment, the native semilunar valve includes a native pulmonary valve, the downstream artery includes the pulmonary trunk, and positioning the distal fixation member includes positioning the distal fixation member in the pulmonary trunk.

In an embodiment, providing includes coupling the distal fixation member to the proximal fixation member before positioning the distal fixation member and before positioning the proximal fixation member.

In an embodiment, providing includes coupling the distal fixation member to the proximal fixation member after performing at least one action selected from the group consisting of: positioning the distal fixation member, and positioning the proximal fixation member.

In an embodiment, the distal fixation member and the proximal fixation member are fabricated as one integrated structure, and providing the distal fixation member coupled to the proximal fixation member includes providing the distal fixation member and the proximal fixation member that are fabricated as one integrated structure.

In an embodiment, positioning the distal and proximal fixation members includes positioning the engagement arms at least partially within the respective ones of the semilunar sinuses before positioning the proximal fixation member at least partially on the ventricular side of the native valve complex, such that the engagement arms prevent leaflets of the native valve complex from opening more than a predetermined desired amount, the opening being because of force applied by the proximal fixation member to the leaflets.

There is also provided, in accordance with an embodiment of the present invention, a method for implanting a valve prosthesis at a native semilunar valve of a native valve complex of a subject, the method including:

providing a distal fixation member of the valve prosthesis coupled to a proximal fixation member of the valve prosthesis;

positioning the distal fixation member in a downstream artery of the subject selected from the group consisting of: an ascending aorta, and a pulmonary trunk, such that the distal fixation member applies, to a downstream side of the native valve complex, a first axial force directed toward a ventricle of the subject; and positioning the proximal fixation member at least partially on a ventricular side of the native semilunar valve, such that the proximal fixation member applies, to a ventricular side of the native semilunar valve, a second axial force directed toward the downstream artery, such that application of the first and second forces couples the prosthesis to the native semilunar valve.

In an embodiment, the native semilunar valve includes a native aortic valve, the downstream artery includes the ascending aorta, and positioning the distal fixation member includes positioning the distal fixation member in the ascending aorta.

In an embodiment, the native semilunar valve includes a native pulmonary valve, the downstream artery includes the pulmonary trunk, and positioning the distal fixation member includes positioning the distal fixation member in the pulmonary trunk.

In an embodiment, providing includes coupling the distal fixation member to the proximal fixation member before positioning the distal fixation member and before positioning the proximal fixation member.

In an embodiment, providing includes coupling the distal fixation member to the proximal fixation member after performing at least one action selected from the group consisting of: positioning the distal fixation member, and positioning the proximal fixation member.

In an embodiment, the distal fixation member and the proximal fixation member are fabricated as one integrated structure, and providing the distal fixation member coupled to the proximal fixation member includes providing the distal fixation member and the proximal fixation member that are fabricated as one integrated structure.

In an embodiment, positioning the distal and proximal fixation members includes positioning the distal fixation member in the downstream artery before positioning the proximal fixation member at least partially on the ventricular side of the native semilunar valve.

In an embodiment, the prosthesis includes a prosthetic valve, and positioning the distal fixation member includes positioning the distal fixation member such that the valve assumes a closed position during diastole and an open position during systole.

In an embodiment, positioning the distal fixation member includes positioning the distal fixation member such that it limits an extent of opening of leaflets of the native valve complex.

In an embodiment, positioning the proximal and distal fixation members includes:

collapsing the proximal and distal fixation members;

inserting the proximal and distal fixation members, while collapsed, in the ventricle and the downstream artery, respectively; and expanding the proximal and distal fixation members in the ventricle and the downstream artery, respectively.

In an embodiment, positioning the distal fixation member includes positioning the distal fixation member in the downstream artery while collapsed, and expanding the distal fixation member before positioning the proximal fixation member at least partially on the ventricular side of the native semilunar valve.

In an embodiment, inserting the proximal and distal fixation members includes storing the proximal and distal fixation members while collapsed in at least one tube selected from the group consisting of: an overtube and a trocar, and expanding the proximal and distal fixation members includes deploying the proximal and distal fixation members from the selected tube.

In an embodiment, the native semilunar valve includes a native aortic valve, the downstream artery includes the ascending aorta, and inserting the proximal and distal fixation members includes inserting the selected tube through an apex of a heart of the subject, and advancing the selected tube through the ventricle until a distal end of the selected tube passes the native semilunar valve.

In an embodiment, the native semilunar valve includes a native aortic valve, the downstream artery includes the ascending aorta, and inserting the proximal and distal fixation members includes inserting the selected tube using a transaortic approach.

In an embodiment, the native semilunar valve includes a native pulmonary valve, the downstream artery includes the pulmonary trunk, the ventricle includes a right ventricle, and inserting the proximal and distal fixation members includes inserting the selected tube through a free wall of the right ventricle, and advancing the selected tube through the right ventricle past a right ventricular outflow tract of the heart until a distal end of the selected tube passes the native pulmonary valve.

In an embodiment, the proximal fixation member includes an inner support structure, the distal fixation member includes an outer support structure that is placed partially over the inner support structure, and positioning the proximal and distal fixation members includes positioning the inner and outer support structures, respectively.

In an embodiment, the outer support structure is shaped so as to define a plurality of distal diverging strut supports, from which a plurality of proximal engagement arms extend radially outward, and positioning the outer support structure includes rotationally aligning the engagement arms with respective ones of the semilunar sinuses.

In an embodiment, positioning the outer support structure includes rotationally aligning the strut supports with respective commissures of the native valve complex.

In an embodiment, aligning the engagement arms and the strut supports includes moving the outer support structure in a proximal direction, such that the engagement arms self-align with the respective ones of the semilunar sinuses.

There is further provided, in accordance with an embodiment of the present invention, a method for implanting a valve prosthesis at a native semilunar valve of a native valve complex of a subject, the method including:

providing a distal fixation member of the valve prosthesis coupled to a proximal fixation member of the valve prosthesis;

positioning the distal fixation member in a downstream artery of the subject selected from the group consisting of: an ascending aorta, and a pulmonary trunk, such that the distal fixation member applies, to native commissures of the native semilunar valve, a first axial force directed toward a ventricle of the subject, without applying any force to native leaflets of the native semilunar valve;

causing the distal fixation member to rotationally align with the native semilunar valve by gently rotating the valve prosthesis; and positioning the proximal fixation member at least partially on a ventricular side of the native valve complex, such that the proximal fixation member applies a second axial force directed toward the downstream artery, such that application of the first and second forces couples the prosthesis to the native valve complex by axially sandwiching the native valve complex from a downstream side and the ventricular side thereof.

In an embodiment, the native semilunar valve includes a native aortic valve, the downstream artery includes the ascending aorta, and positioning the distal fixation member includes positioning the distal fixation member in the ascending aorta.

In an embodiment, the native semilunar valve includes a native pulmonary valve, the downstream artery includes the pulmonary trunk, and positioning the distal fixation member includes positioning the distal fixation member in the pulmonary trunk.

In an embodiment, causing the distal fixation member to align includes causing the distal fixation member to rotationally self-align with the native semilunar valve.

In an embodiment, providing includes coupling the distal fixation member to the proximal fixation member before positioning the distal fixation member and before positioning the proximal fixation member.

In an embodiment, providing includes coupling the distal fixation member to the proximal fixation member after performing at least one action selected from the group consisting of: positioning the distal fixation member, and positioning the proximal fixation member.

In an embodiment, the distal fixation member and the proximal fixation member are fabricated as one integrated structure, and providing the distal fixation member coupled to the proximal fixation member includes providing the distal fixation member and the proximal fixation member that are fabricated as one integrated structure.

There is still further provided, in accordance with an embodiment of the present invention, a method for implanting a valve prosthesis at a native semilunar valve of a native valve complex of a subject, the method including:

providing a distal fixation member of the valve prosthesis coupled to a proximal fixation member of the valve prosthesis;

positioning the distal fixation member in a downstream artery of the subject selected from the group consisting of: an ascending aorta, and a pulmonary trunk, such that the distal fixation member applies a first axial force directed toward a ventricle of the subject; and positioning the proximal fixation member at least partially on a ventricular side of the native valve complex, such that the proximal fixation member applies a second axial force directed toward the downstream artery, such that application of the first and second forces couples the prosthesis to the native valve complex by axially sandwiching the native valve complex from a downstream side and the ventricular side thereof, and the prosthesis applies a radial force of less than 0.5 pounds outwardly against the native semilunar valve.

In an embodiment, the native semilunar valve includes a native aortic valve, the downstream artery includes the ascending aorta, and positioning the distal fixation member includes positioning the distal fixation member in the ascending aorta.

In an embodiment, the native semilunar valve includes a native pulmonary valve, the downstream artery includes the pulmonary trunk, and positioning the distal fixation member includes positioning the distal fixation member in the pulmonary trunk.

In an embodiment, providing includes coupling the distal fixation member to the proximal fixation member before positioning the distal fixation member and before positioning the proximal fixation member.

In an embodiment, providing includes coupling the distal fixation member to the proximal fixation member after performing at least one action selected from the group consisting of: positioning the distal fixation member, and positioning the proximal fixation member.

In an embodiment, the distal fixation member and the proximal fixation member are fabricated as one integrated structure, and providing the distal fixation member coupled to the proximal fixation member includes providing the distal fixation member and the proximal fixation member that are fabricated as one integrated structure.

There is yet further provided, in accordance with an embodiment of the present invention, apparatus including a prosthesis for implantation at a native semilunar valve of a native valve complex of a subject, the prosthesis including:

a distal fixation member, configured to be positioned in a downstream artery of the subject selected from the group consisting of: an ascending aorta, and a pulmonary trunk, and to apply a first axial force directed toward a ventricle of the subject; and a proximal fixation member coupled to the distal fixation member, the proximal fixation member configured to be positioned at least partially on a ventricular side of the native valve complex, and to apply a second axial force directed toward the downstream artery, such that application of the first and second forces couples the prosthesis to the native valve complex by axially sandwiching the native valve complex from a downstream side and the ventricular side thereof, wherein the prosthesis is configured to apply the first axial force such that a ratio of (a) the first axial force to (b) a radial force applied outwardly by the prosthesis against the native semilunar valve is greater than 1.5:1.

In an embodiment, the native semilunar valve includes a native aortic valve, the downstream artery includes the ascending aorta, and the distal fixation member is configured to be positioned in the ascending aorta.

In an embodiment, the native semilunar valve includes a native pulmonary valve, the downstream artery includes the pulmonary trunk, and the distal fixation member is configured to be positioned in the pulmonary trunk.

In an embodiment, the prosthesis is configured such that the radial force is less than 0.5 pounds. In an embodiment, the distal fixation member does not press upon native valve commissures of the native semilunar valve upon implantation of the prosthesis. In an embodiment, the prosthesis is configured to apply the first axial force with a force of at least 40 g during diastole.

In an embodiment, the prosthesis is configured such that any radial force applied by the prosthesis outwardly against the native semilunar valve is insufficient by itself to chronically maintain the prosthesis in position with respect to the native valve complex under conditions of normal cardiac motion.

In an embodiment, the prosthesis is configured, upon implantation thereof, to embrace, such as gently embrace, without squeezing, leaflets of the native semilunar valve.

In an embodiment, the distal fixation member is configured such that it does not fold over leaflets of the native semilunar valve upon implantation of the prosthesis. In an embodiment, the prosthesis is configured to less than fully open leaflets of the native valve complex when the prosthesis is implanted at the native valve complex.

In an embodiment, the proximal fixation member is configured to be positioned at least partially in a ventricle of the subject upon implantation of the prosthesis.

In an embodiment, the prosthesis is configured to apply the first axial force such that the ratio is greater than 3:1, such as greater than 6:1.

In an embodiment, the prosthesis includes a valve configured to assume a closed position during diastole and an open position during systole.

In an embodiment, the valve includes a collapsible pliant material, configured to assume the open and closed positions.

In an embodiment, the distal and proximal fixation members and the valve are configured to define a single flow field through the distal and proximal fixation members and the valve.

In an embodiment, the distal and proximal fixation members and the valve are configured to define a plurality of flow fields through the distal and proximal fixation members and the valve.

In an embodiment, the valve includes one or more prosthetic leaflets, and the valve is coupled to the prosthesis such that at least 50% of an axial length of the prosthetic leaflets is distal to native valve leaflets of the native semilunar valve upon implantation of the prosthesis.

In an embodiment, the proximal fixation member is shaped so as to define at least one barb configured to apply a barb force to the ventricular side of the native valve complex. For some applications, the at least one barb is configured to pierce the ventricular side of the native valve complex. Alternatively, the at least one barb is configured to protrude into tissue of the ventricular side of the native valve complex, without piercing the tissue. For some applications, the distal fixation member is shaped so as to define at least one mating barb, and the at least one barb of the proximal fixation member is configured to engage the at least one mating barb, so as to help hold the prosthesis in place.

In an embodiment, the proximal and distal fixation members are collapsible. For some applications, the distal fixation member is configured to be positioned, during an implantation procedure, in the downstream artery while collapsed, and to be expanded before the proximal fixation member is positioned at least partially on the ventricular side of the native valve complex. For some applications, the apparatus includes at least one tube selected from the group consisting of: an overtube and a trocar, and the proximal and distal fixation members are configured to be stored in the selected tube while collapsed, and to expand upon being deployed from the selected tube.

In an embodiment, the proximal fixation member includes an inner support structure, and the distal fixation member includes an outer support structure that is placed partially over the inner support structure.

In an embodiment, the outer support structure is shaped so as to define a plurality of distal diverging strut supports, from which a plurality of proximal engagement arms extend radially outward.

In an embodiment, the inner support structure is shaped so as to define a plurality of distal diverging inner struts.

In an embodiment, the inner support structure is shaped so as to define a bulging proximal skirt, a proximal portion of which is configured to apply the second axial force. For some applications, the prosthesis includes a graft covering that covers at least a portion of the skirt.

In an embodiment, the inner support structure is shaped so as to define a plurality of distal diverging inner struts, and the skirt extends from the inner struts.

In an embodiment, the outer support structure is shaped so as to define a plurality of distal diverging strut supports, from which a plurality of proximal engagement arms extend radially outward, and each of the strut supports is positioned over a respective one of the inner struts.

In an embodiment, the engagement arms are positioned over a portion of the skirt.

In an embodiment, the prosthesis includes a valve including a collapsible pliant material, configured to assume a closed position during diastole and an open position during systole, and the pliant material includes a plurality of segments, at least two of which are coupled together by one of the strut supports and its respective one of the inner struts.

There is additionally provided, in accordance with an embodiment of the present invention, apparatus including a prosthesis for implantation at a native semilunar valve of a native valve complex of a subject, the prosthesis including:

a distal fixation member, configured to be positioned in a downstream artery of the subject selected from the group consisting of: an ascending aorta, and a pulmonary trunk, and to apply a first axial force directed toward a ventricle of the subject; and a proximal fixation member coupled to the distal fixation member, the proximal fixation member configured to be positioned at least partially on a ventricular side of the native valve complex, and to apply a second axial force directed toward the downstream artery, such that application of the first and second forces couples the prosthesis to the native valve complex by axially sandwiching the native valve complex from a downstream side and the ventricular side thereof, wherein the prosthesis is configured such that any radial force applied by the prosthesis outwardly against the native semilunar valve is insufficient by itself to chronically maintain the prosthesis in position with respect to the native valve complex under conditions of normal cardiac motion.

In an embodiment, the native semilunar valve includes a native aortic valve, the downstream artery includes the ascending aorta, and the distal fixation member is configured to be positioned in the ascending aorta.

In an embodiment, the native semilunar valve includes a native pulmonary valve, the downstream artery includes the pulmonary trunk, and the distal fixation member is configured to be positioned in the pulmonary trunk.

In an embodiment, the prosthesis is configured to apply the first axial force such that a ratio of (a) the first axial force to (b) the radial force is greater than 1.5:1. In an embodiment, the prosthesis is configured to apply the second axial force such that a ratio of (a) the second axial force to (b) the radial force is greater than 1.5:1. In an embodiment, the prosthesis is configured such that the radial force is less than 0.5 pounds.

In an embodiment, the distal fixation member does not press upon native valve commissures of the native semilunar valve upon implantation of the prosthesis.

In an embodiment, the prosthesis is configured to apply the first axial force with a force of at least 40 g during diastole. In an embodiment, the prosthesis is configured to apply the second axial force with a force of at least 1 g during systole.

In an embodiment, the prosthesis is configured, upon implantation thereof, to embrace, such as gently embrace, without squeezing, leaflets of the native semilunar valve. In an embodiment, the distal fixation member is configured such that it does not fold over leaflets of the native semilunar valve upon implantation of the prosthesis. In an embodiment, the prosthesis is configured to less than fully open leaflets of the native valve complex when the prosthesis is implanted at the native valve complex.

In an embodiment, the prosthesis includes a valve configured to assume a closed position during diastole and an open position during systole. In an embodiment, the valve includes a collapsible pliant material, configured to assume the open and closed positions.

In an embodiment, the distal and proximal fixation members and the valve are configured to define a single flow field through the distal and proximal fixation members and the valve. For some applications, the distal and proximal fixation members and the valve are configured to define a plurality of flow fields through the distal and proximal fixation members and the valve.

In an embodiment, the valve includes one or more prosthetic leaflets, and the valve is coupled to the prosthesis such that at least 50% of an axial length of the prosthetic leaflets is distal to native valve leaflets of the native semilunar valve upon implantation of the prosthesis.

There is also provided, in accordance with an embodiment of the present invention, a method for implanting a valve prosthesis at a native semilunar valve of a native valve complex of a subject, the method including:

providing a distal fixation member of the valve prosthesis coupled to a proximal fixation member of the valve prosthesis;

positioning the distal fixation member in a downstream artery of the subject selected from the group consisting of: an ascending aorta, and a pulmonary trunk, such that the distal fixation member applies a first axial force directed toward a ventricle of the subject, such that a ratio of (a) the first axial force to (b) a radial force applied outwardly by the prosthesis against the native semilunar valve is greater than 1.5:1; and positioning the proximal fixation member at least partially on a ventricular side of the native valve complex, such that the proximal fixation member applies a second axial force directed toward the downstream artery, and application of the first and second forces couples the prosthesis to the native valve complex by axially sandwiching the native valve complex from a downstream side and the ventricular side thereof.

In an embodiment, the native semilunar valve includes a native aortic valve, the downstream artery includes the ascending aorta, and positioning the distal fixation member includes positioning the distal fixation member in the ascending aorta.

In an embodiment, the native semilunar valve includes a native pulmonary valve, the downstream artery includes the pulmonary trunk, and positioning the distal fixation member includes positioning the distal fixation member in the pulmonary trunk.

In an embodiment, providing includes coupling the distal fixation member to the proximal fixation member before positioning the distal fixation member and before positioning the proximal fixation member.

In an embodiment, providing includes coupling the distal fixation member to the proximal fixation member after performing at least one action selected from the group consisting of: positioning the distal fixation member, and positioning the proximal fixation member.

In an embodiment, the distal fixation member and the proximal fixation member are fabricated as one integrated structure, and providing the distal fixation member coupled to the proximal fixation member includes providing the distal fixation member and the proximal fixation member that are fabricated as one integrated structure.

There is still additionally provided, in accordance with an embodiment of the present invention, a method for implanting a valve prosthesis at a native semilunar valve of a native valve complex of a subject, the method including:

providing a distal fixation member of the valve prosthesis coupled to a proximal fixation member of the valve prosthesis;

positioning the distal fixation member in a downstream artery of the subject selected from the group consisting of: an ascending aorta, and a pulmonary trunk, such that the distal fixation member applies a first axial force directed toward a ventricle of the subject; and positioning the proximal fixation member at least partially on a ventricular side of the native valve complex, such that the proximal fixation member applies a second axial force directed toward the downstream artery, and application of the first and second forces couples the prosthesis to the native valve complex by axially sandwiching the native valve complex from a downstream side and the ventricular side thereof, wherein positioning the distal and proximal fixation members includes positioning the distal and proximal fixation members such that any radial force applied by the prosthesis outwardly against the native semilunar valve is insufficient by itself to chronically maintain the prosthesis in position with respect to the native valve complex under conditions of normal cardiac motion.

In an embodiment, the native semilunar valve includes a native aortic valve, the downstream artery includes the ascending aorta, and positioning the distal fixation member includes positioning the distal fixation member in the ascending aorta.

In an embodiment, the native semilunar valve includes a native pulmonary valve, the downstream artery includes the pulmonary trunk, and positioning the distal fixation member includes positioning the distal fixation member in the pulmonary trunk.

In an embodiment, providing includes coupling the distal fixation member to the proximal fixation member before positioning the distal fixation member and before positioning the proximal fixation member.

In an embodiment, providing includes coupling the distal fixation member to the proximal fixation member after performing at least one action selected from the group consisting of: positioning the distal fixation member, and positioning the proximal fixation member.

In an embodiment, the distal fixation member and the proximal fixation member which are fabricated as one integrated structure, and providing the distal fixation member coupled to the proximal fixation member includes providing the distal fixation member and the proximal fixation member that are fabricated as one integrated structure.

There is yet additionally provided, in accordance with an embodiment of the present invention, apparatus including a prosthesis for implantation at a native semilunar valve of a native valve complex of a subject, the prosthesis including:

a distal fixation member, configured to be positioned in a downstream artery of the subject selected from the group consisting of: an ascending aorta, and a pulmonary trunk, and to apply a first axial force directed toward a ventricle of the subject; and a proximal fixation member coupled to the distal fixation member, the proximal fixation member configured to be positioned at least partially on a ventricular side of the native valve complex, and to apply a second axial force directed toward the downstream artery, such that application of the first and second forces couples the prosthesis to the native valve complex by axially sandwiching the native valve complex from a downstream side and the ventricular side thereof, wherein the prosthesis is configured, upon implantation thereof, to embrace, without squeezing, leaflets of the native semilunar valve.

In an embodiment, the prosthesis is configured, upon implantation thereof, to gently embrace, without squeezing, the leaflets of the native semilunar valve.

In an embodiment, the native semilunar valve includes a native aortic valve, the downstream artery includes the ascending aorta, and the distal fixation member is configured to be positioned in the ascending aorta.

In an embodiment, the native semilunar valve includes a native pulmonary valve, the downstream artery includes the pulmonary trunk, and the distal fixation member is configured to be positioned in the pulmonary trunk.

In an embodiment, the prosthesis is configured such that any radial force applied by the prosthesis outwardly against the native semilunar valve is insufficient by itself to chronically maintain the prosthesis in position with respect to the native valve complex under conditions of normal cardiac motion.

In an embodiment, the prosthesis is configured to apply the first axial force such that a ratio of (a) the first axial force to (b) a radial force applied outwardly by the prosthesis against the native semilunar valve is greater than 1.5:1. In an embodiment, the prosthesis is configured to apply the second axial force such that a ratio of (a) the second axial force to (b) a radial force applied outwardly by the prosthesis against the native semilunar valve is greater than 1.5:1.

In an embodiment, the prosthesis is configured to apply a radial force of less than 0.5 pounds outwardly against the native semilunar valve.

In an embodiment, the distal fixation member does not press upon native valve commissures of the native semilunar valve upon implantation of the prosthesis.

In an embodiment, the prosthesis is configured to apply the first axial force with a force of at least 40 g during diastole. In an embodiment, the prosthesis is configured to apply the second axial force with a force of at least 1 g during systole.

In an embodiment, the prosthesis is configured such that any radial force applied by the prosthesis outwardly against the native semilunar valve is insufficient by itself to chronically maintain the prosthesis in position with respect to the native valve complex under conditions of normal cardiac motion.

In an embodiment, the distal fixation member is configured such that it does not fold over leaflets of the native semilunar valve upon implantation of the prosthesis. In an embodiment, the prosthesis is configured to less than fully open leaflets of the native valve complex when the prosthesis is implanted at the native valve complex.

In an embodiment, the prosthesis includes a valve configured to assume a closed position during diastole and an open position during systole. In an embodiment, the valve includes a collapsible pliant material, configured to assume the open and closed positions.

In an embodiment, the distal and proximal fixation members and the valve are configured to define a single flow field through the distal and proximal fixation members and the valve. Alternatively, the distal and proximal fixation members and the valve are configured to define a plurality of flow fields through the distal and proximal fixation members and the valve.

In an embodiment, the valve includes one or more prosthetic leaflets, and the valve is coupled to the prosthesis such that at least 50% of an axial length of the prosthetic leaflets is distal to native valve leaflets of the native semilunar valve upon implantation of the prosthesis.

There is also provided, in accordance with an embodiment of the present invention, apparatus including a valve prosthesis for implantation at a native semilunar valve of a subject, the prosthesis including:

one or more distal fixation members, which are configured to be coupled without suturing to the native semilunar valve such that the members prevent opening of native leaflets of the native semilunar valve to their maximum diameter; and a pliant material coupled to at least one of the distal fixation members, the pliant material having a closed position and an open position.

In an embodiment, the native semilunar valve includes a native aortic valve, and the one or more distal fixation members are configured to be coupled with suturing to the native aortic valve. In an embodiment, the native semilunar valve includes a native pulmonary valve, and the one or more distal fixation members are configured to be coupled with suturing to the native pulmonary valve.

In an embodiment, the one or more distal fixation members are configured to define a maximum extent of opening of the native leaflets.

In an embodiment, the one or more distal fixation members include at least two distal fixation members, and the at least two distal fixation members are configured such that upon implantation of the prosthesis, at least a portion of the native leaflets is positioned between the at least two distal fixation members.

There is further provided, in accordance with an embodiment of the present invention, a method for implanting a valve prosthesis at a native semilunar valve of a native valve complex of a subject, the method including:

providing a distal fixation member of the valve prosthesis coupled to a proximal fixation member of the valve prosthesis;

positioning the distal fixation member in a downstream artery of the subject selected from the group consisting of: an ascending aorta, and a pulmonary trunk, such that the distal fixation member applies a first axial force directed toward a ventricle of the subject; and positioning the proximal fixation member at least partially on a ventricular side of the native valve complex, such that the proximal fixation member applies a, second axial force directed toward the downstream artery, and application of the first and second forces couples the prosthesis to the native valve complex by axially sandwiching the native valve complex from a downstream side and the ventricular side thereof, wherein positioning the distal and proximal fixation members includes positioning the distal and proximal fixation members such that the valve prosthesis embraces, without squeezing, leaflets of the native semilunar valve.

In an embodiment, the native semilunar valve includes a native aortic valve, the downstream artery includes the ascending aorta, and positioning the distal fixation member includes positioning the distal fixation member in the ascending aorta. In an embodiment, the native semilunar valve includes a native pulmonary valve, the downstream artery includes the pulmonary trunk, and positioning the distal fixation member includes positioning the distal fixation member in the pulmonary trunk.

In an embodiment, positioning the distal and proximal fixation members includes positioning the distal and proximal fixation members such that the valve prosthesis gently embraces, without squeezing, the leaflets of the native semilunar valve.

There is still further provided, in accordance with an embodiment of the present invention, a method for implanting a valve prosthesis at a native semilunar valve of a subject, the method including:

positioning one or more distal fixation members of the valve prosthesis in a vicinity of the native semilunar valve, and a pliant material coupled to at least one of the distal fixation members has a closed position and an open position; and without suturing, coupling the one or more distal fixation members to the native semilunar valve such that the distal fixation members prevent opening of native leaflets of the native semilunar valve to their maximum diameter.

In an embodiment, the native semilunar valve includes a native aortic valve, and positioning includes positioning the one or more distal fixation members in the vicinity of the native aortic valve.

In an embodiment, the native semilunar valve includes a native pulmonary valve, and positioning includes positioning the one or more distal fixation members in the vicinity of the native pulmonary valve.

In an embodiment, positioning the one or more distal fixation members includes positioning the one or more distal fixation members to define a maximum extent of opening of the native leaflets.

In an embodiment, the one or more distal fixation members include at least two distal fixation members, and positioning includes positioning the at least two distal fixation members such that at least a portion of the native leaflets are positioned between the at least two distal fixation members.

There is further provided, in accordance with an embodiment of the present invention, apparatus including a prosthesis for implantation at a stenosed native aortic valve of a native valve complex of a subject, the prosthesis including:

a distal fixation member, configured to be positioned in an ascending aorta of the subject, and to apply, to an aortic side of the native valve complex, a first axial force directed toward a left ventricle of the subject; and a proximal fixation member coupled to the distal fixation member, the proximal fixation member configured to be positioned at least partially on a left-ventricular side of the native aortic valve, and to apply, to a left-ventricular side of the aortic annulus, a second axial force directed toward the ascending aorta, such that application of the first and second forces couples the prosthesis to the native valve complex.

In an embodiment, the distal fixation member is configured to be positioned in the ascending aorta during an implantation procedure before the proximal fixation member is positioned at least partially on the left-ventricular side of the native aortic valve.

In an embodiment, the distal fixation member is configured such that it does not crimp, fold, or compress leaflets of the native aortic valve upon implantation of the prosthesis.

In an embodiment, the distal fixation member is configured such that it does not push leaflets of the native aortic valve towards aortic sinus floors of the native valve complex upon implantation of the prosthesis.

In an embodiment, the prosthesis includes a valve configured to assume a closed position during diastole and an open position during systole.

In an embodiment, the valve includes a collapsible pliant material, configured to assume the open and closed positions.

In an embodiment, the distal and proximal fixation members and the valve are configured to define a single flow field through the distal and proximal fixation members and the valve.

In an embodiment, the distal and proximal fixation members and the valve are configured to define a plurality of flow fields through the distal and proximal fixation members and the valve.

In an embodiment, the prosthesis is configured to not fully open leaflets of the native valve complex when the prosthesis is implanted at the native aortic valve complex.

In an embodiment, the distal fixation member is configured to be positioned within one or more aortic sinuses of the native valve complex upon implantation of the prosthesis.

In an embodiment, the distal fixation member is configured to elevate leaflets of the native aortic valve from within the one or more aortic sinuses upon implantation of the prosthesis.

In an embodiment, the distal fixation member is configured to apply the first axial force to respective roots of one or more leaflets of the native valve complex.

In an embodiment, the distal fixation member is configured to apply the first axial force to respective transitions between respective aortic sinus floors and one or more leaflets of the native valve complex.

In an embodiment, the distal fixation member is configured to apply the first axial force to one or more aortic sinus floors of the native valve complex.

In an embodiment, the distal fixation member is shaped so as to define one or more proximal engagement arms that are configured to be positioned within respective ones of the aortic sinuses, and, in combination, to apply the first axial force.

In an embodiment, the arms are configured to be positioned, during an implantation procedure, within the respective ones of the aortic sinuses before the proximal fixation member is positioned at least partially on the left-ventricular side of the native aortic valve, such that the arms prevent leaflets of the native valve complex from opening more than a predetermined desired amount because of force applied by the proximal fixation member to the leaflets.

In an embodiment, the proximal fixation member is configured to be positioned at least partially in a left ventricle of the subject upon implantation of the prosthesis.

In an embodiment, the proximal fixation member is shaped so as to define at least one barb configured to apply a barb force to the left-ventricular side of the aortic annulus.

In an embodiment, the at least one barb is configured to pierce the left-ventricular side of the aortic annulus.

In an embodiment, the at least one barb is configured to protrude into tissue of the left-ventricular side of the aortic annulus, without piercing the tissue.

In an embodiment, the distal fixation member is shaped so as to define at least one mating barb, and the at least one barb of the proximal fixation member is configured to engage the at least one mating barb, so as to help hold the prosthesis in place.

In an embodiment, the proximal and distal fixation members are collapsible.

In an embodiment, the distal fixation member is configured to be positioned, during an implantation procedure, in the ascending aorta while collapsed, and to be expanded before the proximal fixation member is positioned at least partially on the left-ventricular side of the native aortic valve.

In an embodiment, the apparatus includes at least one tube selected from the group consisting of: an overtube and a trocar, and the proximal and distal fixation members are configured to be stored in the selected tube while collapsed, and to expand upon being deployed from the selected tube.

In an embodiment, the proximal fixation member includes an inner support structure, and the distal fixation member includes an outer support structure that is placed partially over the inner support structure.

In an embodiment, the outer support structure is shaped so as to define a plurality of distal diverging strut supports, from which a plurality of proximal engagement arms extend radially outward.

In an embodiment, the prosthesis is configured such that, upon implantation at the native valve complex, the engagement arms are aligned by rotation with respective ones of aortic sinuses of the native valve complex.

In an embodiment, the prosthesis is configured such that, upon implantation at the native valve complex, the strut supports are aligned with respective commissures of the native valve complex.

In an embodiment, the prosthesis is configured such that the engagement arms self-align themselves by rotation during implantation of the prosthesis at the native valve complex.

In an embodiment, the inner support structure is shaped so as to define a plurality of distal diverging inner struts.

In an embodiment, the inner support structure is shaped so as to define a bulging proximal skirt, a proximal portion of which is configured to apply the second axial force.

In an embodiment, the prosthesis includes a graft covering that covers at least a portion of the skirt.

In an embodiment, the inner support structure is shaped so as to define a plurality of distal diverging inner struts, and the skirt extends from the inner struts.

In an embodiment, the outer support structure is shaped so as to define a plurality of distal diverging strut supports, from which a plurality of proximal engagement arms extend radially outward, and each of the strut supports is positioned over a respective one of the inner struts.

In an embodiment, the engagement arms are positioned over a portion of the skirt.

In an embodiment, the membrane includes a plurality of segments, at least two of which are coupled together by one of the strut supports and its respective one of the inner struts.

There is further provided, in accordance with an embodiment of the invention, apparatus including a valve prosthesis for implantation at a stenosed native aortic valve of a subject, the prosthesis including:
one or more fixation members, which are configured to be coupled without suturing to the native aortic valve such that the members do not open native leaflets of the native aortic valve to their maximum diameter; and
a membrane coupled to at least one of the fixation members, the membrane having a closed position and an open position.

There is still further provided, in accordance with an embodiment of the invention, a method for treating a stenosed native aortic valve of a native valve complex of a subject, the method including:

positioning a distal fixation member of a valve prosthesis in an ascending aorta of the subject, such that the distal fixation member applies, to an aortic side of the native valve complex, a first axial force directed toward a left ventricle of the subject; and
positioning a proximal fixation member of the prosthesis at least partially on a left-ventricular side of the native aortic valve, such that the proximal fixation member applies, to a left-ventricular side of the aortic annulus, a second axial force directed toward the ascending aorta, such that application of the first and second forces couples the prosthesis to the native valve.

In an embodiment, positioning the distal and proximal fixation members includes positioning the distal fixation member in the ascending aorta before positioning the proximal fixation member at least partially on the left-ventricular side of the native aortic valve.

In an embodiment, positioning the distal fixation member includes positioning the distal fixation member such that it does not crimp, fold, or compress leaflets of the native aortic valve.

In an embodiment, positioning the distal fixation member includes positioning the distal fixation member such that it does not push leaflets of the native aortic valve towards aortic sinus floors of the native valve complex.

In an embodiment, the prosthesis includes a valve, and positioning the distal fixation member includes positioning the distal fixation member such that the valve assumes a closed position during diastole and an open position during systole.

In an embodiment, the valve includes a collapsible pliant material, and positioning the distal fixation member includes positioning the distal fixation member such that the pliant material assumes the open and closed positions.

In an embodiment, positioning the distal and proximal fixation members and the valve includes positioning the distal and proximal fixation members and the valve such that the distal and proximal fixation members and the valve define a single flow field through the distal and proximal fixation members and the valve.

In an embodiment, positioning the distal and proximal fixation members and the valve includes positioning the distal and proximal fixation members and the valve such that the distal and proximal fixation members and the valve define a plurality of flow fields through the distal and proximal fixation members and the valve.

In an embodiment, positioning the distal fixation member includes positioning the distal fixation member such that it does not fully open leaflets of the native valve complex.

In an embodiment, positioning the distal fixation member includes positioning the distal fixation member within one or more aortic sinuses of the native valve complex.

In an embodiment, positioning the distal fixation member includes positioning the distal fixation member such that it elevates leaflets of the native aortic valve from within the one or more aortic sinuses.

In an embodiment, positioning the distal fixation member includes positioning the distal fixation member such that the distal fixation member applies the first axial force to respective roots of one or more leaflets of the native valve complex.

In an embodiment, positioning the distal fixation member includes positioning the distal fixation member such that the distal fixation member applies the first axial force to respective transitions between respective aortic sinus floors and one or more leaflets of the native valve complex.

In an embodiment, positioning the distal fixation member includes positioning the distal fixation member such that the distal fixation member applies the first axial force to one or more aortic sinus floors of the native valve complex.

In an embodiment, the distal fixation member is shaped so as to define one or more proximal engagement arms, and positioning the distal fixation member includes positioning the engagement arms within respective ones of the aortic sinuses, such that the engagement arms apply the first axial force.

In an embodiment, positioning the arms includes positioning the arms before positioning the proximal fixation member, such that the arms prevent leaflets of the native valve complex from opening more than a predetermined desired amount because of force applied by the proximal fixation member to the leaflets.

In an embodiment, positioning the proximal fixation member includes positioning the proximal fixation member at least partially in a left ventricle of the subject.

In an embodiment, the proximal fixation member is shaped so as to define at least one barb, and positioning the proximal fixation member includes positioning the proximal fixation member applies a barb force to the left-ventricular side of the aortic annulus.

In an embodiment, positioning the proximal fixation member includes positioning the proximal fixation member such that the at least one barb pierces the left-ventricular side of the aortic annulus.

In an embodiment, positioning the proximal fixation member includes positioning the proximal fixation member such that the at least one barb protrudes into tissue of the left-ventricular side of the aortic annulus, without piercing the tissue.

In an embodiment, the distal fixation member is shaped so as to define at least one mating barb, and positioning the proximal and distal fixation members includes engaging the at least one barb by the at least one mating barb, so as to help hold the prosthesis in place.

In an embodiment, positioning the proximal and distal fixation members includes:
collapsing the proximal and distal fixation members;
inserting the proximal and distal fixation members, while collapsed, in the left ventricle and the ascending aorta, respectively; and
expanding the proximal and distal fixation members in the left ventricle and the ascending aorta, respectively.

In an embodiment, positioning the distal fixation member includes positioning the distal fixation member in the ascending aorta while collapsed, and expanding the distal fixation member before positioning the proximal fixation member at least partially on the left-ventricular side of the native aortic valve.

In an embodiment, inserting the proximal and distal fixation members includes storing the proximal and distal fixation members while collapsed in at least one tube selected from the group consisting of an overtube and a trocar, and expanding the proximal and distal fixation members includes deploying the proximal and distal fixation members from the selected tube.

In an embodiment, inserting the proximal and distal fixation members includes inserting the selected tube through an apex of a heart of the subject, and advancing the selected tube through the left ventricle until a distal end of the selected tube passes the native aortic valve.

In an embodiment, inserting the proximal and distal fixation members includes inserting the selected tube using a transaortic approach.

In an embodiment, the proximal fixation member includes an inner support structure, the distal fixation member includes an outer support structure that is placed partially over the inner support structure, and positioning the proximal and distal fixation members includes positioning the inner and outer support structures, respectively.

In an embodiment, the outer support structure is shaped so as to define a plurality of distal diverging strut supports, from which a plurality of proximal engagement arms extend radially outward, and positioning the outer support structure includes rotationally aligning the engagement arms with respective ones of the aortic sinuses.

In an embodiment, positioning the outer support structure includes rotationally aligning the strut supports with respective commissures of the native valve complex.

In an embodiment, aligning the engagement arms and the strut supports includes moving the outer support structure in a proximal direction, such that the engagement arms self-align with the respective ones of the aortic sinuses.

In an embodiment, the inner support structure is shaped so as to define a bulging proximal skirt, and positioning the inner support structure includes positioning the inner support structure such that a proximal portion of the skirt applies the second axial force.

In an embodiment, the prosthesis includes a graft covering that covers at least a portion of the skirt, and positioning the inner support structure includes positioning the inner support structure including the graft covering.

In an embodiment, the inner support structure is shaped so as to define a plurality of distal diverging inner struts, the skirt extends from the inner struts, and positioning the inner support structure includes positioning the inner support structure that is shaped so as to define the plurality of distal diverging inner struts.

In an embodiment, the outer support structure is shaped so as to define a plurality of distal diverging strut supports, from which a plurality of proximal engagement arms extend radially outward, each of the strut supports is positioned over a respective one of the inner struts, and positioning the outer support structure includes positioning the outer support structure that is shaped so as to define the plurality of distal diverging strut supports.

In an embodiment, the engagement arms are positioned over a portion of the skirt, and positioning the outer support structure includes positioning the outer support structure including the engagement arms positioned over the portion of the skirt.

There is yet further provided, in accordance with an embodiment of the invention, a method for treating a stenosed native aortic valve of a subject, the method including:
positioning one or more fixation members of a valve prosthesis in a vicinity of the native aortic valve, and a membrane coupled to at least one of the fixation members has a closed position and an open position; and
without suturing, coupling the one or more fixation members to the native aortic valve such that the fixation members do not open native leaflets of the native aortic valve to their maximum diameter.

In some embodiments of the present invention, a fixation mechanism is provided for implanting a stent-based valve prosthesis for treating a native stenosed valve, such as an aortic valve. The fixation mechanism typically enables accurate positioning of the prosthesis in the native valve orifice in a guided self-aligning procedure, as well as safe and secure deployment and fixation.

In some embodiments of the present invention, the fixation mechanism includes one or more of the following components and/or features:

a distal (i.e., downstream) fixation member, which typically includes a fixation frame. When the valve prosthesis is in a collapsed position, the fixation frame is pressed against a body of the valve prosthesis by insertion into an outer sheath (i.e., an overtube);

the downstream fixation frame is shaped so as to define aortic sinus fixation arms, a number of which is typically equal to the number of aortic sinuses of the native valve;

the arms are configured to flare out laterally, when released from the outer sheath, to an angle with respect to a central axis of the prosthesis. Typically, the angle is precisely predefined by the design of the downstream fixation frame and arms, said angle open in the upstream direction. For some applications, the arms are shaped so as to curve outwards laterally;

upon deployment at the bottom of the aortic sinuses, the downstream fixation arms exert force largely or substantially only in the direction of the left ventricle (i.e., an axial force), and exert little or substantially no force in the radial direction;

the downstream fixation arms engage with the downstream side of the native valve leaflets, but not with the upstream side of the native valve leaflets. As a result: (a) the arms limit the opening motion of the native valve leaflets to the above-mentioned angle (which is typically predefined), and (b) the configuration of the arms enables the sequential entrapment of the native valve leaflets, first, from the downstream side by the fixation arms, and, second, from the upstream side, by a proximal (i.e., upstream) fixation member, thereby sandwiching the leaflets at the above-mentioned angle (which is typically predefined) without crimping, folding over, or bending the native leaflets;

the downstream fixation arms engage with an upstream portion of the valve prosthesis to form a locking mechanism, which, for some applications, includes barbs; and/or divergent commissural struts which encompass at their distal end an area larger than the native aortic orifice, so that the struts help resist migration of the valve prosthesis in an upstream direction (i.e., towards the left ventricle), and contribute to exerting and enhancing axial force in an upstream direction in a manner that increases with their outward angulation and the downstream (aortic) pressure.

In some embodiments of the present invention, the valve prosthesis is implanted using a transapical implantation procedure. An introducer overtube or trocar is inserted into the left ventricular apex using a Seldinger technique. Through this trocar, a delivery catheter onto which the collapsed valve prosthesis (covered by a sheath) is mounted, is advanced into the ascending aorta. Withdrawal of the sheath causes the fixation arms to flare out laterally to an angle which is typically predetermined by design, and to open in an upstream direction.

Gentle withdrawal and rotation of the delivery catheter, onto which the prosthesis with the flared-out arms is mounted, causes the arms to slide into the aortic sinuses, until the arms reach the bottom (anatomic inferior portion) of the sinuses. This rotational alignment occurs because the three-dimensional geometry of the downstream fixation frame, including the extended aortic sinus fixation arms, conforms to the three-dimensional geometry of the aortic valve and aortic root. In this position, the fixation arms engage with the downstream side of the native valve leaflets, and not with the upstream side of the native valve leaflets. Such engagement limits the opening motion of the native valve leaflets to the above-mentioned angle (which is typically predefined), so that the native leaflets are not pushed against the coronary arteries upon device release. In addition, such engagement provides the proper conditions for sequentially entrapping the native valve leaflets first from the downstream side (by the fixation arms), and subsequently from the upstream side (by the bottom of the valve prosthesis), thereby sandwiching the leaflets at the angle (which is typically predefined), without crimping, folding over, or bending the native leaflets.

Once the proper position of the arms at the bottom of the aortic sinuses is verified, the correct position for complete device release is automatically achieved. The proper position may be verified, for example, by (a) sensing an elastic resistance in the axial direction, and sensing that the device is rotationally locked in place, and/or (b) using imaging techniques such as fluoroscopy and/or ultrasound. Release of the device from the delivery catheter causes a lower inflow portion of the prosthesis to unfold and press against the upstream side of the native leaflets, thereby engaging with the upstream fixation arms in the aortic sinuses. The upstream fixation arms serve as counterparts to the lower inflow portion of the prosthesis in a mechanism that locks the native leaflets and the surrounding periannular tissue for fixation.

Device migration in the upstream direction (into the left ventricle) is prevented by (a) the aortic sinus fixation arms, which exert axial pressure against the bottom of the sinuses, and (b) the outwardly directed angulation of the longitudinally-oriented commissural struts of the prosthesis. The angulation of the struts not only prevents migration into the left ventricle by itself, but, during systole, also by exerting leverage on the aortic sinus fixation arms, which is a function of the degree of the angle and aortic pressure. Migration of the device in a downstream direction is prevented by the inflow part of the device pressing against the periannular tissue surrounding the upstream side of the valve leaflets, and by the inflow part of the device engaging with the fixation arms in a locking mechanism, which, for some applications, includes the use of barbs placed at the inflow section of the device in an upstream direction against the fixation arms.

In other embodiments of the present invention, the valve prosthesis is implanted using another implantation technique, such as an antegrade transseptal technique, or a retrograde endovascular-percutaneous technique.

The present invention will be more fully understood from the following detailed description of embodiments thereof, taken together with the drawings, in which:

BRIEF DESCRIPTION OF THE DRAWINGS

FIGS. 3A-E are schematic illustrations of additional configurations of the outer support structure of FIG. 2A, in accordance with respective embodiments of the present invention;

FIG. 3F is a schematic illustration of an additional configuration of the outer support structure of FIG. 2A, in accordance with an embodiment of the present invention;

FIG. 3G is a schematic illustration of a fully-assembled valve prosthesis that includes inner engagement arms of the configuration of FIG. 3F, in accordance with an embodiment of the present invention;

FIGS. 5A-C, 6A-B, 7A-E, and 8A illustrate apparatus and a method for implanting the valve prosthesis of FIG. 1 in a native stenosed valve of a heart, in accordance with respective embodiments of the present invention;

FIGS. 8B-C illustrate the prosthesis of FIG. 1 in situ, in accordance with respective embodiments of the present invention;

FIGS. 10A and 10B show the valve prosthesis of FIG. 1 in open (systolic) and closed (diastolic) positions, respectively, in accordance with an embodiment of the present invention;

FIGS. 13A-D illustrate the loading of the valve prosthesis of FIG. 1 into a tube from the holding device of FIGS. 12A-G, in accordance with an embodiment of the present invention;

FIGS. 16A-H schematically illustrate another transapical technique for implanting the prosthesis of FIG. 1, in accordance with an embodiment of the present invention.

DETAILED DESCRIPTION OF EMBODIMENTS

Figure 1:
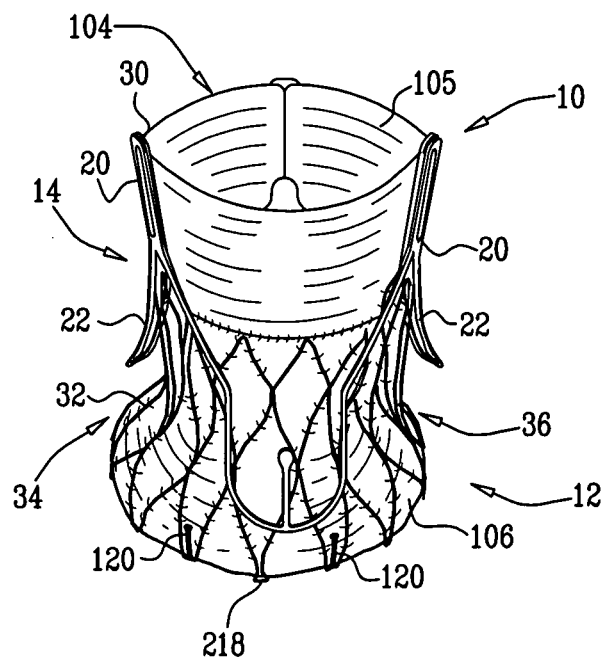
FIG. 1 is a schematic illustration of a fully-assembled valve prosthesis, in accordance with an embodiment of the present invention.

FIG. 1 is a schematic illustration of a fully-assembled valve prosthesis 10, in accordance with an embodiment of the present invention. Valve prosthesis 10 comprises a collapsible inner support structure 12 that serves as a proximal fixation member, and a collapsible outer support structure 14 that serves as a distal fixation member. Outer and inner support structures 14 and 12 may be initially formed separately and then joined together, as shown, or may be formed as one integrated structure, i.e., not formed separately and then joined together. For some applications, outer and inner support structures 14 and 12 are joined together prior to implantation of prosthesis 10 (during a manufacturing process, or by a healthcare worker prior to implantation), while for other applications, the outer and inner support structures are coupled to one another during an implantation procedure. For some applications, outer support structure 14 is constructed from a plurality of separate pieces, which are joined to inner support structure 12 using standard manufacturing means, such as welding, gluing, or suturing (configuration not shown), such that the functionality of outer support structure 14 is attained.

Valve prosthesis 10 is configured to be placed in a native diseased valve of a subject, such as a native stenotic aortic or pulmonary valve, using a minimally-invasive approach, such as a beating heart transapical procedure, such as described hereinbelow with reference to FIGS. 5A-8A or with reference to FIGS. 16A-H, or a retrograde transaortic procedure, such as described hereinbelow with reference to FIGS. 9A-G. As used in the present application, including in the claims, a "native semilunar valve" is to be understood as including: (a) native semilunar valves that include their native leaflets, and (b) native semilunar valves, the native leaflets of which have been surgically excised or are otherwise absent.

Figure 2A:
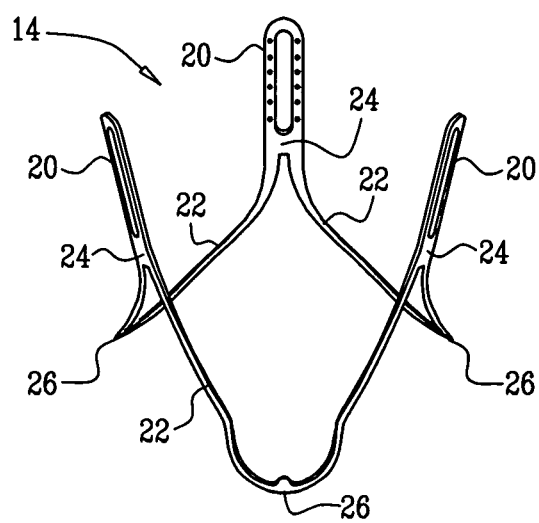
FIG. 2A is a schematic illustration of a collapsible outer support structure of the prosthesis of FIG. 1 prior to assembly with an inner support structure of the prosthesis, in accordance with an embodiment of the present invention.

Reference is made to FIG. 2A, which is a schematic illustration of collapsible outer support structure 14 prior to assembly with inner support structure 12, in accordance with an embodiment of the present invention. Outer support structure 14 is shaped so as to define a plurality of distal diverging strut supports 20, from which a plurality of proximal engagement arms 22 extend radially outward in a proximal direction. Typically, the engagement arms have a shape that is generally upwardly concave, such as described hereinbelow with reference to FIG. 17.

Although three strut supports 20 and engagement arms 22 are shown in the figures, for some applications valve prosthesis 10 comprises fewer or more supports and/or arms, such as two supports and two arms. It is noted that approximately 90% of humans have exactly three aortic sinuses. The three supports and/or arms provided in most embodiments correspond to these three aortic sinuses. For implantation in the approximately 10% of patients that have exactly two aortic sinuses, prosthesis 10 typically includes exactly two supports and/or arms.

Figure 3A:
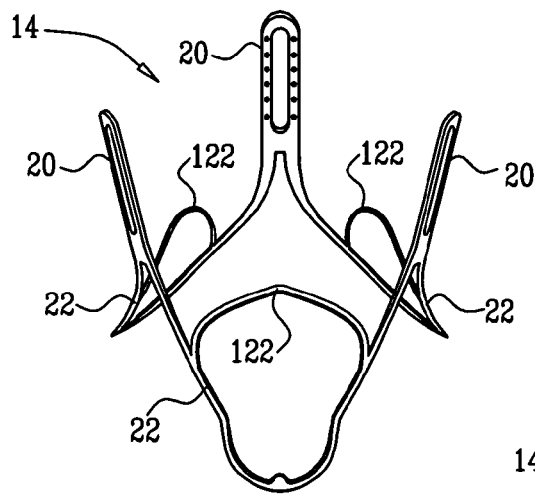
Figure 3B:
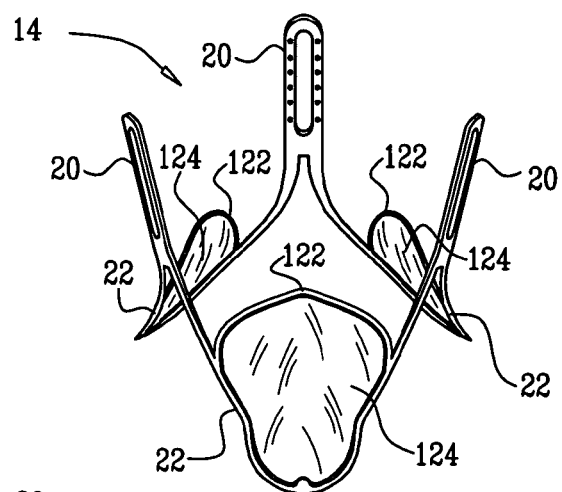
Figure 3C:
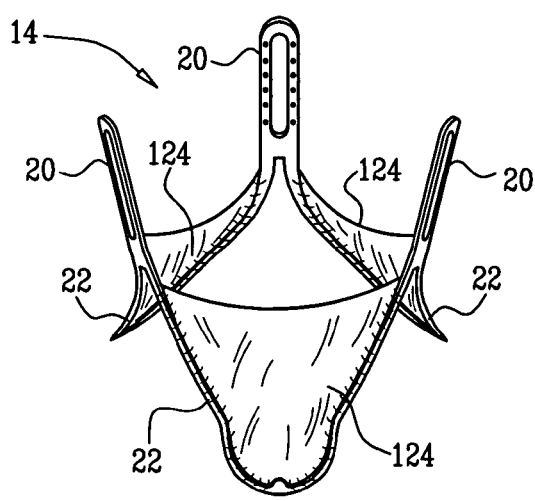

Engagement arms 22 are typically configured to be at least partially disposed within aortic sinuses of the subject, and, for some applications, to engage and/or rest against floors of the aortic sinuses, and to apply an axial force directed toward a left ventricle of the subject. Engagement arms 22 meet one another at respective junctures 24. For applications in which each of engagements arms 22 is fabricated as a separate piece, the engagement arms are mechanically engaged to one another where they meet at respective junctures 24. For some applications, engagement arms 22 meet one another without actually touching one another, and instead meet via an area defined at each respective juncture 24. Typically, the engagement arms are configured to define respective peaks at junctures 24 (or peak complexes, as described hereinbelow with reference to FIG. 3E), and respective troughs 26 between each two of the peaks (or trough complexes, as described hereinbelow with reference to FIG. 3E).

Outer support structure 14 comprises a suitable material that allows mechanical deformations associated with crimping and expansion of valve prosthesis 10, such as, but not limited to, nitinol or a stainless steel alloy (e.g., AISI 316). Outer support structure 14 is fabricated from a single piece or from a plurality of parts that are coupled together (e.g., by suturing). For some applications, placement of engagement arms 22 within the aortic sinuses prevents "device migration," i.e., undesired retrograde movement of valve prosthesis 10 that may result from fluid forces applied to the valve. For some applications, engagement arms 22 are coated with a flexible material (e.g., polyester, biocompatible, synthetic, and/or pericardium).

Strut supports 20 and engagement arms 22 may be formed as one integrated structure (as shown), or, alternatively, may be initially formed separately and then joined to one another. For example, the strut support and arms may be mechanically interlocked or sutured together, or coupled by other means. Typically, the strut support and arms are joined prior to implantation.

Figure 2B:
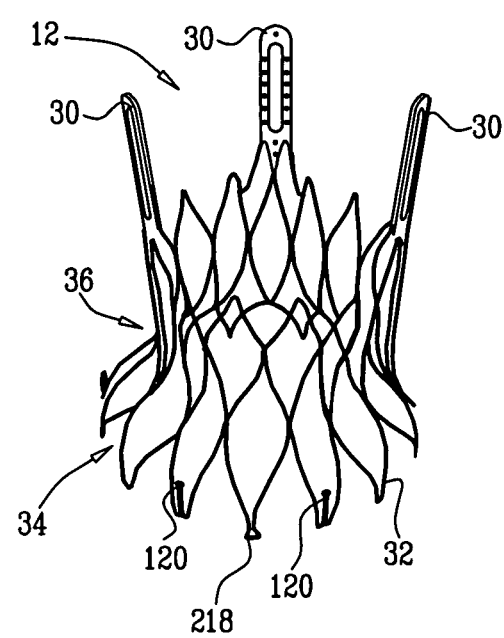
FIG. 2B is a schematic illustration of the collapsible inner support structure prior to assembly with the outer support structure of the prosthesis of FIG. 1, in accordance with an embodiment of the present invention.

Reference is made to FIG. 2B, which is a schematic illustration of collapsible inner support structure 12 prior to assembly with outer support structure 14, in accordance with an embodiment of the present invention. For some applications, inner support structure 12 is shaped so as to define a plurality of distal diverging inner struts 30, and a bulging proximal skirt 32 that extends from the struts. A proximal portion 34 of proximal skirt 32 is configured to engage a left ventricular outflow tract (LVOT) of the subject and/or periannular tissue at the top of the left ventricle. A relatively narrow throat section 36 of proximal skirt 32 is configured to be positioned at a valvular annulus of the subject, and to engage the native valve leaflets. Inner support structure 12 comprises, for example, nitinol, a stainless steel alloy, another metal, or another biocompatible material.

Reference is again made to FIG. 1. Inner and outer support structures 12 and 14 are assembled together by placing outer support structure 14 over inner support structure 12, such that outer strut supports 20 are aligned with, and typically support, respective inner struts 30, and engagement arms 22 are placed over a portion of proximal skirt 32. Inner struts 30 and outer strut supports 20 together function as commissural posts. Typically, such assembly is performed prior to implantation of prosthesis 10, such as during manufacture of the prosthesis; alternatively, such assembly is performed in vivo during an implantation procedure, or prior to implantation by a healthcare worker.

Valve prosthesis 10 typically comprises a prosthetic distal valve 104, which typically comprises a pliant material 105 coupled to strut supports 20 and/or inner struts 30. Pliant material 105 of valve 104 is configured to collapse inwardly (i.e., towards a longitudinal axis of valve prosthesis 10) during diastole, in order to inhibit retrograde blood flow, and to open outwardly during systole, to allow blood flow through the prosthesis. For some applications, when in an open position, valve 104 assumes a diverging shape that causes blood to flow therethrough with pressure recovery at a distal outlet of the valve, for example using techniques described in one or more of the above-mentioned patent application publications to Schwammenthal et al. For other applications, the shape of the valve does not cause such pressure recovery. For example, an angle between the pliant material 105 and a central longitudinal axis of prosthesis 10 may be too great to cause pressure recovery. In this latter case, the large angle may serve exclusively, or at least in part, to help provide axial fixation of prosthesis 10 to the native valve complex. Regardless of whether pressure recovery is achieved, the angle between pliant material 105 and the central longitudinal axis of prosthesis 10 typically inhibits migration of the device in an upstream direction.

Pliant material 105 comprises a flexible supple material, such as an inert biological material, e.g., pericardium sheet or any medically safe elastomer, such as, but not limited to, polyester, polymer, a metallic material/alloy, polyurethane, latex, or synthetic rubber. For some applications, pliant material 105 is coupled to strut supports 20 and/or inner struts 30 by sewing, such as described hereinbelow with reference to FIG. 4. For example, pliant material 105 may be sewn onto outer diverging strut supports 20. Valve 104 comprises a single piece or multiple pieces of pliant material 105 (e.g., leaflets) joined together to give a desired shape, typically a distally diverging shape. For some applications, the pliant material and support structures are coupled to one another in a single-step procedure (e.g., by sewing all the pieces together); alternatively, the pliant material and support structures are coupled to one another in a plurality of sequential steps.

Typically, valve prosthesis 10 further comprises a graft covering 106 which is coupled to proximal skirt 32, such as by sewing the covering within the skirt (configuration shown in FIG. 1) or around the skirt (configuration not shown). Inner support structure 12 thus defines a central structured body for flow passage that proximally terminates in a flared inlet (proximal skirt 32) that is configured to be seated within an LVOT immediately below an aortic annulus/aortic valve. For some applications, graft covering 106 is coupled at one or more sites to pliant material 105.

Figure 2C:
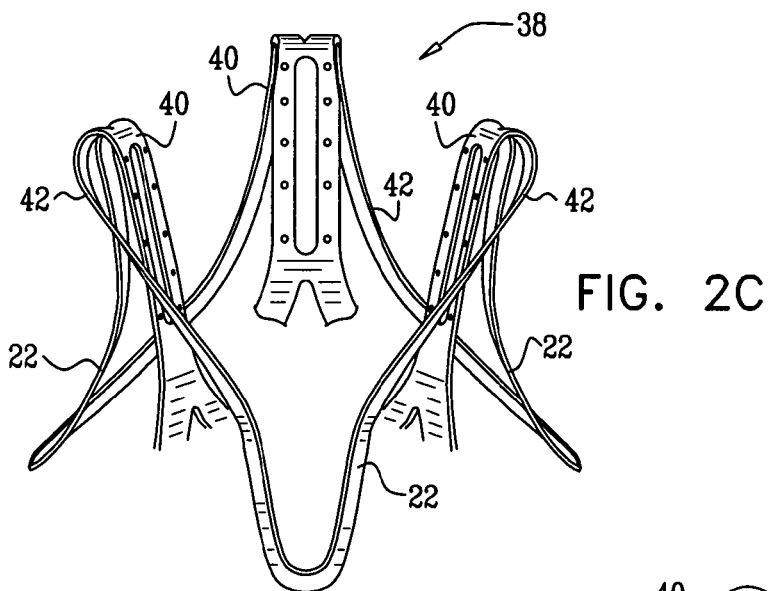
FIGS. 2C and 2D are schematic illustrations of alternative configurations of a portion of the prosthesis of FIG. 1, in accordance with respective embodiments of the present invention.
Figure 2D:
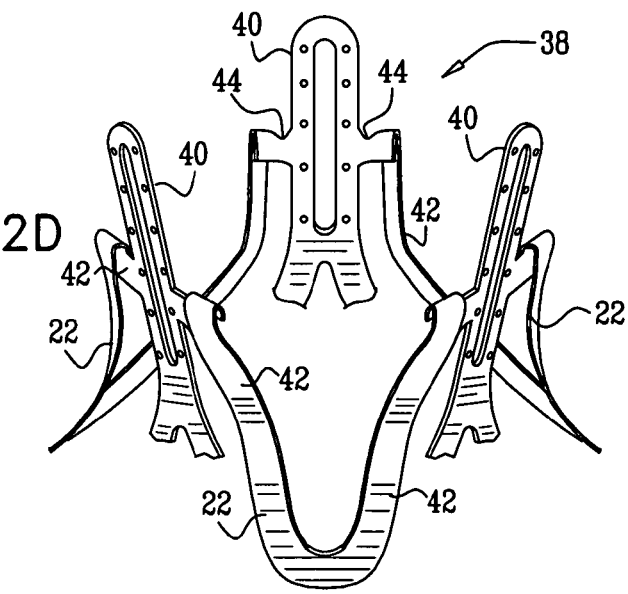

FIGS. 2C and 2D are schematic illustrations of alternative configurations of a portion of valve prosthesis 10, in accordance with respective embodiments of the present invention. In these configurations, inner support structure 12 and outer support structure 14 are replaced by an element 38, which is shaped so as to define first and second portions 40 and 42. First portions 40 serve as support structures, each of which functionally corresponds to a pair of strut support 20 and inner strut 30, described hereinabove with reference to FIGS. 2A and 2B. Pliant material 105 is coupled to support structures 40. Second portions 42 are bent in a proximal direction, such that proximal portions of the second portions define respective engagement arms 22.

In the configuration shown in FIG. 2C, two second portions 42 extend from the distal end of each first portion 40. In the configuration shown in FIG. 2D, element 38 is shaped so as to define two shoulders 44 that extend laterally from each first portion 40. A single second portion 42 extends from each of shoulders 44.

Reference is again made to FIG. 1. In an embodiment of the present invention, inner support structure 12 is shaped so as to define one or more barbs 120, which are configured to pierce or protrude into the ventricular side of the aortic annulus, as described hereinbelow with reference to FIGS. 7A-E. For some applications, one or more of inner struts 30 is shaped so as to define a respective barb, while for other applications, another element of valve prosthesis 10 is shaped so as to define the one or more barbs, such as proximal skirt 32. For some applications, barbs 120 are oriented parallel to a longitudinal axis of valve prosthesis 10, while for other applications, barbs 120 are oriented to form an angle with respect to the longitudinal axis, such as between about −20 degrees (i.e., slanted towards a central axis of the native valve) and about +89 degrees (i.e., slanted away from the central axis of the native valve), such as between about −5 and about +30 degrees. For some applications, barbs 120 are set at the desired angle by heat-setting.

Figure 2E:
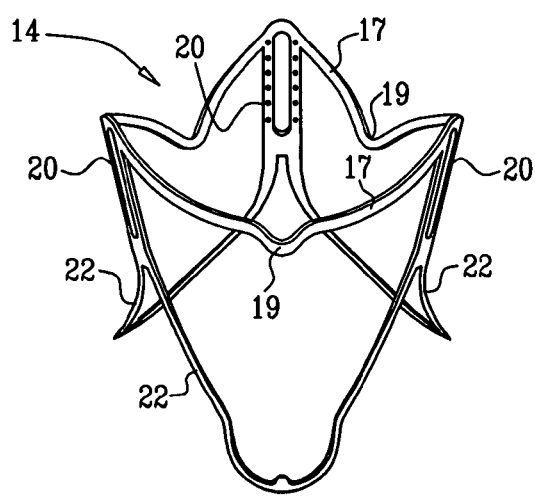
FIG. 2E is a schematic illustration of another configuration of a collapsible outer support structure of the prosthesis of FIG. 1 prior to assembly with an inner support structure of the prosthesis, in accordance with an embodiment of the present invention.

Reference is made to FIG. 2E, which is a schematic illustration of another configuration of collapsible outer support structure 14 prior to assembly with inner support structure 12, in accordance with an embodiment of the present invention. Inter-strut support elements 17 are coupled between adjacent ones of distal diverging strut supports 20, and typically serve to help maintain a desired distance between each of strut supports 20. For example, if a force is applied that would bring closer or separate two of the strut supports, the inter-strut support element between the strut supports would tend to reduce such a deformation. For some applications, one or more of support elements 17 is shaped so as to define a kink or curved section 19, which deforms slightly in response to force applied to element 17.

Reference is made to FIGS. 3A-E, which are schematic illustrations of additional configurations of outer support structure 14, in accordance with respective embodiments of the present invention. In the configurations shown in FIGS. 3A-B, outer support structure 14 is shaped so as to define one or more native valve support elements 122. These support elements apply pressure to an outer (downstream) surface of the native valve when engagement arms 22 are positioned in the aortic sinuses, so as to hold the native leaflets in place against proximal skirt 32. In the configuration shown in FIG. 3A, the area defined by engagement arms 22 and support elements 122 is open, while in the configuration shown in FIG. 3B, a covering 124 is provided in this area. The covering generally may help capture calcific, thrombotic, or other material which might be dislodged from the native valve or the surrounding tissue, and may comprise, for example, polyester. In the configuration shown in FIG. 3C, covering 124 is provided without support elements 122.

Figure 3D:
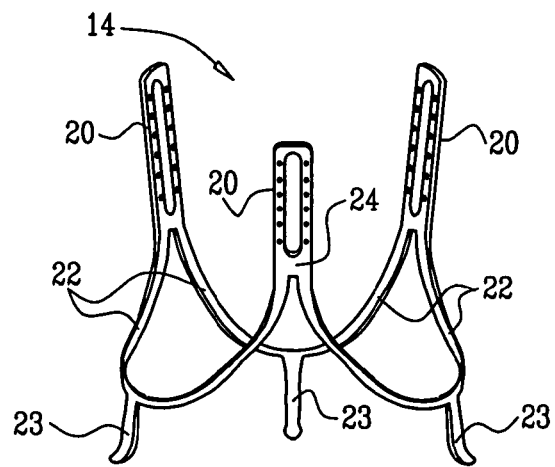

In the configuration shown in FIG. 3D, each of engagement arms 22 comprises or is shaped so as to define at least one extension element 23 that extends from the engagement arm. The engagement arms and extension elements are configured such that the engagement arms engage and/or rest against the floors of the aortic sinuses via the extension elements. For some applications, such as shown in FIG. 3D, exactly one extension element 23 extends from each of engagement arms 22, while for other applications, more than one extension element 23 extends from each engagement arm (configuration not shown). Although engagement arms 22 are shown in FIG. 3D as curving down toward the sinus floors, for some applications the engagement arms are shaped so as to remain above the native commissures (for example, the engagement arms collectively may be annular in shape), or to curve down less than is shown in FIG. 3D.

In the configuration shown in FIG. 3E, each of engagement arms 22 is shaped so as to define a plurality of troughs 25 and local peaks 27, rather than a single trough 26, as shown in FIG. 2A. In addition, each of engagement arms 22 is shaped so as to define a plurality of peaks 29 and local troughs 31, rather than a single peak at each of junctures 24, as shown in FIG. 2A. (Outer support structure 14 may include both, only one of, or neither of the features described in the preceding two sentences.) As used in the present application, including in the claims, a "trough complex" means a portion of an engagement arm that extends downwards between respective "peak complexes." Each "trough complex" includes n local troughs 25 and n-1 local peaks 29, where n is greater than or equal to one. Each "peak complex" includes m local peaks 29 and m-1 local troughs 31, where m is greater than or equal to one. It is noted that the portion of a peak complex that is at a juncture may define a local trough (configuration not shown). In addition, although the peak and trough complexes shown in FIG. 3E are generally symmetrical, non-symmetrical arrangements are also within the scope of the present invention.

For some applications, respective extension elements 23, described hereinabove with reference to FIG. 3D, extend from one or more of the troughs of a trough complex, and/or from elsewhere along the trough complex.

FIG. 3F is a schematic illustration of an additional configuration of outer support structure 14, in accordance with an embodiment of the present invention. In this embodiment, outer support structure 14, in addition to defining proximal engagement arms 22, is shaped so as to define a plurality of inner engagement arms 33. The inner engagement arms are configured to pass through the valvular annulus. Typically, troughs 35 of inner engagement arms 33 are configured to engage the LVOT and/or periannular tissue at the top of the left ventricle. For some applications, each of inner engagement arms 33 is shaped so as to define one or more barbs 37, which are configured to pierce or protrude into the ventricular side of the aortic annulus. Typically, during an implantation procedure, inner engagement arms 33 are released from an overtube, trocar, or catheter prior to the release of proximal skirt 32 therefrom, such as described hereinbelow with reference to FIGS. 7A-C, 9A-G, and 16A-H. The fixation provided by inner engagement arms 33 holds prosthesis 10 in place until the implantation procedure is complete, such that blood flow against skirt 32 does not dislodge the prosthesis during the implantation procedure.

FIG. 3G is a schematic illustration of a fully-assembled valve prosthesis that includes inner engagement arms 33 of FIG. 3F, in accordance with an embodiment of the present invention. FIG. 7E, described hereinbelow, shows prosthesis 10 in situ having the configuration shown in FIG. 3F.

For some applications, the features shown in one or more of FIGS. 2A-B and 3A-G are combined. For example, valve support elements 122 and/or covering 124 may be provided for arms 22 of FIG. 3E. Other such combinations of features are within the scope of the present invention.

Figure 4A:
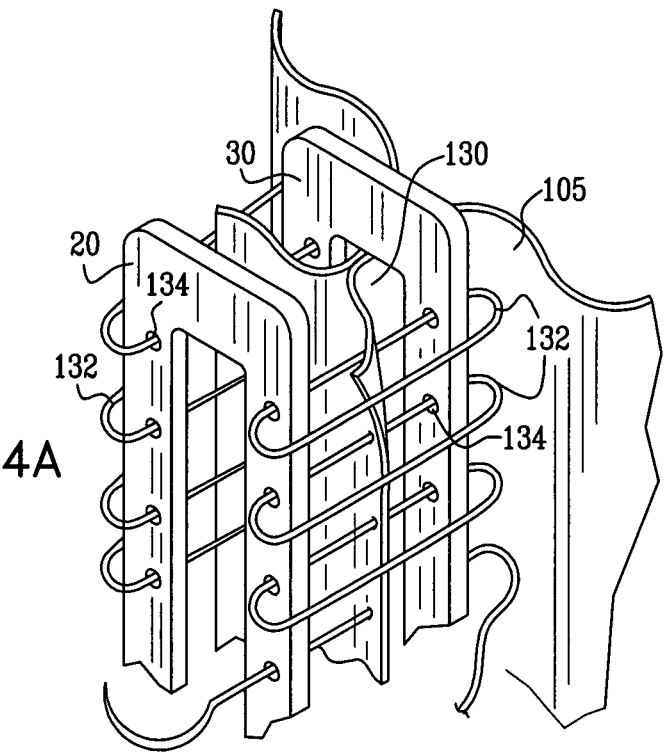
FIGS. 4A-C are schematic illustrations of configurations for coupling a pliant material to inner struts of the inner support structure of FIG. 2B and strut supports of the outer support structure of FIG. 2A, in accordance with respective embodiment of the present invention.
Figure 4B:
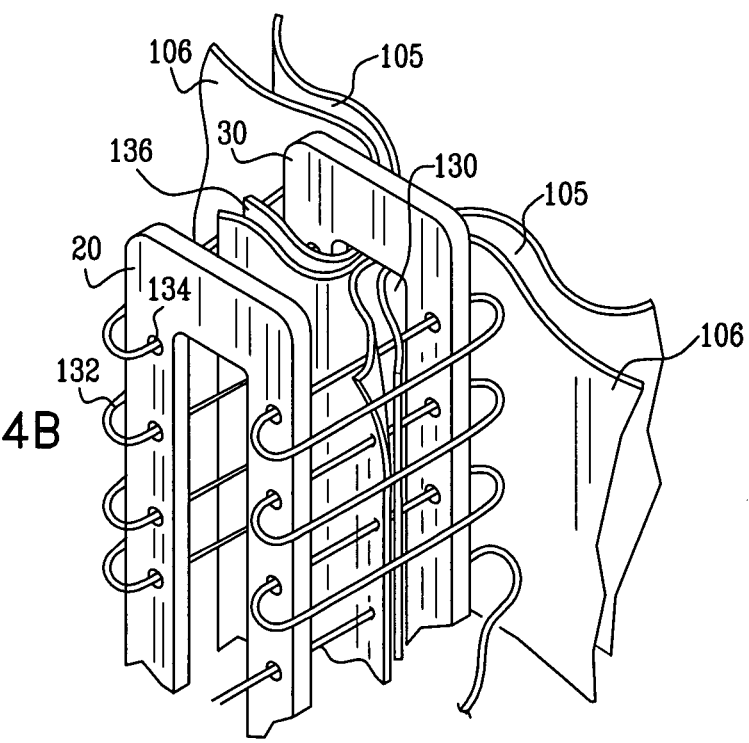
Figure 4C:
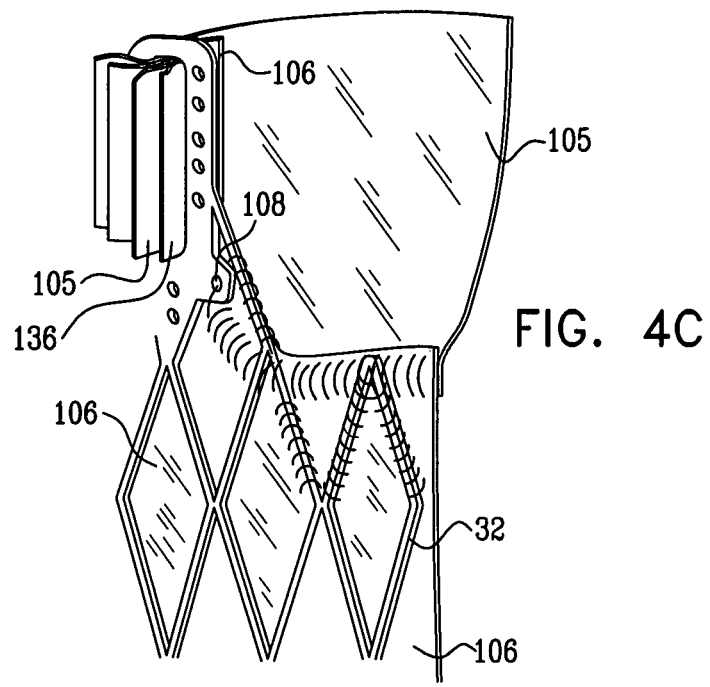

Reference is now made to FIGS. 4A-C, which are schematic illustrations of configurations for coupling pliant material 105 to inner struts 30 of inner support structure 12 and to strut supports 20 of outer support structure 14, in accordance with respective embodiments of the present invention.

In the configuration shown in FIG. 4A, valve 104 comprises a plurality of segments of pliant material 105, pairs of which are coupled together at respective interfaces between one of inner struts 30 and one of strut supports 20. Inner strut 30 is shaped so as to define an elongated slit 130. During manufacture of valve prosthesis 10, edges of two pieces of pliant material 105 are inserted through slit 130 such that a portion of each of the pieces of pliant material is sandwiched between inner strut 30 and strut support 20. The inner strut and strut support are tightly coupled together, such as by passing one or more sutures 132 through holes 134 defined by inner strut 30 and strut support 20. Sutures 132 typically couple the strut and strut support together such that pliant material 105 is supported on both sides thereof, thereby forming a strain relief which reduces stresses on the leaflets of valve 104 at the sutures. The relatively large surface areas of inner strut 30 and strut support 20 distribute the stress applied at pliant material 105, so that this stress is not applied primarily around holes 134. Typically, the edges of slit 130 are rounded in order to avoid damage to pliant material 105.

In the configuration shown in FIGS. 4B-C, portions 136 of graft covering 106 (including, optionally, pericardium or any suitable supple synthetic or biological material) are inserted through slit 130, between the edges of the slit and the two pieces of pliant material. The portions of the graft covering reduce friction between the pliant material and inner strut 30. As can be seen in FIG. 4C, portions 136 of graft covering 106 are typically integral with the rest of graft covering 106 (which is sewn to skirt 32). Graft covering 106 (including, optionally, pericardium or any suitable supple synthetic or biological material) is thus shaped so as to define distally protruding portions 136.

Figure 4D:
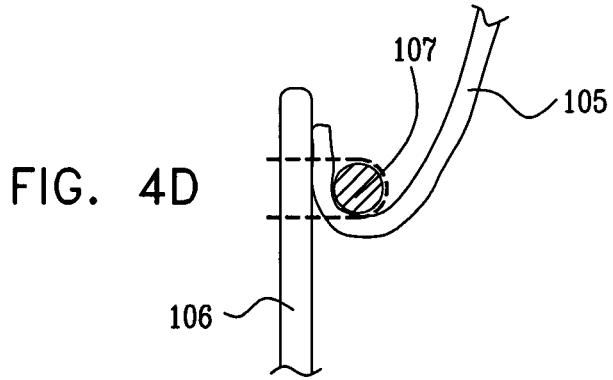
FIGS. 4D and 4E are side-view schematic illustrations of configurations for coupling the pliant material of FIGS. 4A-C to a graft covering, in accordance with respective embodiments of the present invention.
Figure 4E:
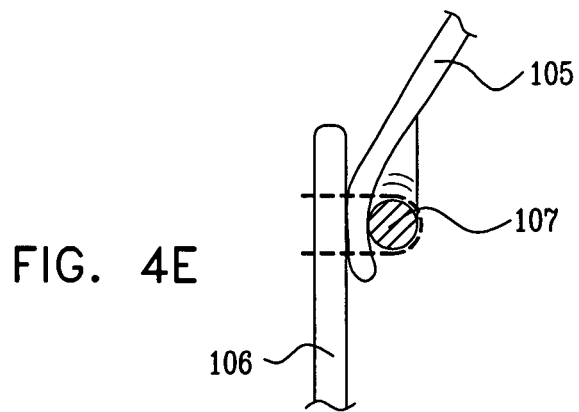

FIGS. 4D and 4E are side-view schematic illustrations of two configurations for coupling pliant material 105 to graft covering 106, and reducing leaflet stress during valve opening (FIG. 4D) or valve closure (FIG. 4E), in accordance with respective embodiments of the present invention. In both of these configurations, graft covering 106 is sewn to a cord 107, such that a portion of pliant material 105 is held between the cord and the graft covering. Cord 107 passes through a hole 108 (FIG. 4C) passing through or near one of the commissural posts (configuration not shown).

Reference is now made to FIGS. 5A-8A, which illustrate apparatus and a method for implanting valve prosthesis 10 in a native stenosed valve 140 of a heart 142, in accordance with respective embodiments of the present invention.

Figure 5A:
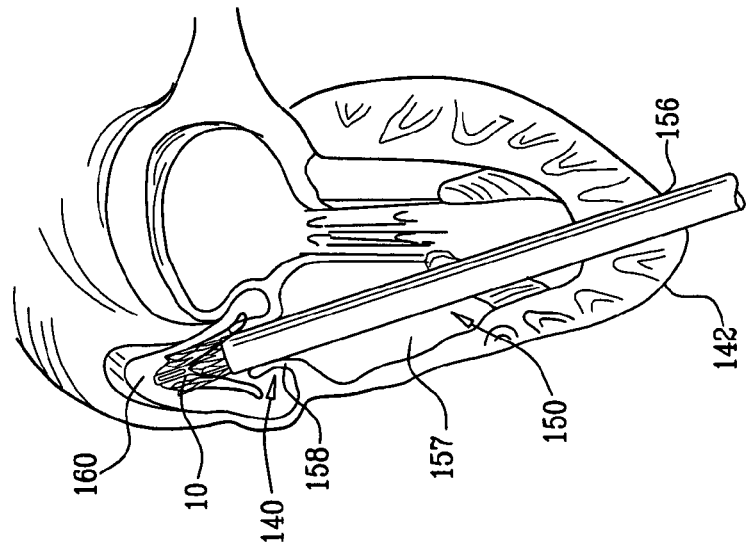
Figure 5B:
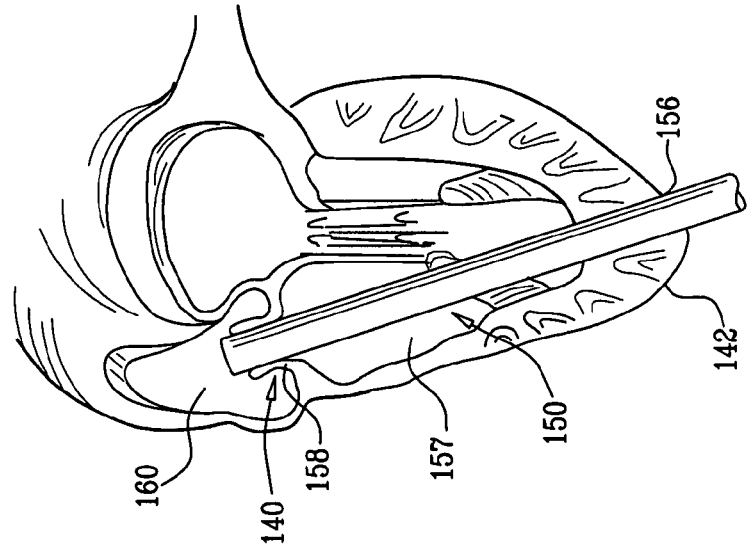
Figure 5C:
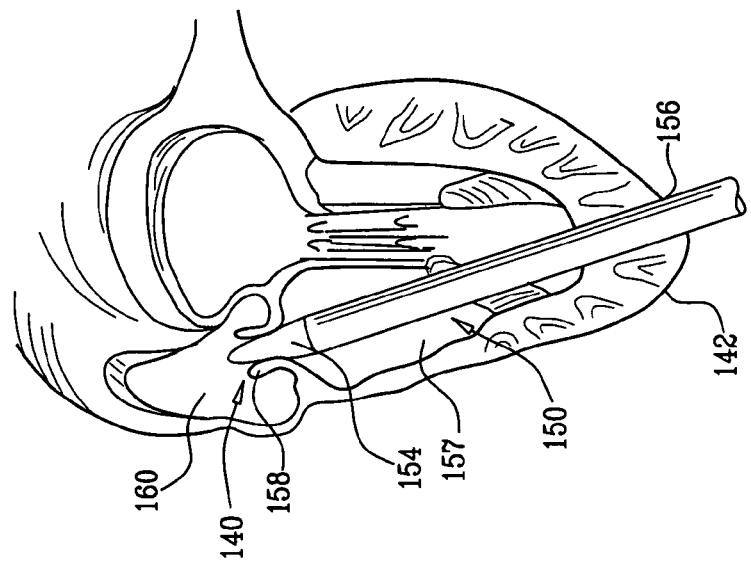

FIGS. 5A-C illustrate an overtube or trocar 150 and the initial steps of the implantation method, in accordance with respective embodiments of the present invention. Overtube or trocar 150 is placed over a dilator 154. As shown in FIG. 5A, overtube or trocar 150 is typically inserted through an apex 156 of heart 142, and advanced into a left ventricle 157 where its motion is terminated, or through left ventricle 157 until the distal end of dilator 154 passes native aortic valve leaflets 158. For example, apex 156 may be punctured using a standard Seldinger technique, and a guidewire may be advanced into an ascending aorta 160. Optionally, native aortic valve 140 is partially dilated to about 15-20 mm (e.g., about 16 mm), typically using a standard valvuloplasty balloon catheter. (In contrast, full dilation would be achieved utilizing dilation of 20 mm or more.) Overtube or trocar 150 is advanced into the ascending aorta. Overtube or trocar 150 is pushed beyond aortic valve 140 such that the distal end of overtube or trocar 150 is located above the highest point of native aortic valve 140. Dilator 154 is removed while overtube or trocar 150 remains in place with its distal end located above aortic valve 140, as shown in FIG. 5B. It is to be understood that the procedure may be modified so that overtube or trocar 150 is placed within the left ventricle and remains within the left ventricle throughout the entire implantation procedure. Valve prosthesis 10 is advanced through the distal end of overtube or trocar 150 into ascending aorta 160 distal to native leaflets 158, as shown in FIG. 5C. Typically, to facilitate this advancement, prior to the implantation procedure valve prosthesis 10 is loaded into a delivery tube 202, such as described hereinbelow with reference to FIGS. 12A-13D. During the implantation procedure, delivery tube 202 is advanced through overtube or trocar 150, thereby advancing the valve prosthesis through the overtube or trocar.

FIGS. 6A-B show an implantation of valve prosthesis 10 in ascending aorta 160, in accordance with an embodiment of the present invention. As mentioned above with reference to FIGS. 5A-C, the distal end of overtube or trocar 150 is positioned past native valve leaflets 158. The distal end of valve prosthesis 10 is advanced out of overtube or trocar 150 until engagement arms 22 exit overtube or trocar 150 and snap or spring open, as shown in FIG. 6A. Overtube or trocar 150 is gently pulled back until engagement arms 22 are brought into aortic sinuses 164. For some applications, overtube or trocar 150 and/or valve prosthesis 10 are gently rotated as indicated by arrows 166 in order to align engagement arms 22 with respective aortic sinuses 164. Although not typically necessary, fluoroscopic, ultrasound, or other surgical imaging techniques may be used to aid in this positioning. Overtube or trocar 150 and valve prosthesis 10 are pulled back slightly, such that engagement arms 22 are positioned within respective aortic sinuses 164, as shown in FIG. 6B. (Although engagement arms 22 are shown in FIG. 6B as being in contact with the sinus floors, for some applications the engagement arms do not come in contact with the sinus floors, such as described hereinbelow with reference to FIG. 7B.) Typically, valve prosthesis 10 is configured such that when engagement arms 22 are placed properly within aortic sinuses 164, outer strut supports 20 are aligned with commissures 170 (see, for example, FIG. 8A), thus preventing any possible obstruction of coronary ostia 116 by valve prosthesis 10. At this point in the implantation procedure, the distal end of valve prosthesis 10 is free of overtube or trocar 150, and the proximal end of prosthesis 10 remains in overtube or trocar 150.

For some applications, the use of imaging techniques is not necessary. The careful pulling back of valve prosthesis 10, without application of excessive force, generally causes each of engagement arms 22 to automatically self-align with a respective aortic sinus 164, because outer support structure 14, particularly engagement arms 22, generally matches the three-dimensional shape of aortic valve 140. If one of engagement arms 22 comes in contact with a commissure 170 during the careful pulling back of the prosthesis, the arm slides down the slope of the leaflet into the aortic sinus. Typically, arms 22 are evenly distributed around valve prosthesis 10 with a separation of 120 degrees between arms, such that all three arms naturally fall into place in respective sinuses upon even just one of the engagement arms achieving proper alignment with a sinus. This natural alignment generally occurs even if the sinuses themselves are not perfectly distributed at 120 degrees from one another.

This alignment process generally ensures positioning of the prosthetic leaflets within the aortic sinuses, thus exposing the prosthetic leaflets to natural blood vortex formation in the aortic sinuses, which contributes to early closure of the prosthetic leaflets, thus reducing closing volume (i.e., leakage through the prosthetic leaflets before fully closing), as well as promoting low-impact closure of the prosthetic leaflets, which typically reduces leaflet wear.

For some applications, a correct rotational disposition of the prosthesis with respect to the aortic valve site is determined by the surgeon based on tactile feedback.

Reference is now made to FIGS. 7A-E, which illustrate valve prosthesis 10 in situ upon completion of the implantation procedure, in accordance with respective embodiments of the present invention. After valve prosthesis 10 is placed properly within native stenosed valve 140, as described hereinabove with reference to FIGS. 5A-6B, the proximal end of valve prosthesis 10 is released from overtube or trocar 150, by withdrawing overtube or trocar 150. Proximal skirt 32 snaps or springs open to at least partially engage, with its proximal portion 34, the left-ventricular side of native valve 140, including at least a portion of an inner surface of an LVOT 180. As a result, valve prosthesis 10 forms an axial engagement system above and below native valve annulus 182 of native valve 140, which axially sandwiches a native valve complex (as defined hereinbelow with reference to FIG. 15) from the aortic and left-ventricular sides thereof. Native valve leaflets 158 are captured between proximal skirt 32 and engagement arms 22, typically without applying force along the longitudinal axis of the leaflets, in order to avoid shortening of the length of the leaflets, or forced bending, crimping, or folding over of the leaflets. For some applications, barbs 120, if provided, pierce aortic annulus 182 on the left-ventricular side of native valve 140, while for other applications, the barbs are blunt, in which case they generally protrude into the tissue of the aortic annulus, without piercing the tissue. For some applications, support structure 14 is configured to elevate native valve leaflets 158 from within the aortic sinuses.

Figure 7A:
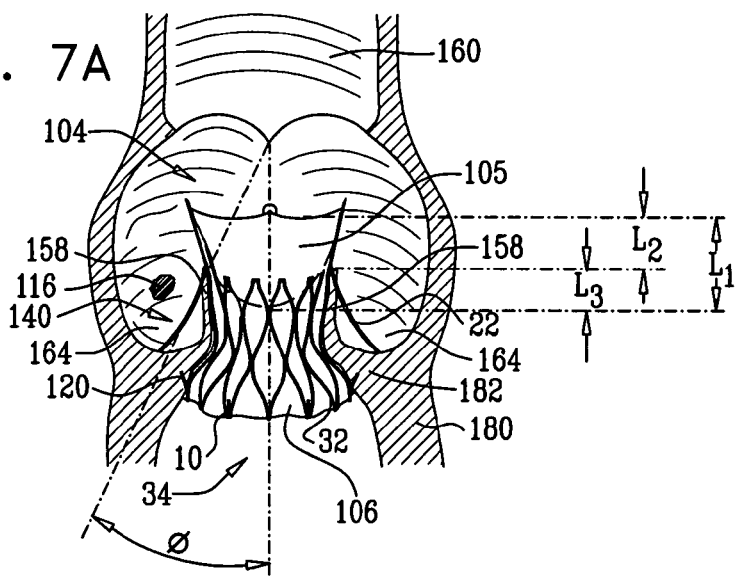
Figure 7B:
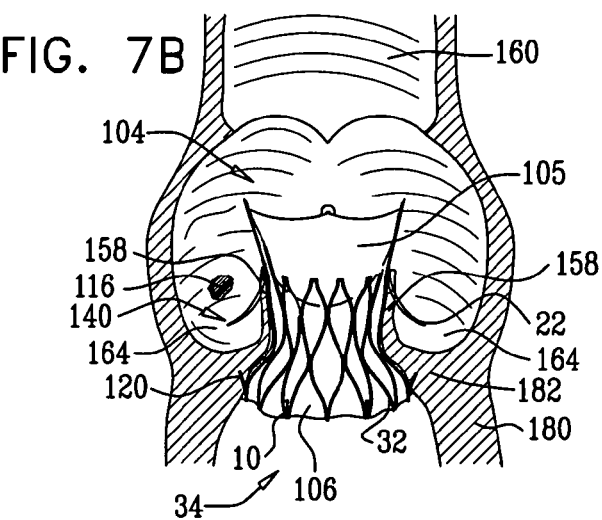
Figure 7C:
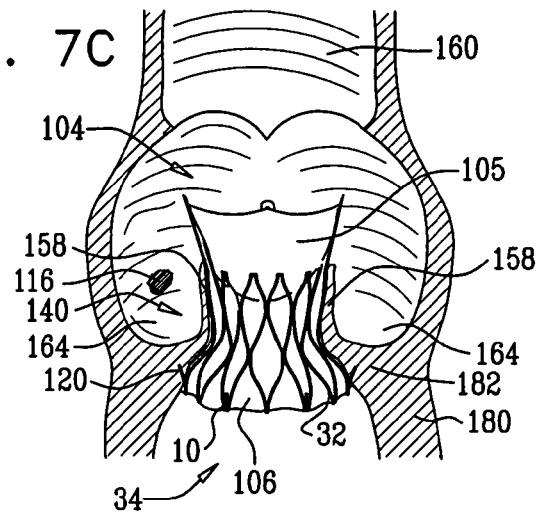

In the embodiment shown in FIG. 7A, upon the completion of the implantation of prosthesis 10, engagement arms 22 are positioned within aortic sinuses 164, such that the ends of the engagement arms touch the floors of the sinuses. Although the ends of the engagement arms are shown touching approximately the radial center of the floors of the sinuses, for some applications, the ends of the engagement arms touch the floors further from leaflets 158 or closer to the leaflets, or touch the body of the leaflets, the roots of the leaflets, or the transition between the sinuses and the leaflet roots. Alternatively, the engagement arms are shorter, such as shown in FIG. 7B, such that they do not reach the floors of the sinuses. Further alternatively, for some applications prosthesis 10 does not comprise arms 22, as shown in FIG. 7C.

In the embodiment shown in FIG. 7D, prosthesis 10 has been implanted after the native valve leaflets have been excised, in accordance with an embodiment of the present invention.

The embodiment illustrated in FIG. 7E shows valve prosthesis 10 in situ having the configuration of outer support structure 14 described hereinabove with reference to FIG. 3F.

For some applications, barbs 120 are coated or otherwise provided with a surface property for enhancing their attachment to tissue of aortic annulus 182. Graft covering 106 of proximal skirt 32 also helps prevent regurgitation and device migration.

For some applications, the positioning of arms 22 prior to the opening of proximal skirt 32 prevents native valve leaflets 158 from opening more than a predetermined desired amount. The support provided by arms 22 to the valve leaflets limits the subsequent opening of the leaflets by the proximal skirt. The desired amount of opening is determined at least in part by the angle between arms 22 and a central longitudinal axis of the prosthesis (shown, for example, as angle θ in FIG. 7A). Typically, the angle is between about 1 and about 89 degrees, such as between about 10 and about 60 degrees, such as 25 degrees, or between about 25 and about 65 degrees. Typically, the angle is predetermined. For some applications, the fixation members of prosthesis 10 are configured to prevent opening of the native leaflets to their maximum diameter.

Reference is again made to FIG. 7A. For some applications, prosthetic distal valve 104 is coupled to strut supports 20 and/or inner struts 30 of prosthesis 10 (see, for example, FIG. 1), such that at least 50% of an axial length of the prosthetic leaflets is distal to native valve leaflets 158. In other words, if prosthetic distal valve 104 has an axial length L1, a portion L2 of length L1 that is distal to leaflets 158 is greater than a portion L3 of length L1 that is proximal to leaflets 158.

FIG. 8A shows valve prosthesis 10 in situ upon completion of the implantation procedure, as viewed from ascending aorta 160, upon placement of engagement arms 22 within respective aortic sinuses 164, in accordance with an embodiment of the present invention. In this embodiment, engagement arms 22 are positioned within aortic sinuses 164, such that the ends of the engagement arms touch the floors of the sinuses, for example as described hereinabove with reference to FIG. 7A.

FIG. 8B shows valve prosthesis 10 in situ upon completion of the implantation procedure, in accordance with an embodiment of the present invention. In this embodiment, junctures 24 between pairs of engagement arms 22 ride above respective native commissures 170, without impinging on the commissures (i.e., touching or pushing the commissures). In other words, there is a gap between each of junctures 24 and its respective native commissure 170. Engagement arms 22 are positioned within aortic sinuses 164, such that the ends of the engagement arms touch the floors of the sinuses. In this embodiment, the number of engagement arms 22 is typically equal to the number of aortic sinuses 164 of the native valve, and the engagement arms are radially separated by approximately equal angles. The three-dimensional shape of engagement arms 22 causes the ends of the engagement arms to find the lowest point of reach within the floors of the sinuses, thereby enabling self-alignment of prosthesis 10 with the native aortic valve site and commissures 170.

A length L (parallel to a longitudinal axis of prosthesis 10) between (a) each juncture 24 and (b) the contact point of respective engagement arm 22 to the sinus floor is typically greater than about 6 mm, e.g., greater than about 10 mm, or than about 13 mm. For some applications, length L is between about 10 and about 18 mm, e.g., about 13 mm.

In typical human subjects, the native valve complex has three native commissures 170, which define respective commissural high points, and three respective sinus low points. Prosthesis 10 is configured to match these high and low points. Such matching enables axial anchoring, without forced bending, crimping, or folding over of the leaflets, and without impinging on the commissures. In this way, prosthesis 10 embraces the leaflets, rather than squeezing them.

For some applications, engagement arms 22 are generally aligned with the native leaflets, thereby avoiding local deformation, and distributing force over a larger contiguous area of the leaflet surface.

FIG. 8C shows valve prosthesis 10 in situ upon completion of the implantation procedure, in accordance with an embodiment of the present invention. In this embodiment, junctures 24 between pairs of engagement arms 22 ride above respective native commissures 170, impinging on the commissures (i.e., touching or pushing the commissures). Engagement arms 22 are positioned within aortic sinuses 164, such that the ends of the engagement arms do not reach the floors of the sinuses (such as described hereinabove with reference to FIG. 7B). The three-dimensional shape of junctures 24 causes the junctures to align with commissures 170, thereby enabling self-alignment of prosthesis 10 with the native aortic valve site and commissures 170. In an embodiment (not shown), junctures 24 apply axial force to (i.e., push) the commissures, and engagement arms 22 apply axial force to aortic sinuses 164.

Figure 9A:
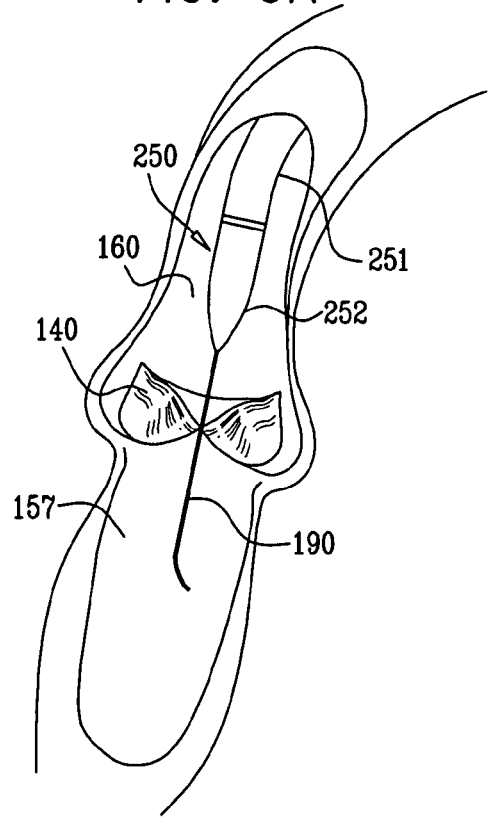
FIGS. 9A-G schematically illustrate a transaortic approach for implanting the valve prosthesis of FIG. 1, in accordance with an embodiment of the present invention.
Figure 9B:
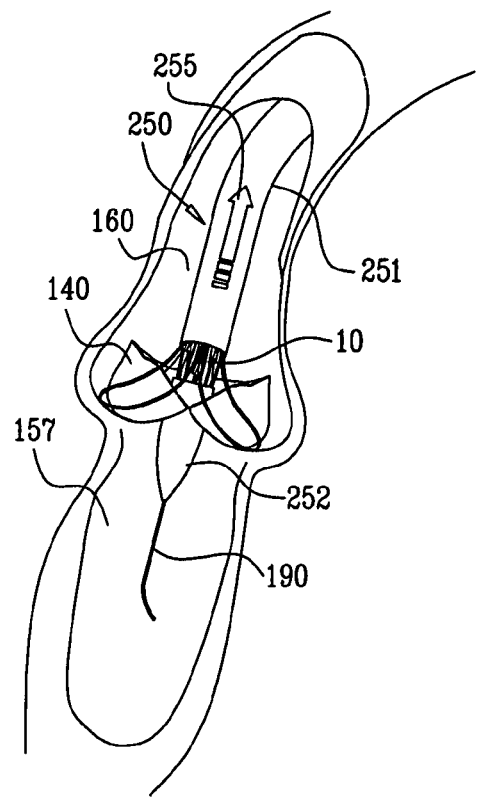
Figure 9C:
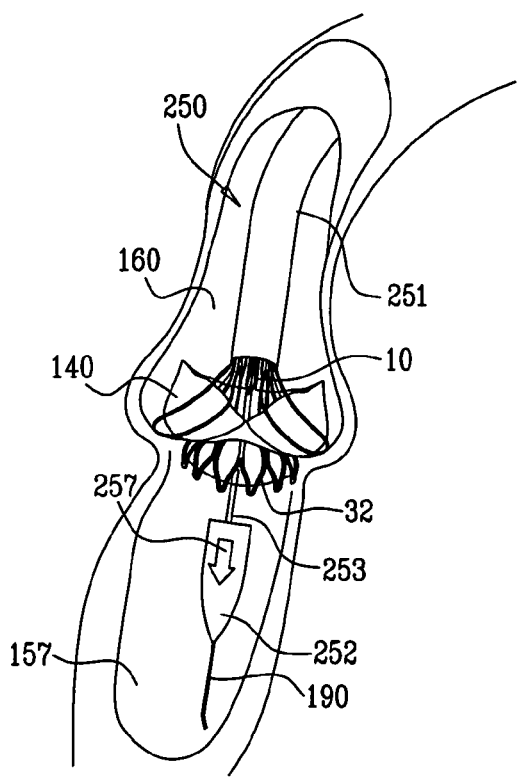
Figure 9D:
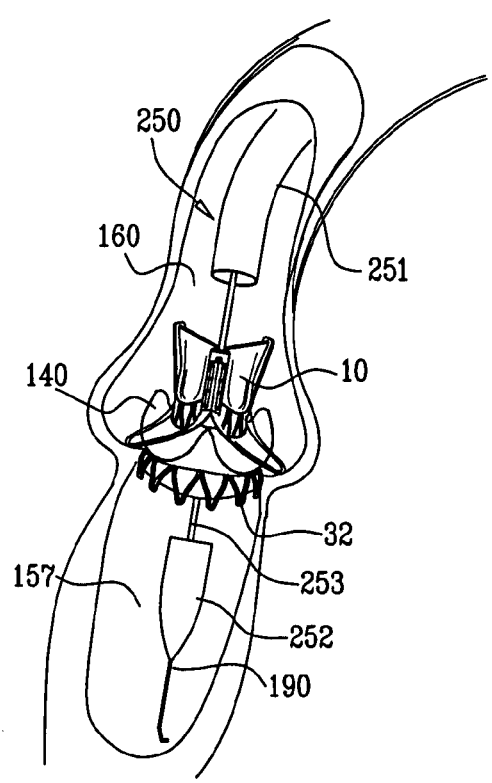
Figure 9E:
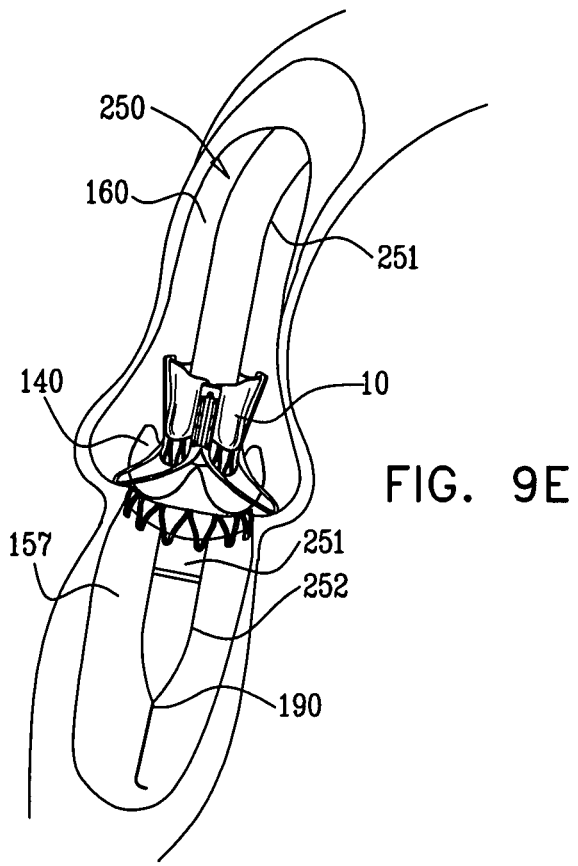
Figure 9F:
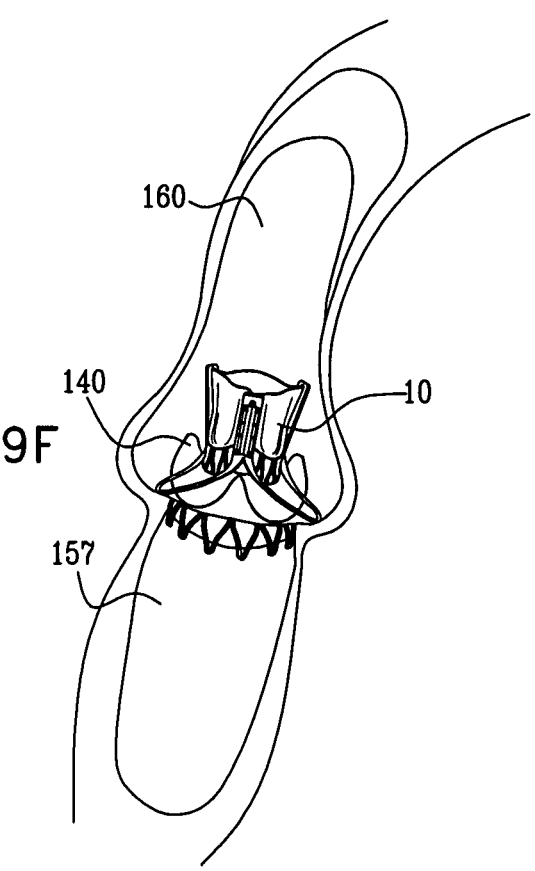
Figure 9G:
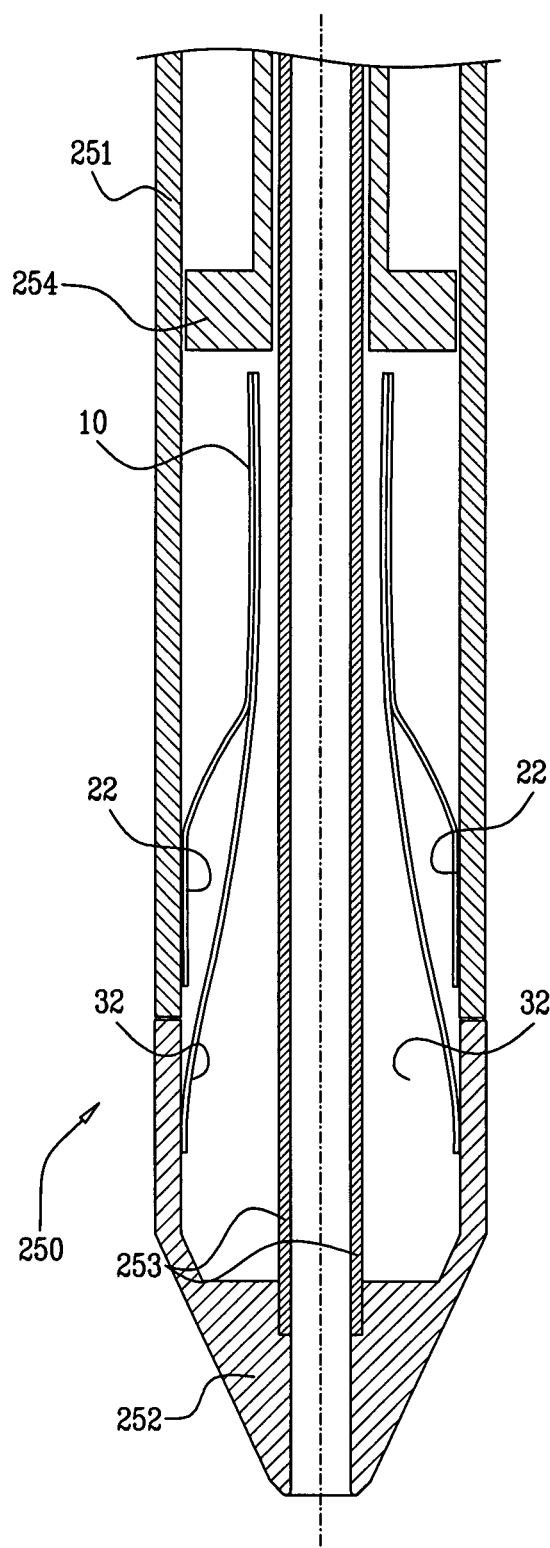

Reference is made to FIGS. 9A-G, which schematically illustrate a retrograde transaortic approach for implanting valve prosthesis 10, in accordance with an embodiment of the present invention. Prior to the implantation procedure, prosthesis 10 is positioned in a retrograde delivery catheter 250, as shown in FIG. 9G. A retrograde delivery catheter tube 251 of catheter 250 holds engagement arms 22, and a delivery catheter cap 252 holds proximal skirt 32.

The implantation procedure begins with the transaortic insertion of a guidewire 190 into left ventricle 157, as shown in FIG. 9A. Optionally, stenotic aortic valve 140 is partially dilated to about 15-20 mm (e.g., about 16 mm), typically using a standard valvuloplasty balloon catheter. (In contrast, full dilation would be achieved by using a balloon catheter with a diameter of 20 mm or more.) Retrograde delivery catheter 250 is advanced over guidewire 190 into ascending aorta 160 towards native aortic valve 140, as shown in FIG. 9A. As shown in FIG. 9B, retrograde delivery catheter 250 is advanced over guidewire 190 until delivery catheter cap 252 passes through native aortic valve 140 partially into left ventricle 157. As also shown in FIG. 9B, retrograde delivery catheter tube 251 is pulled back (in the direction indicated by an arrow 255), while a device stopper 254 (shown in FIG. 9G) prevents valve prosthesis 10 within tube 251 from being pulled back with tube 251, so that engagement arms 22 are released and flare out laterally into the sinuses. At this stage of the implantation procedure, proximal skirt 32 of prosthesis 10 remains in delivery catheter cap 252.

As shown in FIG. 9C, at the next step of the implantation procedure, delivery catheter cap 252 is pushed in the direction of the apex of the heart (as shown by an arrow 257), using a retrograde delivery catheter cap shaft 253 that passes through tube 251 and prosthesis 10. This advancing of cap 252 frees proximal skirt 32 to snap or spring open, and engage the inner surface of LVOT 180. Barbs 120, if provided, pierce or protrude into the aortic annulus on the left-ventricular side of the native valve. Retrograde delivery catheter tube 251 is further pulled back until the rest of valve prosthesis 10 is released from the tube, as shown in FIG. 9D.

Retrograde delivery catheter tube 251 is again advanced over shaft 253 toward the apex of the heart, until tube 251 rejoins cap 252, as shown in FIG. 9E. Retrograde delivery catheter 250 and guidewire 190 are withdrawn from left ventricle 157, and then from ascending aorta 160, leaving prosthesis 10 in place, as shown in FIG. 9F.

FIGS. 10A and 10B show valve prosthesis 10 in open (systolic) and closed (diastolic) positions, respectively, in accordance with an embodiment of the present invention. For clarity of illustration, the surrounding anatomy is not shown in the figure. Collapsible pliant material 105 of valve 104 opens during systole and closes during diastole, because of the fluid forces applied thereto by the blood flow and the pressure difference between the left ventricle and the aorta. Alternatively, valve 104 comprises one or more rigid components, such as rigid leaflets, for example as described in U.S. Pat. No. 6,312,465 to Griffin et al. or U.S. Pat. No. 5,908,451 to Yeo, both of which are incorporated herein by reference. Although prosthesis 10, including valve 104, is shown in the figures as defining a single flow field therethrough, for some applications the prosthesis and valve are configured so as to define a plurality of flow fields therethrough, such as shown in several figures of the '451 patent to Yeo (e.g., FIGS. 1-3 thereof).

Reference is made to FIGS. 11A-D, which illustrate several configurations for axially coupling valve prosthesis 10 to aortic annulus 182, in accordance with respective embodiments of the present invention. For clarity of illustration, these figures show a spread view of the native valve, viewed from a central axis of the native valve, with native aortic valve leaflets 158 cut longitudinally and pulled to the sides.

Figure 11A:
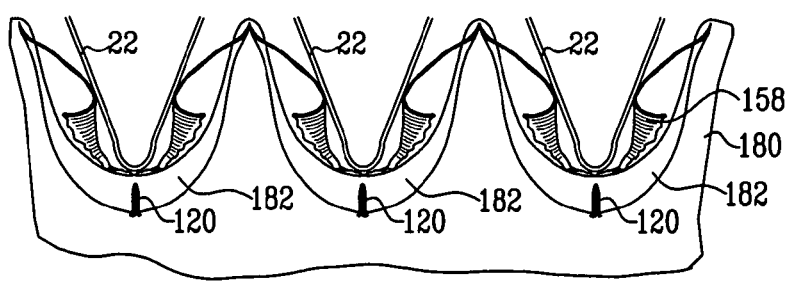
FIGS. 11A-D illustrate several configurations for axially coupling the valve prosthesis of FIG. 1 to the aortic annulus, in accordance with respective embodiments of the present invention.
Figure 11B:
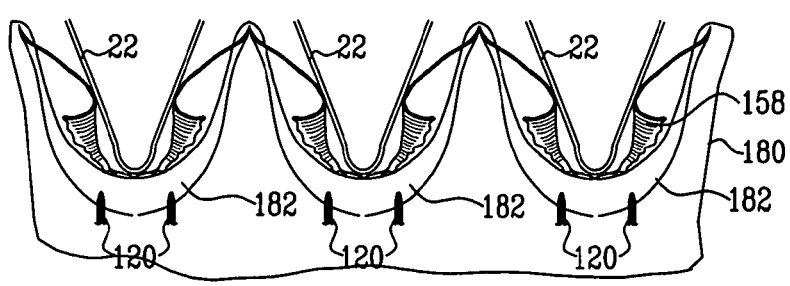

In the configuration shown in FIG. 11A, proximal skirt 32 of valve prosthesis 10 is shaped so as to define a single barb 120 for each leaflet 158, such that the barbs are generally centered with respect to the leaflets and engagement arms 22. In the configuration shown in FIG. 11B, the proximal skirt is shaped so as to define a pair of barbs 120 for each leaflet 158.

Figure 11C:
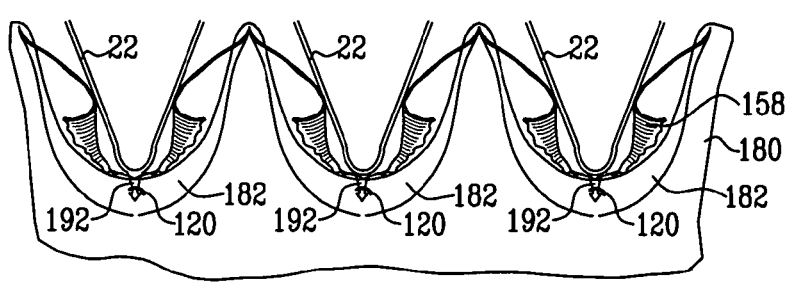

In the configuration shown in FIG. 11C, each engagement arm 22 comprises at least one proximal spike 192, which typically protrudes from a most proximal region of the engagement arm (i.e., the portion of the engagement arm closest to the apex of the heart). Spikes 192 penetrate aortic annulus 182 from the aortic side, until the spikes exit the annulus on the left-ventricular side, and engage respective barbs 120 on the left-ventricular side.

Figure 11D:
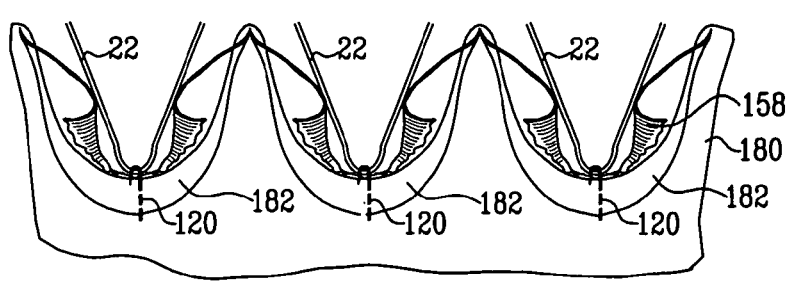

In the configuration shown in FIG. 11D, barbs 120 penetrate aortic annulus 182 from the left-ventricular side thereof, until the barbs exit the annulus on the aortic side, and are coupled to respective engagement arms 22 in respective sinuses. For example, the ends of the barbs may be shaped as hooks, in order to hook around proximal regions of engagement arms 22.

Reference is made to FIGS. 12A-G, which illustrate a holding device 200 for holding valve prosthesis 10 prior to the implantation of the prosthesis, in accordance with an embodiment of the present invention. Valve prosthesis 10 is loaded into delivery tube 202 from holding device 200, as is described hereinbelow with reference to FIGS. 13A-D. During an implantation procedure, delivery tube 202 is advanced into an overtube or trocar, such as overtube or trocar 150, described hereinabove with reference to FIGS. 5A-C.

Figure 12A:
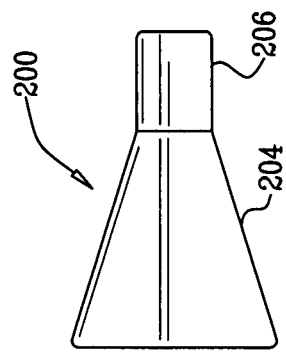
FIGS. 12A-G illustrate a holding device for holding the valve prosthesis of FIG. 1 prior to the implantation of the prosthesis, in accordance with an embodiment of the present invention.
Figure 12B:
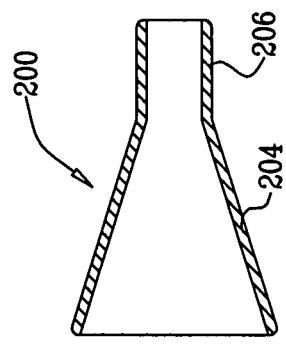

FIGS. 12A and 12B illustrate outer and sectional views, respectively, of holding device 200, in accordance with an embodiment of the present invention. For some applications, holding device 200 is shaped so as to define a conical portion 204 and a tubular portion 206. Holding device 200 comprises, for example, plastic.

Figure 12C:
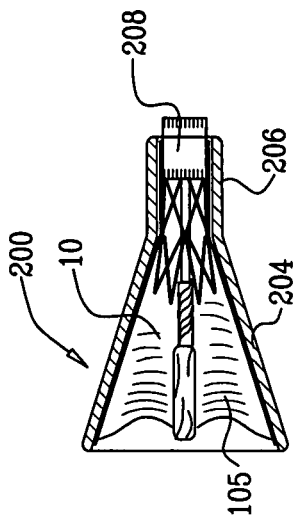

FIG. 12C shows valve prosthesis 10 loaded in holding device 200, in accordance with an embodiment of the present invention. The proximal end of valve prosthesis 10 is typically fully compressed within tubular portion 206, while collapsible pliant material 105 is in at least a partially open position within conical portion 204, so as not to deform the typically delicate material of the valve. The proximal end of the prosthesis is optionally coupled to a device holder 208.

Figure 12D:
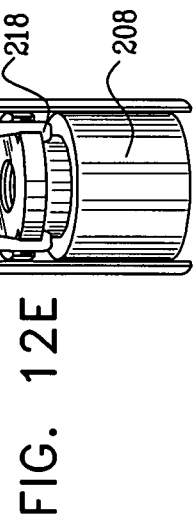
Figure 12E:
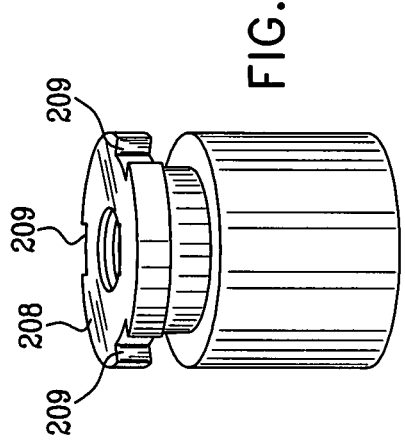

FIGS. 12D and 12E show a configuration of device holder 208, in accordance with an embodiment of the present invention. In this configuration, device holder 208 is shaped so as to define one or more female coupling openings 209, to which corresponding male coupling members 218 of valve prosthesis 10 are releasably coupled. For example, proximal portion 34 of proximal skirt 32 (FIGS. 1 and 2B) may be shaped so as to define male coupling members 218. (For clarity of illustration, proximal skirt 32 is not shown in FIG. 12E.) For some applications, the genders of the coupling elements are reversed.

Figure 12F:
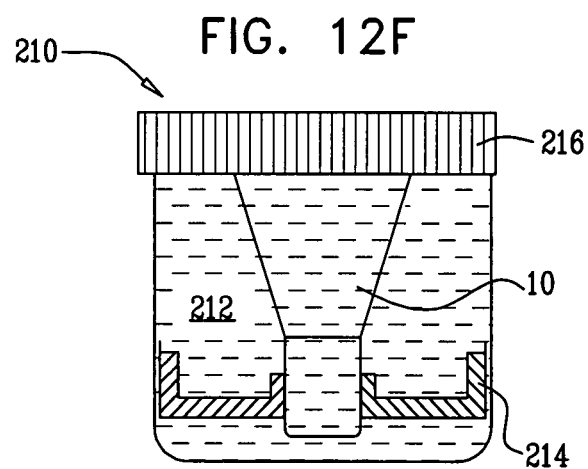

FIG. 12F illustrates holding device 200 in storage in a jar 210 containing a preservation fluid 212 such as glutaraldehyde solution. For some applications, holding device 200 is held upright by a holder 214. The contents of the holding device 200 are typically kept in preservation fluid 212 at all times, and jar 210 is sealed by a cover 216.

Figure 12G:
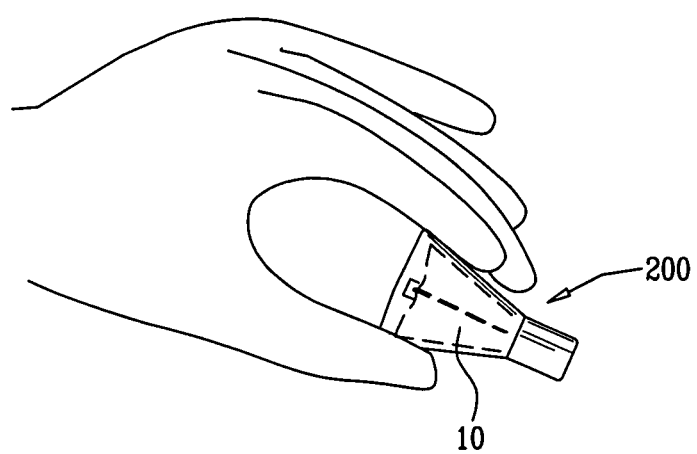

FIG. 12G illustrates the removal of holding device 200 from storage jar 210 prior to loading valve prosthesis 10 into delivery tube 202, in accordance with an embodiment of the present invention. Holding device 200 and its contents are typically washed prior to loading.

Reference is now made to FIGS. 13A-D, which illustrate the loading of valve prosthesis 10 into delivery tube 202 from holding device 200, in accordance with an embodiment of the present invention. As shown in FIG. 13A, a distal end of a central delivery shaft 222 includes a device holder connector 220. Device holder connector 220 is removably coupled to device holder 208, which is coupled (e.g., fixed) to valve prosthesis 10. For example, device holder connector 220 and device holder 208 may comprise mating, screw-threaded male and female connectors.

As shown in FIG. 13B, retraction, to the right in the figure, of central delivery shaft 222 pulls valve prosthesis 10, which is at least partially compressed, into delivery tube 202. As shown in FIG. 13C, valve prosthesis 10 is pulled into delivery tube 202. Valve prosthesis 10 is placed in delivery tube 202 such that engagement arms 22 extend from delivery tube 202, and thus are free to flare outwards radially, as shown in FIG. 13D. (The engagement arms are constrained from flaring outwards during the initial steps of an implantation procedure by an overtube or trocar into which delivery tube 202 is inserted, such as overtube or trocar 150, described hereinabove with reference to FIGS. 5A-C.)

Although valve prosthesis 10 has been generally described herein as being implantable in an aortic valve, in some embodiments of the present invention the valve prosthesis is configured to be placed in another cardiac valve, such as a mitral valve, tricuspid valve, or pulmonary valve (such as described hereinbelow with reference to FIG. 14), or in a venous valve. As used herein, including in the claims, "proximal" and "upstream" mean the side of the native or prosthetic valve closer to incoming blood flow, and "distal" and "downstream" mean the side of the native or prosthetic valve closer to outgoing blood flow.

Figure 14:
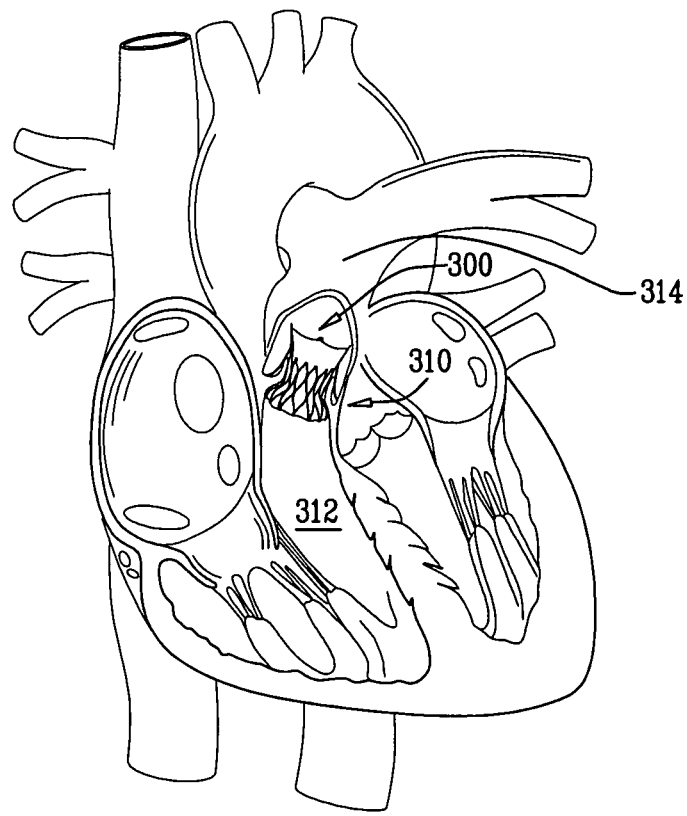
FIG. 14 is a schematic illustration of a valve prosthesis placed in a pulmonary valve, in accordance with an embodiment of the present invention.

Reference is made to FIG. 14, which is a schematic illustration of a fully-assembled valve prosthesis 300 placed in a pulmonary valve 310, in accordance with an embodiment of the present invention. Valve prosthesis 300 is generally similar to valve prosthesis 10, described herein with reference to FIGS. 1-13D and 16A-17, with appropriate modifications, such as size, for placement in pulmonary valve 310. Valve prosthesis 300 comprises two portions that are configured to axially sandwich the native pulmonary valve complex from right-ventricular 312 and pulmonary trunk 314 sides thereof.

Figure 15:
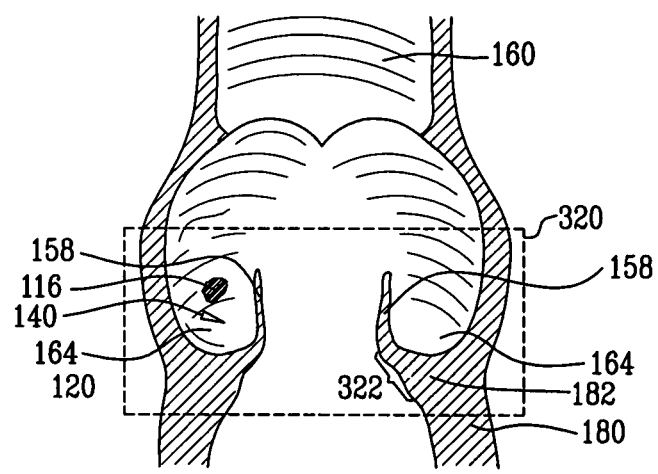
FIG. 15 is a schematic anatomical illustration showing the location of a native valve complex, in accordance with an embodiment of the present invention.

Reference is made to FIG. 15, which is a schematic anatomical illustration showing the location of a native valve complex, in accordance with an embodiment of the present invention. As used herein, including in the claims, the "native valve complex" includes the area demarcated by a box 320, which includes native aortic valve leaflets 158, native valve annulus 182, subvalvular tissue 322 on the left-ventricular side, and the lower half of the aortic sinuses 164 (i.e., up to the top of box 320).

Figure 16A:
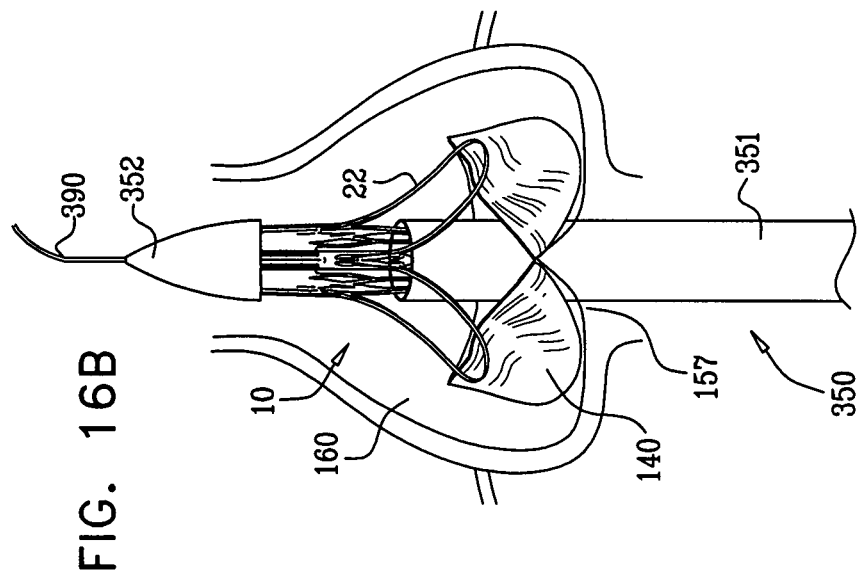
Figure 16B:
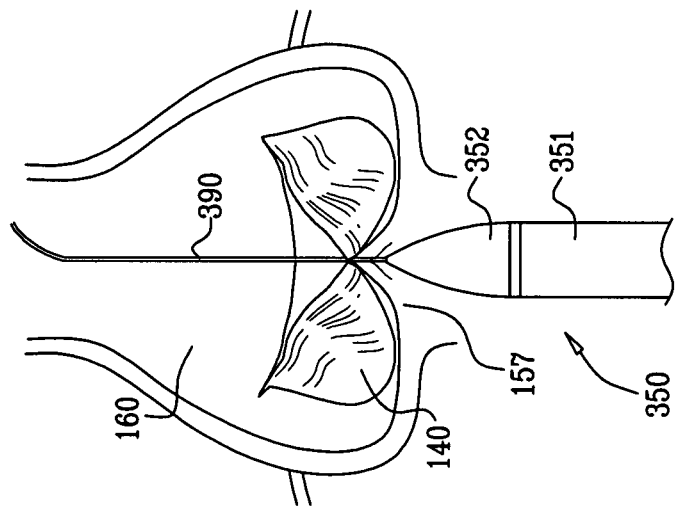
Figure 16H:
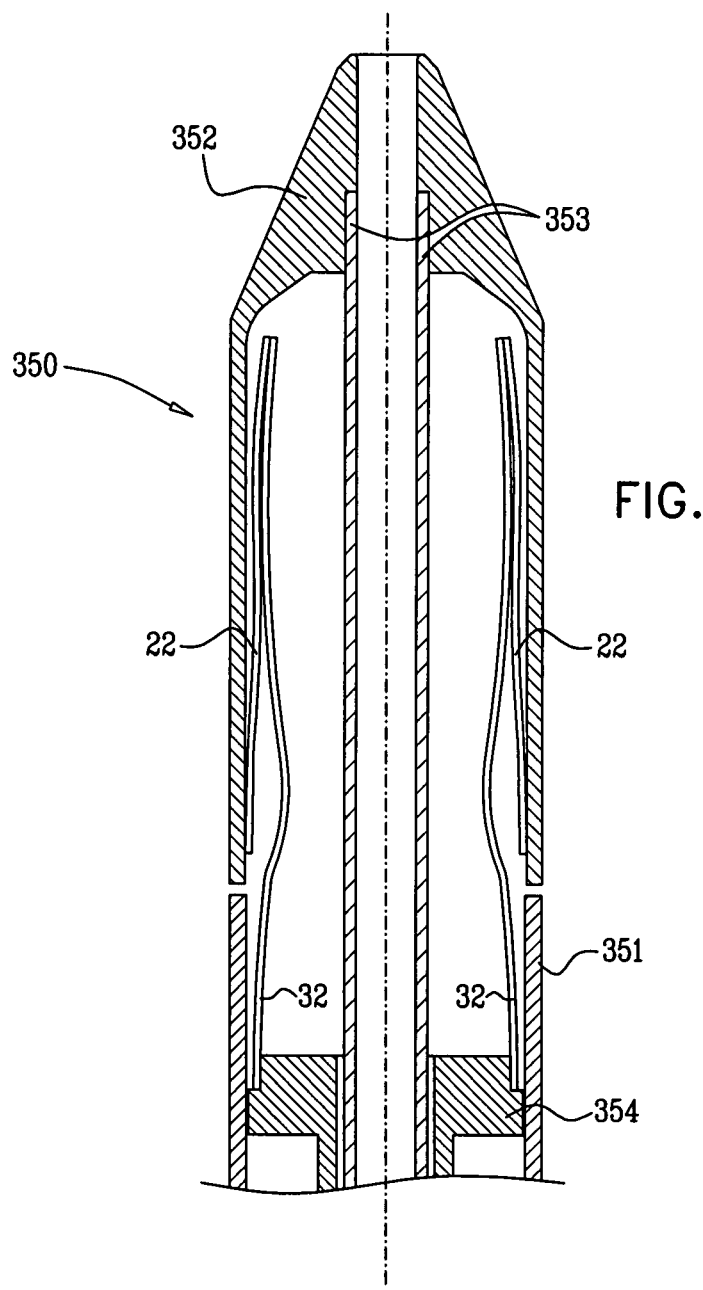

Reference is made to FIGS. 16A-H, which schematically illustrate another transapical technique for implanting valve prosthesis 10 (in addition to the transapical approach described hereinabove with reference to FIGS. 5A-8A), in accordance with an embodiment of the present invention. Prior to the implantation procedure, prosthesis 10 is positioned in a transapical delivery catheter 350, as shown in FIG. 16H. A transapical delivery tube 351 of catheter 350 holds proximal skirt 32, and a transapical delivery cap 352 holds the distal end of the valve.

The implantation procedure begins with insertion of catheter 350 through an apex of the heart, into left ventricle 157. For example, the apex may be punctured using a standard Seldinger technique. A guidewire 390 is advanced through catheter 350 into ascending aorta 160, as shown in FIG. 16A. Optionally, aortic valve 140 is partially dilated to about 15-20 mm (e.g., about 16 mm), typically using a standard valvuloplasty balloon catheter.

Catheter 350 is advanced over guidewire 390 through native aortic valve 140, into ascending aorta 160. Delivery cap 352 is advanced further into the ascending aorta, by pushing with delivery cap shaft 353. The advancement of the delivery cap releases engagement arms 22, which flare out laterally, as shown in FIG. 16B. Catheter 350 is withdrawn towards the ventricle, thereby positioning engagement arms 22 in the sinuses, as shown in FIG. 16C. (Although engagement arms 22 are shown in FIG. 16C as being in contact with the sinus floors, for some applications the engagement arms do not come in contact with the sinus floors, such as described hereinabove with reference to FIG. 7B.) At this stage of the implantation procedure, proximal skirt 32 remains in tube 351.

Alternatively, catheter 350 is placed within an overtube (not shown), similar to overtube or trocar 150 (FIGS. 5A-6B), and in such a configuration the engagement arms may be released either by pulling back of the overtube, or by the pushing forward of delivery end cap 352.

At the next step of the implantation procedure, tube 351 is withdrawn in the direction of the apex of the heart. Delivery cap shaft 353 prevents cap 352 from being withdrawn with tube 351 (FIG. 16H). As a result, proximal skirt 32 is freed from tube 351 to snap or spring open, and engage the inner surface of LVOT 180. Barbs 120, if provided, pierce or protrude into the aortic annulus on the left-ventricular side of the native valve. It is noted that cap 352 remains in place until after proximal skirt 32 opens. Blood flow thus cannot wash the skirt downstream during the implantation procedure.

Cap 352 is advanced further into the ascending aorta by pushing on delivery cap shaft 353, thereby releasing the rest of valve prosthesis 10 from cap 352, as shown in FIG. 16E. Delivery tube 351 is advanced over shaft 353 through aortic valve 140, until tube 351 rejoins cap 352, as shown in FIG. 16F. Delivery catheter 350 is withdrawn into the left ventricle, as shown in FIG. 16G, and then from the heart, along with guidewire 390. Prosthesis 10 is left in place, completing the implantation procedure.

Figure 17:
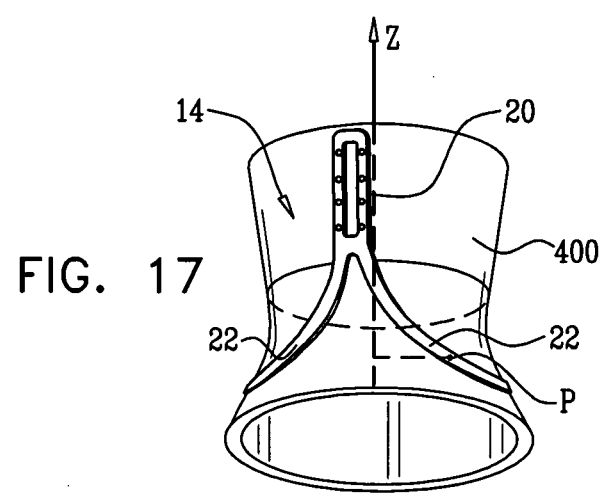
FIG. 17 is a schematic illustration showing a shape of engagement arms of an outer support structure of the prosthesis of FIG. 1, in accordance with an embodiment of the present invention.

Reference is made to FIG. 17, which is a schematic illustration showing a shape of engagement arms 22, in accordance with an embodiment of the present invention. In the figure, outer support structure 14 is shown placed on an abstract geometric form 400 for clarity of illustration of the shape of the structure. As can be seen, in this embodiment engagement arms 22 have a shape that is generally upwardly concave (except at the junctures), i.e., concave in a downstream direction. In mathematical terms, this shape can be characterized by the function $z''(r)>0$, where z is the height at any given point on one of engagement arms 22 (e.g., point P), and r is the distance from the z-axis to the given point. (It is understood that the arms may be shaped so as to include one or more relatively short sections that are upwardly convex (i.e., $z''(r)<0$), but that the general shape of the arms is upwardly concave.)

For some applications, engagement arms 22 are shaped such that at least a portion of the arms is parallel to the longitudinal axis of outer support structure 14.

In an embodiment, the shape of the arms is characterized by the function $z''(r)<=0$, i.e., the general shapes of the arms is not upwardly concave.

As used herein, including in the claims, the "ascending aorta" includes the aortic root (sinuses) and the tubular portion above the root.

Although valve prostheses 10 and 300 have been described herein as comprising a valve, for some applications the prostheses do not comprise valves.

The scope of the present invention includes embodiments described in the following applications, which are assigned to the assignee of the present application and are incorporated herein by reference. In an embodiment, techniques and apparatus described in one or more of the following applications are combined with techniques and apparatus described herein:

U.S. patent application Ser. No. 11/024,908, filed Dec. 30, 2004, entitled, "Fluid flow prosthetic device," which published as US Patent Application Publication 2006/0149360;

International Patent Application PCT/IL2005/001399, filed Dec. 29, 2005, entitled, "Fluid flow prosthetic device," which published as PCT Publication WO 06/070372; and/or International Patent Application PCT/IL2004/000601, filed Jul. 6, 2004, entitled, "Implantable prosthetic devices particularly for transarterial delivery in the treatment of aortic stenosis, and methods of implanting such devices," which published as PCT Publication WO 05/002466, and U.S. patent application Ser. No. 10/563,384, filed Apr. 20, 2006, in the national stage thereof, which published as US Patent Application Publication 2006/0259134.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus comprising a prosthesis for implantation at a native semilunar valve of a native valve complex of a subject, the prosthesis comprising:
   a distal fixation member including exactly three engagement arms, wherein each of the engagement arms is configured to extend into a respective sinus of a heart when the prosthesis is implanted in a native valve complex, wherein the distal fixation member has an upstream end and a downstream end, the upstream end being configured to be positioned closer to a ventricle of a subject when the prosthesis is implanted in a subject, and wherein the distal fixation member is configured to apply a first axial force directed toward a ventricle of the subject;
   a proximal fixation member coupled to the distal fixation member, the proximal fixation member configured to be positioned at least partially on a ventricular side of a native valve complex, and to apply a second axial force directed toward the downstream artery, such that application of the first and second forces couples the prosthesis to the native valve complex by axially sandwiching the native valve complex from a downstream side and the ventricular side thereof; and
   a replacement cardiac valve, wherein the replacement cardiac valve includes commissures, and wherein the commissures are attached to the downstream end of the distal fixation member.

2. The apparatus according to claim 1, wherein the prosthesis is configured, upon implantation thereof, to gently embrace, without squeezing, leaflets of a native semilunar valve.

3. The apparatus according to claim 1, wherein the distal fixation member is configured to be positioned in an ascending aorta.

4. The apparatus according to claim 1, wherein the distal fixation member is configured to be positioned in a pulmonary trunk.

5. The apparatus according to claim 1, wherein the prosthesis is configured such that any radial force applied by the prosthesis outwardly against a native semilunar valve is insufficient by itself to chronically maintain the prosthesis in position with respect to a native valve complex under conditions of normal cardiac motion.

6. The apparatus according to claim 1, wherein the prosthesis is configured to apply the first axial force such that a ratio of (a) the first axial force to (b) a radial force applied outwardly by the prosthesis against a native semilunar valve is greater than 1.5:1.

7. The apparatus according to claim 1, wherein the prosthesis is configured to apply the second axial force such that a ratio of (a) the second axial force to (b) a radial force applied outwardly by the prosthesis against a native semilunar valve is greater than 1.5:1.

8. The apparatus according to claim 1, wherein the prosthesis is configured to apply a radial force of less than 0.5 pounds outwardly against a native semilunar valve.

9. The apparatus according to claim 1, wherein the distal fixation member does not press upon native valve commissures of a native semilunar valve upon implantation of the prosthesis.

10. The apparatus according to claim 1, wherein the prosthesis is configured to apply the first axial force with a force of at least 40 g during diastole.

11. The apparatus according to claim 1, wherein the prosthesis is configured to apply the second axial force with a force of at least 1 g during systole.

12. The apparatus according to claim 1, wherein the prosthesis is configured to apply the second axial force with a force of at least 5 g during systole.

13. The apparatus according to claim 1, wherein the distal fixation member is configured such that it does not fold over leaflets of a native semilunar valve upon implantation of the prosthesis.

14. The apparatus according to claim 1, wherein the prosthesis is configured to less than fully open leaflets of a native valve complex when the prosthesis is implanted at the native valve complex.

15. The apparatus according to claim 1, wherein the replacement cardiac valve is configured to assume a closed position during diastole and an open position during systole.

16. The apparatus according to claim 15, wherein the replacement cardiac valve comprises a collapsible pliant material, configured to assume the open and closed positions.

17. The apparatus according to claim 15, wherein the distal and proximal fixation members and the replacement cardiac valve are configured to define a single flow field through the distal and proximal fixation members and the replacement cardiac valve.

18. The apparatus according to claim 15, wherein the distal and proximal fixation members and the replacement cardiac valve are configured to define a plurality of flow fields through the distal and proximal fixation members and the replacement cardiac valve.

19. The apparatus according to claim 15, wherein the replacement cardiac valve comprises one or more prosthetic leaflets, and wherein the replacement cardiac valve is coupled to the prosthesis such that at least 50% of an axial length of the prosthetic leaflets is distal to native valve leaflets of a native semilunar valve upon implantation of the prosthesis.

* * * * *